(12) United States Patent
Audonnet et al.

(10) Patent No.: US 9,217,153 B2
(45) Date of Patent: Dec. 22, 2015

(54) ANTIBIOTIC-FREE PLASMIDS

(75) Inventors: Jean Christophe Francis Audonnet, Lyons (FR); Edmond Jolivet, Orlienas (FR)

(73) Assignee: MERIAL, INC., Duluth, GA (US)

( * ) Notice: Subject to any disclaimer, the term of this patent is extended or adjusted under 35 U.S.C. 154(b) by 766 days.

(21) Appl. No.: 12/786,186

(22) Filed: May 24, 2010

(65) Prior Publication Data

US 2010/0298419 A1    Nov. 25, 2010

Related U.S. Application Data

(60) Provisional application No. 61/180,755, filed on May 22, 2009.

(51) Int. Cl.
| | |
|---|---|
| A61K 31/7088 | (2006.01) |
| C12N 15/63 | (2006.01) |
| C12N 1/21 | (2006.01) |
| C12P 19/34 | (2006.01) |
| C12P 21/06 | (2006.01) |
| A61P 31/04 | (2006.01) |
| C07K 14/00 | (2006.01) |
| C12N 15/73 | (2006.01) |

(52) U.S. Cl.
CPC ..................................... *C12N 15/73* (2013.01)

(58) Field of Classification Search
None
See application file for complete search history.

(56) References Cited

U.S. PATENT DOCUMENTS

| | | | |
|---|---|---|---|
| 5,147,789 A | 9/1992 | Oppenheim et al. | 435/69.4 |
| 6,306,639 B1 * | 10/2001 | Woods et al. | 435/252.3 |

FOREIGN PATENT DOCUMENTS

| | | |
|---|---|---|
| WO | WO 01/09351 | 2/2001 |
| WO | WO03/097838 | 11/2003 |

OTHER PUBLICATIONS

Mairofer, J. et al., "A novel antibiotic free plasmid selection system: Advances in safe and efficient DNA therapy", Biotechnol. J., 3, 83-89, 2008.

Murphy, D. B., Epstein, S. L., "Guidance for Industry: Guidance for human somatic cell therapy and gene therapy, Food and Drug Administration", Rockville 1998.

Smith, H. A., Klinman, D. M., "The regulation of DNA vaccines", Curr. Opin. Biotechnol. 12, 299-203, 2001.

Cranenburgh, R. M., et al., "*Escherichia coli* strains that allow antibiotic-free plasmid selection and maintenance by repressor titration", Nucleic Acids Res. 2001, 29, e26.

Rozkov, A., et al., "Fed batch culture with declining specific growth rate for high-yielding production of a plasmid containing a gene therapy sequence in *Escherichia coli* DH1", Enzyme Microb. Technol. 2006, 39, 47-50.

Smith, M. A., et al., "Bacterial fitness and plasmid loss: the importance of culture conditions and plasmid size", Can. J. Microbiol. 1998, 44, 351-355.

Williams J.A. et al., Plasmid DNA vaccine vector design: Impact on efficacy, safety and upstream production, Biotechnol Adv (2009), doi:10.1016/j.biotechadv.1009.02.003.

Giladi H et al., "selective stabilization by the bacteriophage 434 repressor of the plasmid expressing bovine growth hormone in *Escherichia-coli*", applied and environmental microbiology, vol. 54, No. 5, p. 1297-1299, 1988.

Williams James A, et al., "plasmid Dna vaccine vector desing: impact on efficacy, safety and upstream production", Biotechnology Advances Jul.-Aug. 2009. LNKD-Pubmed:19233255, vol. 27, No. 4, p. 353-370, Jul. 2009.

Diana M Bower, et al., "Engineering of bacterial strains and vectors for the production of plasmid DNA", Applied Microbiology and Biotechnology, Srpinger, Gerlin, DE, vol. 82, No. 5, p. 805-813, Feb. 10, 2009.

* cited by examiner

*Primary Examiner* — Robert A Zeman
(74) *Attorney, Agent, or Firm* — Judy Jarecki-Black; Ruoying Chen; Merial, Inc.

(57) ABSTRACT

The present invention provides a method of maintaining a gram negative bacterium plasmid without the use of antibiotic selection pressure. Further, the invention relates to the drugless plasmids produced including drugless plasmids containing a heterologous gene. The invention also provides formulations and/or compositions comprising the drugless plasmids comprising a heterologous gene, formulations and/or compositions comprising a protein or an immunogen expressed using the drugless plasmids, and methods of administering such formulations and/or compositions to a host. The invention relates to gram negative bacteria containing the drugless plasmids.

23 Claims, 64 Drawing Sheets

30-37°C

*E. coli* – *sacB*+: Functional system "Sucrose resistance"
The plasmid maintenance is critical for enabling "sucrose resistance" to the *E. coli* host

Inactivated system "sucrose sensitivity"

Full cassette for allelic replacement of the *purN* gene

Full cassette for allelic replacement of the *edA* gene

Full sacB casette (ΔedAΩ λPr::sacB cat) for the allelic replacement of the edA gene into the ΔpurNΩ λPr::sacB Kan E. coli host strain
(for the generation of the double sacB cassette E. coli strain)

Figure 10B

1- BJ5183 Δ*purNΩ λPr::sacB* Km Δ*edaΩ λPr::sacB* Cat clone #1
2- BJ5183 Δ*purNΩ λPr::sacB* Km Δ*edaΩ λPr::sacB* Cat clone #2
3- BJ5183 Δ*purNΩ λPr::sacB* Km Δ*edaΩ λPr::sacB* Cat clone #3
4- BJ5183 Δ*purNΩ λPr::sacB* Km Δ*edaΩ λPr::sacB* Cat clone #4
5- BJ5183 Δ*purNΩ λPr::sacB* Km clone #16
6- BJ5183 Δ*edaΩ λPr::sacB* km clone #11
7- BJ5183 wild type

- Culture ⟹ OD600 ~ 1

- Serial dilution: from undiluted to $10^{-6}$ diluted sample

- Dot 3 µl on LB/agar plates (sucrose at 0%, 2%, 4%, 6%, 8% and to 10%)

- Incubation at 30°C and 42°C *

* 42°C to better increase spontaneous mutation rate to sucrose

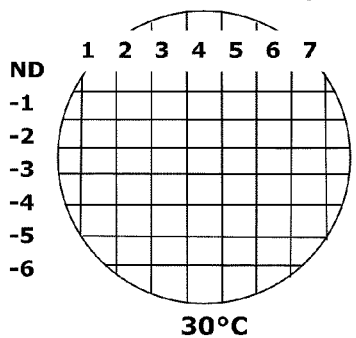
30°C

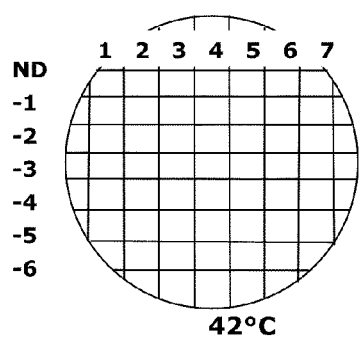
42°C

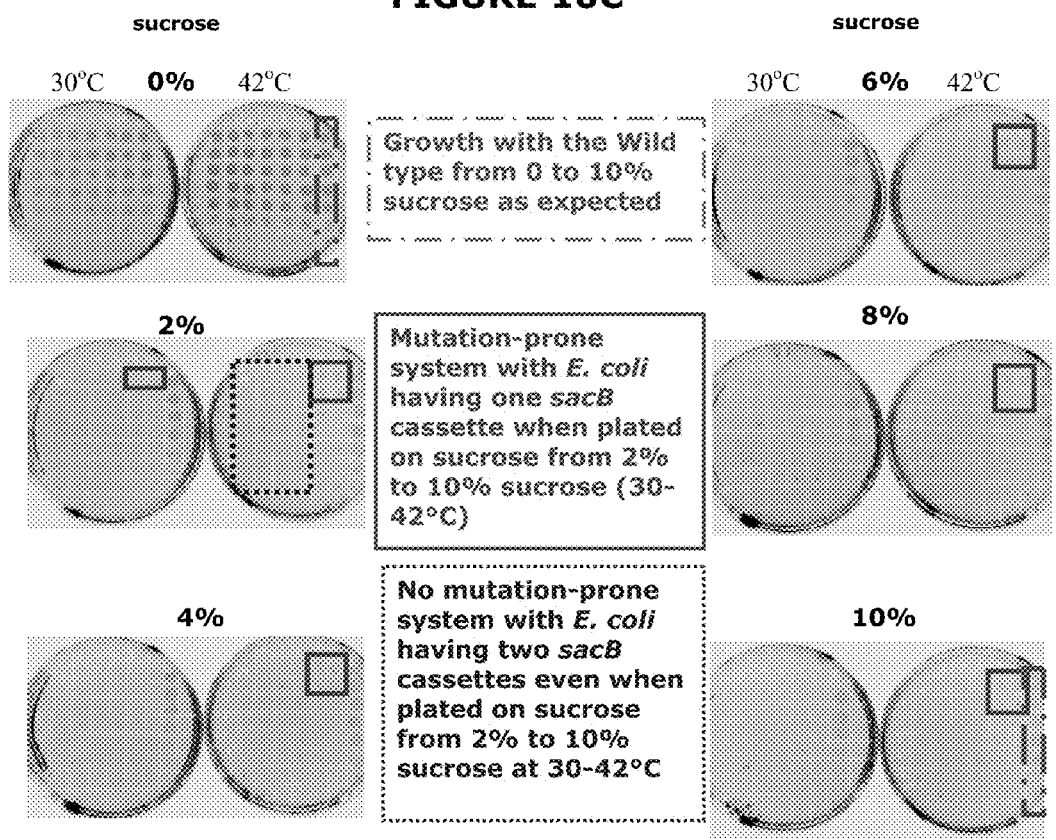

Extracted plasmids on Gel

Figure 12B
**BJ5183 Δ*purN*Ω λ*Pr::sacB* Km #16**
Single sacB cassette
2% sucrose
Single sacB assette
4% sucrose
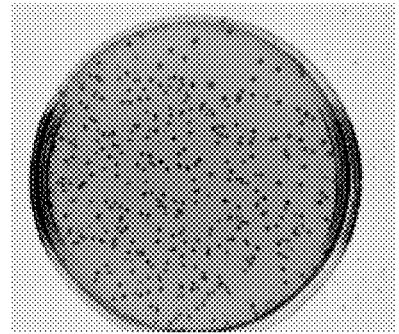
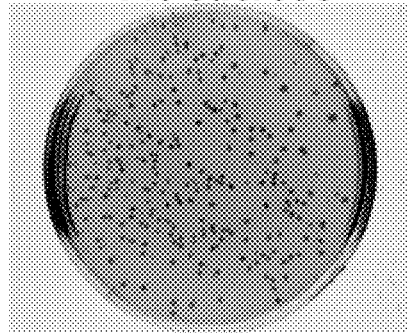
30°C
Δ*purN*Ω λ*Pr::sacB* Km   Δ*eda*Ω λ*Pr::sacB* cat #1
Double sacB cassette
2% sucrose
Double sacB cassette
4% sucrose
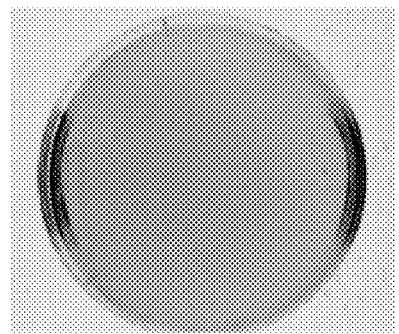
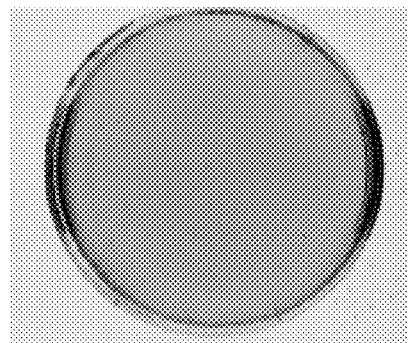

FIGURE 13B

Transformation of the *E. coli* sacB⁺ Δ*purN* strain with : { - pPB838 plasmid /1 µg
- pPB829 plasmid /1 µg ↓ 3 hours expression/cell wall regeneration at 30°C 100 µl spreading on LB/cat plate and LB/sucrose 10% plate (overnight @ 30°C)
Bacterial titer (transformant) (CFUs /100 µL)

| | Bacterial titer (CFUs /100 µL) | | | | | | | | | |
|---|---|---|---|---|---|---|---|---|---|---|
| | $10^{-1}$ | | $10^{-2}$ | | $10^{-3}$ | | $10^{-4}$ | | $10^{-5}$ | |
| | ca | su | ca | su | ca | su | ca | su | ca | su |
| sacB⁺Δ*purN* | 0 | ~100* | - | 1 | - | - | - | - | - | - |
| sacB⁺Δ*purN* + pPB82 | - | - | - | - | > | 9 | ~100 | 1 | 12 | 2 |
| sacB⁺Δ*purN* + pPB83 | - | - | - | - | > | 15 | ~100 | 2 | 9 | 2 |

▒ : Replica plate assay of transformant cells on LB /cat / sucrose and LB / sucrose plates
* : This spontaneous mutant number appears 3 days after incubation at 30°C
☐ : This corresponds to the Log dilution to be spread following transformation for selecting the cells harboring the antibiotic-free plasmids (pPB838 & pPB829)

FIGURE 14C

| Replica plate assay's Result | Colony Forming Unit (CFU) | | % colonies with plasmid |
|---|---|---|---|
| | Plate LB/sucrose | Plate LB/cat/sucrose | |
| sacB+ ΔpurN | 110 | 0 | 0 |
| sacB+ ΔpurN + pPB838 cat plate (10-4 dilution) | 1000 | 1000 | 100 |
| sacB+ ΔpurN + pPB838 cat plate (10-5 dilution) | 90 | 90 | 100 |
| sacB+ ΔpurN + pPB838 sucrose plate (10-3 dilution) | 150 | 147 | 98 |
| sacB+ ΔpurN + pPB838 sucrose plate (10-4 dilution) | 24 | 23 | 95 |

Extraction from 2 ml culture of the pPB838 and pPB829 Plasmid and determination of the plasmid copy number per cell Figure 15F
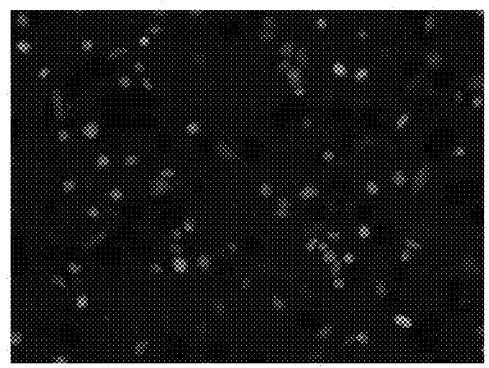
pCG105 / CHO
Cat selection pressure
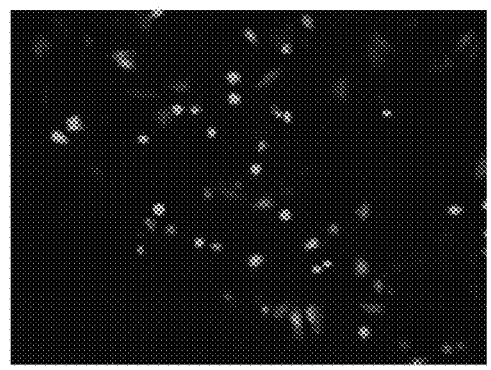
pPB896 / CHO
Sucrose selection pressure pCRblunt + PB1184-1185 plasmid map pPB828 plasmid map pPB844 map pPB846 map pPB847 map

Figure 26A

Sequence alignment of cI proteins

```
                        1                                                  50
    ABO40666 (cI)   (1) MS KKNLITQEQLEDARPLKAIYEK NELGL QESVADKMGMQSGVGA
    ABO40673 (cI)   (1) MSAKKK LTQEQLEDARRLKAIYEK KNELGL QESVADKMGMQSGVGA
    ABO40681 (cI)   (1) MSAKKK LTQEQLEDARRLKAIYEK KNELGL QESVADKMGMQSGVGA
    ABO40689 (cI)   (1) MSAKKK LTQEQLEDARRLKAIYEK KNELGLPQESVADKMGMQSGVGA
    BAE79430 (cI)   (1) MS KKK LTQEQLEDARRLKAIYEK KNELGL QESVADKMGMQSGVGA
    cI857 (SEQ 2)   (1) MS KKK LTQEQLEDARPLKAIYEK KNELGL QESVADKMGMQSGVGA
    NP_040628 (cI)  (1) MS KKK LTQEQLEDARPLKAIYEK KNELGL QESVADKMGMQSGVGA
    NP_285963 (cI)  (1) MSAKKK LTQEQLEDARRLKAIYEK KNELGL QESVADKMGMQSGVGA
    ZP_04798993 (cI)(1) MS KKK LTQEQLEDARRLKAIYEK KNELGL QESVADKMGMQSGVGA 51                                                 100
    ABO40666 (cI)  (51) LFNGINALNAYNAALL KIL VSVEEFSPSIAREIYEMYEAVSMQPSLRS
    ABO40673 (cI)  (51) LFNGINALNAYNAALL R LNVSVEEFSPSIAREIYEMYEAVSMQPSLRS
    ABO40681 (cI)  (51) LFNGINALNAYRAALL KTL VSVEEFSPSIAREIYEMYEAVSMQPSLRS
    ABO40689 (cI)  (51) LFNGINALNAYRAALL KIL VSVEEFSPSIAREIYEMYEAVSMQPSLRS
    BAE79430 (cI)  (51) LFNGINALNAYNAALL KIL VSVEEFSPSIAREIYEMYEAVSMQPSLRS
    cI857 (SEQ 2)  (51) LFNGINALNAYNKALLTKIL VSVEEFSPSIAREIYEMYEAVSMQPSLRS
    NP_040628 (cI) (51) LFNGINALNAYNAALL KIL VSVEEFSPSIAREIYEMYEAVSMQPSLRS
    NP_285963 (cI) (51) LFNGINALNAYRAALL KTLNVSVEEFSPSIAREIYEMYEAVSMQPSLRS
    ZP_04798993(cI)(51) LFNGINALNAYRAALLTKIL VSVEEFSPSIAREIYEMYEAVSMQPSLRS 101                                                150
    ABO40666 (cI) (101) EYEYPVFSHVQAGMFSP LPTFTK DAE KVSTTKKAS SAFWLEVEGNS
    ABO40673 (cI) (101) EYEYPVFSHVQAGMFSP LPTFTK DAE KVSTTKKAS SAFWLEVEGNS
    ABO40681 (cI) (101) EYEYPVFSHVQAGMFSP LRTFTK DAE KVSTTKKAS SAFWLEVEGNS
    ABO40689 (cI) (101) EYEYPVFSHVQAGMFSP LKTFTK DAE KVSTTKKAS SAFWLEVEGNS
    BAE79430 (cI) (101) EYEYPVFSHVQAGMFSPKLRTFTK DAE KVSTTKKAS SAFWLEVEGNS
    cI857 (SEQ 2) (101) EYEYPVFSHVQAGMFSPKLRTFTK DAE KVSTTKKAS SAFWLEVEGNS
    NP_040628 (cI)(101) EYEYPVFSHVQAGMFSP LPTFTK DAE KVSTTKKAS SAFWLEVEGNS
    NP_285963 (cI)(101) EYEYPVFSHVQAGMFSP LPTFTK DAE KVSTTKKASCSAFWLEVEGNS
    ZP_04798993(cI)(101)EYEYPVFSHVQAGMFSPKLRTFTK DAE KVSTTKKAS SAFWLEVEGNS 151                                                200
    ABO40666 (cI) (151) MTAPT KPSFPDGMLILVDPEQ VEPGDFCIARLGGDEFTFKKLIRDSG
    ABO40673 (cI) (151) MTAPTGYKPSFPDGMLILVDPEQTVEPGDFCIARLGGDEFTFKKLIPDSG
    ABO40681 (cI) (151) MTAPTG KPSFPDGMLILVDPEQ VEPGDFCIARLGGDEFTFKKLIRDSG
    ABO40689 (cI) (151) MTAPTG KPSFPDGMLILVDPEQ VEPGLECIARLGGDEFTFKKLIRDSG
    BAE79430 (cI) (151) MTAPTG KPSFPDGMLILVDPEQ VEPGDFCIARLGGDEFTFKKLIRDSG
    cI857 (SEQ 2) (151) MTAPT KPSFPDGMLILVDPEQ VEPGDFCIARLGGDEFTFKKLIRDSG
    NP_040628 (cI)(151) MTAPT KPSFPDGMLILVDPEQ VEPGDFCIARLGGDEFTFKKLIRDSG
    NP_285963 (cI)(151) MTAPT KPSFPDGMLILVDPEQ VEPGDFCIARLGGDEFTFKKLIRDSG
    ZP_04798993(cI)(151)MTAPTG KPSFPDGMLILVDPEQ VEPGDFCIARLGGDEFTFKKLIRDSG
```

Figure 26B

```
                           201                                    237
    AB040666 (cI)   (201)  QVFLQPLNPQYPMIPCNESCSVVGKVIASQWPEETFG
    AB040673 (cI)   (201)  QVFLQPLNPQYPMIPCNESCSVVGKVIASQWPEETFG
    AB040681 (cI)   (201)  QVFLQPLNPQYPMIPCNESCSVVGKVIASQWPEETFG
    AB040689 (cI)   (201)  QVFLQPLNPQYPMIPCNESCVVGKVIASQWPEETFG
    BAE79430 (cI)   (201)  QVFLQPLNPQYPMIPCNESCSVVGKVIASQWPEETFG
    cI857 (SEQ 2)   (201)  QVFLQPLNPQYPMIPCNESCSVVGKVIASQWPEETFG
    NP_040628 (cI)  (201)  QVFLQPLNPQYPMIPCNESCSVVGKVIASQWPEETFG
    NP_285963 (cI)  (201)  QVFLQPLNPQYPMIPCNESCSVVGKVIASQWPEETFG
    ZP_04798993(cI) (201)  QVFLQPLNPQYPMIPCNESCSVVGNVIASQWPEETFG cI857 (SEQ ID NO:2)(sequence identity percentage)
    AB040666   (SEQ ID NO:44)       98.7%
    AB040673   (SEQ ID NO:46)       96.2%
    AB040681   (SEQ ID NO:48)       98.7%
    AB040689   (SEQ ID NO:50)       98.3%
    BAE79430   (SEQ ID NO:52)       99.6%
    NP_040628  (SEQ ID NO:54)       99.2%
    NP_285963  (SEQ ID NO:56)       97.5%
    ZP_04798993(SEQ ID NO:58)       99.6%
```

Figure 27A

Sequence alignment of SacB proteins

Figure 27B

```
                 201                                              250
    AAA72302   (201)  KSD  LKINGVED KS IFDGD KTYQNVQQFIDEGNY SGDNHTLRDPHY
    AAN75494   (201)  TSD  LKINGVED KS IFDGD KTYQNVQQFIDEGNY SGDNHTLRDPHY
    ACD39394   (201)  KSDD LKINGVED    IFDGD KTYQNVQQFIDEGNY SGDNHTLRDPHY
     P94468    (201)  KSD  LKINGVED KS IFDGDSKTYQNVQQFIDEGNY SGDNHTLPDPHY
    AAZ04375   (201)  KSD  LKINGVED KS IFDGD KTYQNVQQFIDEGNY SGDNHTLRDPHY
    ABM88723   (201)  KSD  LKINGVED KS IFDGD KTYQNVQQFIDEGNY SGDNHTLRDPHY
    ACJ66845   (201)  KSD  LKINGVED KS IFDGD KTYQNVQQFIDEGNY SGDNHTLRDPHY
    NP_391325  (201)  KSD  LKINGVED KS IFDGD KTYQNVQQFIDEGNY SGDNHTLRDPHY
   SacB (SEQ 4)(201)  KSD  LKINGVED KS IFDGD KTYQNVQQFIDEGNY SGDNHTLRDPHY 251                                              300
    AAA72302   (251)  VEDKGHKYLVFEANTGTE GYQGEESLFNKAYYG ST FFR ESQKL QS
    AAN75494   (251)  VEDKGHKYLVFEANTGTE GYQGEESLFNKAYYG ST FFR ESQKL QS
    ACD39394   (251)  VEDKGHKYLVFEANTGTENGYQGEESLFNKAYYGGSTNFFRAESQKLQQS
     P94468    (251)  VEDKGHKYLVFEANTGTE GYQGEESLFNKAYYG ST FFR ESQKL QS
    AAZ04375   (251)  VEDKGHKYLVFEANTGTE GYQGEESLFNKAYYG ST FFR ESQKL QS
    ABM88723   (251)  VEDKGHKYLVFEANTGTE GYQGEESLFNKAYYG ST FFR ESQKL QS
    ACJ66845   (251)  VEDKGHKYLVFEANTGTE GYQGEESLFNKAYYG ST FFR ESQKL QS
    NP_391325  (251)  VEDKGHKYLVFEANTGTE GYQGEESLFNKAYYG ST FFR ESQKL QS
   SacB (SEQ 4)(251)  VEDKGHKYLVFEANTGTE GYQGEESLFNKAYYG ST FFR ESQKL QS 301                                              350
    AAA72302   (301)  KKR AELANGALGM ELNDDYTLKKVMKPLI SNTVTDEIERANVFKMN
    AAN75494   (301)  KKR AELANGALGM ELNDDYTLKKVMKPLITSNTVTDEIERANVFKMN
    ACD39394   (301)  AK PDAELANGALGM ELNDDYTLKKVMKPLITSNTVTDEIERANVFKMN
     P94468    (301)  KNR AELANGALGM ELNDDYTLKKVMKPLI SNTVTDEIERANVFKMN
    AAZ04375   (301)  KKR AELANGALGM ELNDDYTLKKVMKPLI SNTVTDEIERANVFKMN
    ABM88723   (301)  KKR AELANGALGM ELNDDYTLKKVMKPLI SNTVTDEIERANVFKMN
    ACJ66845   (301)  KKR AELANGALGM ELNDDYTLKKVMKPLI SNTVTDEIERANVFKMN
    NP_391325  (301)  KKR AELANGALGM ELNDDYTLKKVMKPLI SNTVTDEIERANVFKMN
   SacB (SEQ 4)(301)  KKR AELANGALGM ELNDDYTLKKVMKPLI SNTVTDEIERANVFKMN 351                                              400
    AAA72302   (351)  GKWYL TDSRGS MTIDGI SNDIYMLGYVSNSLTGPYKPLNKTGLVL
    AAN75494   (351)  GKWYL TDSRGS MTIDGI SNDIYMLGYVSNSLTGPYKPLNKTGLVL
    ACD39394   (351)  GKWYL TDSRGS MTIDGINSNDIYMLGYVSNSLTGPYKPLNKTGLVLQM
     P94468    (351)  GKWYLSTIGPGSQMTIEGI ENDIYMLGYVSNSLTGPYKPLNKTGLVL
    AAZ04375   (351)  GKWYL TDSRGS MTIDGI SNDIYMLGYVSNSLTGPYKPLNKTGLVL
    ABM88723   (351)  GKWYL TDSRGS MTIDGI SNDIYMLGYVSNSLTGPYKPLNKTGLVL
    ACJ66845   (351)  GKWYL TDSRGS MTIDGI SNDIYMLGYVSNSLTGPYKPLNKTGLVL
    NP_391325  (351)  GKWYL TDSRGS MTIDGI SNDIYMLGYVSNSLTGPYKPLNKTGLVL
   SacB (SEQ 4)(351)  GKWYL TDSRGS MTIDGI SNDIYMLGYVSNSLTGPYKPLNKTGLVL
```

Figure 27C

```
                         401                                                450
        AAA72302  (401)  LLDPNDVTFTYSHFAVPQA GNNVVITSYMTNRGF DK  TFAPSFL
        AAN75494  (401)  LLDPNDVTFTYSHFAVPQA GNNVVITSYMTNRGF DK  TFAPSFL
        ACD39394  (401)  GLDPNDVTFTYSHFAVPQA GNNVVITSYMTNRGF EDK  TFAPSFL
          P94468  (401)  LLDPNDVTFTYSHFAVPQAIGNNVVITSYMTNRGF LR  TFAPSFL
        AAZ04375  (401)  LLDPNDVTFTYSHFAVPQA GNNVVITSYMTNRGF DK  TFAPSFL
        ABM88723  (401)  LLDPNDVTFTYSHFAVPQA GNNVVITSYMTNRGF DK  TFAPSFL
        ACJ66845  (401)  LLDPNDVTFTYSHFAVPQA GNNVVITSYMTNRGF DK  TFAPSFL
        NP_391325 (401)  LLDPNDVTFTYSHFAVPQA GNNVVITSYMTNRGF DK  TFAPSFL
        SacB (SEQ 4) (401) LLDPNDVTFTYSHFAVPQA GNNVVITSYMTNRGF DK  TFAPSFL 451             473
        AAA72302  (451)  I  GRKTSVVK SII  GQLTVR
        AAN75494  (451)  I  GRKTSVVK SII  GQLTVNQ
        ACD39394  (451)  I  GRKTSVVKNSII  GQLTVNN
          P94468  (451)  TQGKRTSVVKASII  GQLTVNQ
        AAZ04375  (451)  I  GRKTSVVK SII  GQLTVR
        ABM88723  (451)  I  GRKTSVVK SII  GQLTVR
        ACJ66845  (451)  I  GRKTSVVK SII  GQLTVR
        NP_391325 (451)  I  GRKTSVVK SII  GQLTVR
        SacB (SEQ 4) (451) I  GRKTSVVK SII  GQLTVR
```

```
                              SacB (SEQ ID NO:4)  (sequence identity percentage)
        AAA72302 (SEQ ID NO:60)    99.8%
        AAN75494 (SEQ ID NO:62)    98.9%
        ACD39394 (SEQ ID NO:64)    90.3%
          P94468 (SEQ ID NO:74)    97.7%
        AAZ04375 (SEQ ID NO:66)    99.8%
        ABM88723 (SEQ ID NO:68)    99.6%
        ACJ66845 (SEQ ID NO:70)    99.8%
        NP_391325 (SEQ ID NO:72)   100%
```

Figure 28A

| SEQ ID NO: | Type | Gene Description |
|---|---|---|
| 1 | DNA | cI857 DNA |
| 2 | Protein | cI857 protein (AAN86071, 100% over the entire length) |
| 3 | DNA | sacB DNA |
| 4 | Protein | sacB protein (NP391325) |
| 5 | DNA | Lambda promoter λpR |
| 6 | oligo | PB1232 |
| 7 | oligo | PB1233 |
| 8 | oligo | PB1234 |
| 9 | oligo | PB1192 |
| 10 | oligo | PB1193 |
| 11 | oligo | PB1194 |
| 12 | oligo | PB1195 |
| 13 | oligo | PB1196 |
| 14 | oligo | PB1197 |
| 15 | oligo | PB1237 |
| 16 | oligo | PB1199 |
| 17 | oligo | PB1200 |
| 18 | oligo | PB1238 |
| 19 | oligo | PB1235 |
| 20 | oligo | PB1209 |
| 21 | oligo | PB1210 |
| 22 | oligo | PB1236 |
| 23 | oligo | PB1204 |
| 24 | oligo | PB1205 |
| 25 | oligo | PB1214 |
| 26 | oligo | PB1215 |
| 27 | oligo | PB1213 |
| 28 | oligo | PB1212 |
| 29 | DNA | P1 promoter – weak promoter of Kanamycin gene (1) |
| 30 | DNA | cI gene native promoter |
| 31 | DNA | Cat gene (chloramphenicol acetyl transferase), 798bp |
| 32 | protein | Cat protein |
| 33 | oligo | PB1184 |
| 34 | oligo | PB1185 |
| 35 | oligo | PB1186 |
| 36 | oligo | PB1187 |
| 37 | oligo | PB1188 |
| 38 | oligo | PB1189 |
| 39 | oligo | PB1182 |
| 40 | oligo | PB1183 |
| 41 | oligo | PB1263 |

| Figure 28B |||
|---|---|---|
| 42 | oligo | PB1266 |
| 43 | DNA | CMV promoter |
| 44 | protein | ABO40666 (cI protein) |
| 45 | DNA | EF120455 |
| 46 | protein | ABO40673 (cI protein) |
| 47 | DNA | EF120456 |
| 48 | protein | ABO40681 (cI protein) |
| 49 | DNA | EF120457 |
| 50 | protein | ABO40689 (cI protein) |
| 51 | DNA | EF120458 |
| 52 | protein | BAE79430 (cI protein) |
| 53 | DNA | AB248918 |
| 54 | protein | NP_040628 (cI protein) |
| 55 | DNA | NC_001416 |
| 56 | protein | NP_285963 (cI protein) |
| 57 | DNA | NC_002655 |
| 58 | protein | ZP_04798993 (cI protein) |
| 59 | DNA | NZ_ACJP01000210 |
| 60 | protein | AAA72302 (sacB protein) |
| 61 | DNA | L05081 |
| 62 | protein | AAN75494 (sacB protein) |
| 63 | DNA | AY150365 |
| 64 | protein | ACD39394 (sacB protein) |
| 65 | DNA | EU668142 |
| 66 | protein | AAZ04375 (sacB protein) |
| 67 | DNA | DQ095874 |
| 68 | protein | ABM88723 (sacB protein) |
| 69 | DNA | EF198106 |
| 70 | protein | ACJ66845 (sacB protein) |
| 71 | DNA | FJ437239 |
| 72 | protein | NP_391325 (sacB protein) |
| 73 | DNA | NC_000964 |
| 74 | protein | P94468 |
| 75 | DNA | sacB cassette (λpR promoter + 5' UTR + sacB gene) |
| 76 | DNA | P1 promoter + cI gene in pPB829 (3320bp-4168bp) and in pPB838 (1076bp-1924bp) |
| 77 | DNA | cI native promoter + cI gene in pPB846 and pPB847 |
| 78 | DNA | pPB838 plasmid sequence |
| 79 | DNA | pPB829 plasmid sequence |
| 80 | oligo | PB1320 |
| 81 | oligo | PB1321 |
| 82 | oligo | PB1322 |
| 83 | DNA | P1 promoter – weak promoter of Kanamycin gene (2) |

Figure 29A

```
                    1                                                50
AB248918       (1)  ATGAGCACAAAAAAGAAACNNTTAACACAAGAGCAGCTTGAGGACGCACG
EF120455       (1)  ATGAGCACAAAAAAGAAACTNTTAACACAAGAGCAGCTTGAGGACGCACG
EF120456       (1)  ATGAGCGCAAAAAAGAAACGGTTAACACAAGAGCAGCTTGAGGACGCACG
NC_002655      (1)  ATGAGCGCAAAAAAGAAACNNTTAACACAAGAGCAGCTTGAGGACGCACG
EF120457       (1)  ATGAGCGCAAAAAAGAAACNATTAACACAAGAGCAGCTTGAGGACGCACG
EF120458       (1)  ATGAGCGCAAAAAAGAAACNNTTAACACAAGAGCAGCTTGAGGACGCACG
NC_001416      (1)  ATGAGCACAAAAAAGAAACNNTTAACACAAGAGCAGCTTGAGGACGCACG
cI857(SEQ1)    (1)  ATGAGCACAAAAAAGAAACNNTTAACACAAGAGCAGCTTGAGGACGCACG
NZ_ACJP01000210(1)  ATGAGCACAAAAAAGAAACNNTTAACACAAGAGCAGCTTGAGGACGCACG 51                                               100
AB248918      (51)  TCGCCTTAAAGCNATTTATGAAAAAANGAAAAATGAACTTGGCTTANCN
EF120455      (51)  TCGCCTTAAAGCNATTTATGAAAAAANGAAAAATGAACTTGGCTTANCN
EF120456      (51)  TCGCCTTAAAGCTATTTATGAAAAAANGAAAAATGAACTTGGCTTACTC
NC_002655     (51)  TCGCCTTAAAGCTATTTATGAAAAAANGAAAAATGAACTTGGCTTANCN
EF120457      (51)  TCGCCTTAAAGCNATTTATGAAAAAANGAAAAATGAACTTGGCTTANCN
EF120458      (51)  TCGCCTTAAAGCNATTTATGAAAAAANGAAAAATGAACTTGGCTTACCN
NC_001416     (51)  TCGCCTTAAAGCNATTTATGAAAAAANGAAAAATGAACTTGGCTTANCN
cI857(SEQ1)   (51)  TCGCCTTAAAGCNATTTATGAAAAAANGAAAAATGAACTTGGCTTANCN
NZ_ACJP01000210(51) TCGCCTTAAAGCNATTTATGAAAAAAGGAAAAATGAACTTGGCTTANCN 101                                              150
AB248918     (101)  AGGAATCTGTCGCAGACAAGATGGGGATGGGGCAGTCAGGCGTTGGTGCT
EF120455     (101)  AGGAATCTGTCGCAGACAAGATGGGGATGGGGCAGTCAGGCGTTGGTGCT
EF120456     (101)  AGGAATCTGTCGCAGACAAGATGGGGATGGGGCAGTCAGGCGTTGGTGCT
NC_002655    (101)  AGGAATCTGTCGCAGACAAGATGGGGATGGGGCAGTCAGGCGTTGGTGCT
EF120457     (101)  AGGAATCTGTCGCAGACAAGATGGGGATGGGGCAGTCAGGCGTTGGTGCT
EF120458     (101)  AGGAATCTGTCGCAGACAAGATGGGGATGGGGCAGTCAGGCGTTGGTGCT
NC_001416    (101)  AGGAATCTGTCGCAGACAAGATGGGGATGGGGCAGTCAGGCGTTGGTGCT
cI857(SEQ1)  (101)  AGGAATCTGTCGCAGACAAGATGGGGATGGGGCAGTCAGGCGTTGGTGCT
NZ_ACJP01000210(101)AGGAATCTGTCGCAGACAAGATGGGGATGGGGCAGTCAGGCGTTGGTGCT 151                                              200
AB248918     (151)  TTATTTAATGGNATCAATGCATTAAATGCTTATAACGCCGCATTGCTTNN
EF120455     (151)  TTATTTAATGGNATCAATGCATTAAATGCTTATAACGCCGCATTGCTTNN
EF120456     (151)  TTATTTAATGGTATCAATGCATTAAATGCTTATAACGCCGCATTGCTTNN
NC_002655    (151)  TTATTTAATGGNATCAATGCATTAAATGCTTATAACGCCGCATTGCTTNN
EF120457     (151)  TTATTTAATGGNATCAATGCATTAAATGCTTATAACGCCGCATTGCTTNN
EF120458     (151)  TTATTTAATGGNATCAATGCATTAAATGCTTATAACGCCGCATTGCTTNN
NC_001416    (151)  TTATTTAATGGNATCAATGCATTAAATGCTTATAACGCCGCATTGCTTNN
cI857(SEQ1)  (151)  TTATTTAATGGNATCAATGCATTAAATGCTTATAACGCCGCATTGCTTAC
NZ_ACJP01000210(151)TTATTTAATGGNATCAATGCATTAAATGCTTATAACGCCGCATTGCTTAC
```

Figure 29B

```
                         201                                                250
AB248918         (201)   AAAAATTCTCAAGGTTAGCGTTGAAGAATTTAGCCCTTCAATCGCCAGAG
EF120455         (201)   AAAAATTCTCAAGGTTAGCGTTGAAGAATTTAGCCCTTCAATCGCCAGAG
EF120456         (201)   AAAAATTCTCAACGTTAGCGTTGAAGAATTTAGCCCTTCAATCGCCAGAG
NC_002655        (201)   AAAAATTCTCAACGTTAGCGTTGAAGAATTTAGCCCTTCAATCGCCAGAG
EF120457         (201)   AAAAATTCTCAAGGTTAGCGTTGAAGAATTTAGCCCTTCAATCGCCAGAG
EF120458         (201)   AAAAATTCTCAAGGTTAGCGTTGAAGAATTTAGCCCTTCAATCGCCAGAG
NC_001416        (201)   AAAAATTCTCAAGGTTAGCGTTGAAGAATTTAGCCCTTCAATCGCCAGAG
cI857(SEQ1)      (201)   AAAAATTCTCAAGGTTAGCGTTGAAGAATTTAGCCCTTCAATCGCCAGAG
NZ_ACJP01000210  (201)   AAAAATTCTCAAGGTTAGCGTTGAAGAATTTAGCCCTTCAATCGCCAGAG 251                                                300
AB248918         (251)   AAATCTACGAGATGTATGAAGCGGTTAGTATGCAGCCGTCACTTAGAAGT
EF120455         (251)   AAATCTACGAGATGTATGAAGCGGTTAGTATGCAGCCGTCACTTAGAAGT
EF120456         (251)   AAATCTACGAGATGTATGAAGCGGTTAGTATGCAGCCGTCACTTAGAAGT
NC_002655        (251)   AAATCTACGAGATGTATGAAGCGGTTAGTATGCAGCCGTCACTTAGAAGT
EF120457         (251)   AAATCTACGAGATGTATGAAGCGGTTAGTATGCAGCCGTCACTTAGAAGT
EF120458         (251)   AAATCTACGAGATGTATGAAGCGGTTAGTATGCAGCCGTCACTTAGAAGT
NC_001416        (251)   AAATCTACGAGATGTATGAAGCGGTTAGTATGCAGCCGTCACTTAGAAGT
cI857(SEQ1)      (251)   AAATCTACGAGATGTATGAAGCGGTTAGTATGCAGCCGTCACTTAGAAGT
NZ_ACJP01000210  (251)   AAATCTACGAGATGTATGAAGCGGTTAGTATGCAGCCGTCACTTAGAAGT 301                                                350
AB248918         (301)   GAGTATGAGTACCCGTTTTTTCTCATGTTCAGGCCGGGATGTTCTCGCC
EF120455         (301)   GAGTATGAGTACCCGTTTTTTCTCATGTTCAGGCCGGGATGTTCTCGCC
EF120456         (301)   GAGTATGAGTACCCGTTTTTTCTCATGTTCAGGCCGGGATGTTCTCGCC
NC_002655        (301)   GAGTATGAGTACCCGTTTTTTCTCATGTTCAGGCCGGGATGTTCTCGCC
EF120457         (301)   GAGTATGAGTACCCGTTTTTTCTCATGTTCAGGCCGGGATGTTCTCGCC
EF120458         (301)   GAGTATGAGTACCCGTTTTTTCTCATGTTCAGGCCGGGATGTTCTCGCC
NC_001416        (301)   GAGTATGAGTACCCGTTTTTTCTCATGTTCAGGCCGGGATGTTCTCGCC
cI857(SEQ1)      (301)   GAGTATGAGTACCCGTTTTTTCTCATGTTCAGGCCGGGATGTTCTCGCC
NZ_ACJP01000210  (301)   GAGTATGAGTACCCGTTTTTTCTCATGTTCAGGCCGGGATGTTCTCGCC 351                                                400
AB248918         (351)   TAAGCTTAGAACCTTTACCAAAGCGATGCGGACAGATGGGTAAGCACAA
EF120455         (351)   TAAGCTTAGAACCTTTACCAAAGCGATGCGGACAGATGGGTAAGCACAA
EF120456         (351)   TAAGCTTAGAACCTTTACCAAAGCGATGCGGACAAATGGGTAAGCACAA
NC_002655        (351)   TAAGCTTAGAACCTTTACCAAAGCGATGCGGAGAAATGGGTAAGCACAA
EF120457         (351)   TAAGCTTAGAACCTTTACCAAAGCGATGCGGACAGATGGGTAAGCACAA
EF120458         (351)   TAAGCTTAGAACCTTTACCAAAGCGATGCGGACAGATGGGTAAGCACAA
NC_001416        (351)   TAAGCTTAGAACCTTTACCAAAGCGATGCGGACAGATGGGTAAGCACAA
cI857(SEQ1)      (351)   TAAGCTTAGAACCTTTACCAAAGCGATGCGGACAGATGGGTAAGCACAA
NZ_ACJP01000210  (351)   TAAGCTTAGAACCTTTACCAAAGCGATGCGGACAGATGGGTAAGCACAA
```

```
              651                                              700
AB248918      (651) TGAGAGTTGGTCCGTTGTGGGAAAGTTATCGGAGTCAGTGGCCGAAG
EF120455      (651) TGAGAGTTGGTCCGTTGTGGGAAAGTTATCGCCAGCCAGTGGCCAGAAG
EF120456      (651) TGAGAGTTGGCTCCGTTGTGGGAAAGTTATCGCAGTCAGTGGCCGAAG
NC_002655     (651) TGAGAGTTGGTCCGTTGTGGGAAAGTTATCGGAGTCAGTGGCCGAAG
EF120457      (651) TGAGAGTTGGTCCGTTGTGGGAAAGTTATCGGAGTCAGTGGCCGAAG
EF120458      (651) TGAGAGTTGGTCCGTTGTGGGAAAGTTATCGCAGTCAGTGGCCGAAG
NC_001416     (651) TGAGAGTTGGTCCGTTGTGGGAAAGTTATCGCAGTCAGTGGCCGAAG
cI857(SEQ1)   (651) TGAGAGTTGGTCCGTTGTGGGAAAGTTATCGGAGTCAGTGGCCGAAG
NZ_ACJP01000210(651) TGAGAGTTGGTCCGTTGTGGGAAAGTTATCGGAGTCAGTGGCCGAAG 701        714
AB248918      (701) AGACGTTTGG
EF120455      (701) AGACGTTTGG
EF120456      (701) AGACGTTTGGTAA
NC_002655     (701) AGACGTTTGGG
EF120457      (701) AGACGTTTGGG
EF120458      (701) AGACGTTTGGG
NC_001416     (701) AGACGTTTGG
cI857(SEQ1)   (701) AGACGTTTGG ---
NZ_ACJP01000210(701) AGACGTTTGG
```

|  | cI857 (SEQ ID NO:1) (sequence identity) |
|---|---|
| AB248918 (SEQ ID NO:53) | 99.4% |
| EF120455 (SEQ ID NO:45) | 98.0% |
| EF120456 (SEQ ID NO:47) | 95.5% |
| NC_002655(SEQ ID NO:57) | 96.5% |
| EF120457 (SEQ ID NO:49) | 98.5% |
| EF120458 (SEQ ID NO:51) | 98.3% |
| NC_001416(SEQ ID NO:55) | 99.3% |
| NZ_ACJP01000210(SEQ ID NO:59) | 99.4% |

Figure 30A

```
                      1                                                  50
AY150365       (1)    ATGAACATCAAAAA TTTGCAAAAC AGC ACAGT  TAAC TTTAC AC
EU668142       (1)    ATGAACATCAAAAAATTTGCAAAACGAGCCACAGTTCTAACTTTTACGAC
L05081         (1)    ATGAACATCAAAAA TTTGCAAAAC AGC ACAGT  TAAC TTTAC AC
DQ095874       (1)    ATGAACATCAAAAA TTTGCAAAAC AGC ACAGT  TAAC TTTAC AC
EF198106       (1)    ATGAACATCAAAAA TTTGCAAAAC AGC ACAGT  TAAC TTTAC AC
FJ437239       (1)    ATGAACATCAAAAA TTTGCAAAAC AGC ACAGT  TAAC TTTAC AC
NC_000964      (1)    ATGAACATCAAAAA TTTGCAAAAC AGC ACAGT  TAAC TTTAC AC
sacB(SEQ 3)    (1)    ATGAACATCAAAAA TTTGCAAAAC AGC ACAGT  TAAC TTTAC AC 51                                                 100
AY150365       (51)    GCAC CTGGCAGG GG GC ACTCAAGC TT  GCGAAAGAAA  A CC
EU668142       (51)   TGCAC TCTGGCAGGGGGA CGACTCAAGCCCTTCGCGAAAGAAAATACCC
L05081         (51)    GCAC CTGGCAGG GG GC ACTCAAGC TT  GCGAAAGAAA  A CC
DQ095874       (51)    GCAC CTGGCAGG GG GC ACTCAAG  TT  GCGAAAGAAA  A CC
EF198106       (51)    GCAC CTGGCAGG GG GC ACTCAAGC TT  GCGAAAGAAA  A CC
FJ437239       (51)    GCAC CTGGCAGG GG GC ACTCAAGC TT  GCGAAAGAAA  A CC
NC_000964      (51)    GCAC CTGGCAGG GG GC ACTCAAGC TT  GCGAAAGAAA  A CC
sacB(SEQ 3)    (51)    GCAC CTGGCAGG GG GC ACTCAAGC TT  GCGAAAGAAA  A CC 101                                                150
AY150365       (101)  AAAA CC TA AA  GAAAC TACGGC T  C CATAT ACACGCCATGAT
EU668142       (101)  AAAACCTTACAAAGAAACGTACGGCGTCTCCATATCACACGCCATGAT
L05081         (101)  AAAA CC TA AA  GAAAC TACGGC T  C CATAT ACACGCCATGAT
DQ095874       (101)  AAAA CC TA AA  GAAAC TACGGC T  C CATAT ACACGCCATGAT
EF198106       (101)  AAAA CC TA AA  GAAAC TACGGC T  C CATAT ACACGCCATGAT
FJ437239       (101)  AAAA CC TA AA  GAAAC TACGGC T  C CATAT ACACGCCATGAT
NC_000964      (101)  AAAA CC TA AA  GAAAC TACGGC T  C CATAT ACACGCCATGAT
sacB(SEQ 3)    (101)  AAAA CC TA AA  GAAAC TACGGC T  C CATAT ACACGCCATGAT 151                                                200
AY150365       (151)  ATGCTGCA ATCCCT AACAGCA  AAA TGAAAAATA   AGT  CT A
EU668142       (151)  ATGCTGCAGATCCCTAAACAGCAGCAAAGTGAAAAATAC AGTG CTCA
L05081         (151)  ATGCTGCA ATCCCT AACAGCA  AAA TGAAAAATA   AGT  CT A
DQ095874       (151)  ATGCTGCA ATCCCT AACAGCA  AAA TGAAAAATA  GAGT  CT A
EF198106       (151)  ATGCTGCA ATCCCT AACAGCA  AAA TGAAAAATA A AGT  CT A
FJ437239       (151)  ATGCTGCA ATCCCT AACAGCA  AAA TGAAAAATA   AGTTTCT A
NC_000964      (151)  ATGCTGCA ATCCCT AACAGCA  AAA TGAAAAATA   AGT  CT A
sacB(SEQ 3)    (151)  ATGCTGCA ATCCCT AACAGCA  AAA TGAAAAATA   AGT  CT A 201                                                250
AY150365       (201)   TT GA  TC ACAATTAAAAATATC   TC GC AAAGG CTGGA G
EU668142       (201)   TTGACCCATCAACAATTAAAAATATCGAGTCCGCGAAAGGACTGGATG
L05081         (201)   TT GA  TC ACAATTAAAAATATC   TC GC AAAGG CTGGAGG
DQ095874       (201)   TT GA  TC ACAATTAAAAATATC   TC GC AAAGG CTGGA G
EF198106       (201)  GTT GA  TC ACAATTAAAAATATC   TC GC AAAGG CTGGA G
FJ437239       (201)   TTTGA  TT ACAATTAAAAATATC   TC GC AAAGG CTGGA G
NC_000964      (201)   TT GA  TC ACAATTAAAAATATC   TC GC AAAGG CTGGA G
sacB(SEQ 3)    (201)   TT GA  TT ACAATTAAAAATATC   TC GC AAAGG CTGGA G
```

```
                      501                                                550
AY150365     (501)    TAC TTACATCTGACGGAAAAATCCGTTTATTCTACACTGA TT TCCG
EU668142     (501)    AAGCTTACATCTGACGGAAAAATCCGTTTATTCTACACTGACTTTTCCG
L05081       (501)    AC TTACATCTGACGGAAAAATCCGTTTATTCTACACTGA TT TCCG
DQ095874     (501)    AC TTACATCTGACGGAAAAATCCGTTTATTCTACACTGA TT TCCG
EF198106     (501)    AC TTACATCTGACGGAAAAATCCGTTTATTCTACACTGA TT TCCG
FJ437239     (501)    AC TTACATCTGACGGAAAAATCCGTTTATTCTACACTGA TT TCCG
NC_000964    (501)    AC TTACATCTGACGGAAAAATCCGTTTATTCTACACTGA TT TCCG
sacB(SEQ 3)  (501)    AC TTACATCTGACGGAAAAATCCGTTTATTCTACACTGA TT TCCG 551                                                600
AY150365     (551)    GTAAACATTACGGCAAACAAA  TGACAAC GC CA GT AA GT  TCA
EU668142     (551)    GTAAACATTACGGCAAACAAAGCCTGACAACGGCGCAGCTAAATGTCTCA
L05081       (551)    GTAAACATTACGGCAAACAAA  TGACAAC GC CA GT AA GT  TCA
DQ095874     (551)    GTAAACATTACGGCAAACAAA  TGACAAC GC CA GT AA GT  TCA
EF198106     (551)    GTAAACATTACGGCAAACAAA  TGACAAC GC CA GT AA GT  TCA
FJ437239     (551)    GTAAACATTACGGCAAACAAA  TGACAAC GC CA GT AA GT  TCA
NC_000964    (551)    GTAAACATTACGGCAAACAAA  TGACAAC GC CA GT AA GT  TCA
sacB(SEQ 3)  (551)    GTAAACATTACGGCAAACAAA  TGACAAC GC CA GT AA GT  TCA 601                                                650
AY150365     (601)    A ATC GA  GC C  TGAA ATCAACGG  T GA GAT  ATAAA  AT
EU668142     (601)    AAATCTGATGACACGCTCAAGATCAACGGAGTGAAGATCATAAAACGAT
L05081       (601)      ATC GA  GC C  TGAA ATCAACGG  T GA GAT  ATAAA  AT
DQ095874     (601)      ATC GA  GC C  TGAA ATCAACGG  T GA GAT  ATAAA  AT
EF198106     (601)      ATC GA  GC C  TGAA ATCAACGG  T GA GAT  ATAAA  AT
FJ437239     (601)      ATC GA  GC C  TGAA ATCAACGG  T GA GAT  ATAAA  AT
NC_000964    (601)      ATC GA  GC C  TGAA ATCAACGG  T GA GAT  ATAAA  AT
sacB(SEQ 3)  (601)      ATC GA  GC C  TGAA ATCAACGG  T GA GAT  ATAAA  AT 651                                                700
AY150365     (651)     TTGACGGCGACGG CAAAAC TATCAAAA GT CAGCAGTT ATCGATC
EU668142     (651)    TTTGACGGCGACGG AAAACATATCAAAACGTTCAGCAGTTTATCGATC
L05081       (651)     TTGACGG GACGG AAAAC TATCAAAA GT CAGCAGTT ATCGATC
DQ095874     (651)     TTGACGG GACGG AAAAC TATCAAAA GT CAGCAGTT ATCGATC
EF198106     (651)     TTGACGG GACGG AAAAC TATCAAAA GT CAGCAGTT ATCGATC
FJ437239     (651)     TTGACGG GACGG AAAAC TATCAAAA GT CAGCAGTT ATCGATC
NC_000964    (651)     TTGACGG GACGG AAAAC TATCAAAA GT CAGCAGTT ATCGATC
sacB(SEQ 3)  (651)     TTGACGG GACGG AAAAC TATCAAAA GT CAGCAGTT ATCGAAG 701                                                750
AY150365     (701)    AAGG AACTA A  TC GGCGATAACCATACGCTGAGAGA CCTCACTAC
EU668142     (701)    AAGGGAACTATACATCGGCGA AACCATACGCTGAGAGACCCTCACTAC
L05081       (701)    AAGG AACTA A  TC GGCGA AACCATACGCTGAGAGA CCTCACTAC
DQ095874     (701)    AAGG AACTA A  TC GGCGA AACCATACGCTGAGAGA CCTCACTAC
EF198106     (701)    AAGG AACTA A  TC GGCGA AACCATACGCTGAGAGA CCTCACTAC
FJ437239     (701)    AAGG AACTA A  TC GGCGA AACCATACGCTGAGAGA CCTCACTAC
NC_000964    (701)    AAGG AACTA A  TC GGCGA AACCATACGCTGAGAGA CCTCACTAC
sacB(SEQ 3)  (701)    AAGG AACTA A  TC GGCGA AACCATACGCTGAGAGA CCTCACTAC
```

Figure 30D

```
              751                                                 800
AY150365    (751) GT GAAGA AAAGC CA AAATAC TT GTATT GAAGC AACAC GGAAC
EU668142    (751) GTTGAAGACAAAGCACATAAATACCTTGTATTCGAAGCCAACACGGGAAC
L05081      (751) GT GAAGA AAAGC CA AAATAC TT GTATT GAAGC AACAC GGAAC
DQ095874    (751) GT GAAGA AAAGC CA AAATAC TT GTATT GAAGC AACAC GGAAC
EF198106    (751) GT GAAGA AAAGC CA AAATAC TT GTATT GAAGC AACAC GGAAC
FJ437239    (751) GT GAAGA AAAGC CA AAATAC TT GTATT GAAGC AACAC GGAAC
NC_000964   (751) GT GAAGA AAAGC CA AAATAC TT GTATT GAAGC AACAC GGAAC
sacB(SEQ 3) (751) GT GAAGA AAAGC CA AAATAC TT GTATT GAAGC AACAC GGAAC 801                                                 850
AY150365    (801)  GAA  GG TACCAAGGCGAAGAATCTTTATTTAACAAAGC TACTA G
EU668142    (801) AGAAAACGGATACCAAGGCGAAGAATCTTTATTTAACAAAGCGTACTACG
L05081      (801)  GAA  GG TACCAAGGCGAAGAATCTTTATTTAACAAAGC TACTA G
DQ095874    (801)  GAA  GG TACCAAGGCGAAGAATCTTTATTTAACAAAGC TACTA G
EF198106    (801)  GAA  GG TACCAAGGCGAAGAATCTTTATTTAACAAAGC TACTA G
FJ437239    (801)  GAA  GG TACCAAGGCGAAGAATCTTTATTTAACAAAGC TACTA G
NC_000964   (801)  GAA  GG TACCAAGGCGAAGAATCTTTATTTAACAAAGC TACTA G
sacB(SEQ 3) (801)  GAA  GG TACCAAGGCGAAGAATCTTTATTTAACAAAGC TACTA G 851                                                 900
AY150365    (851) GC  AGCACA  TTCTTCCGT AAGAAAGTCA AA  CTTC GCAAAGC
EU668142    (851) GCGGCAGCACAAACTTCTTCCGTAAAGAAAGTCAGAAGCTTCAGCAAAGC
L05081      (851) GC  AGCACA  TTCTTCCGT AAGAAAGTCA AA  CTTC GCAAAGC
DQ095874    (851) GC  AGCACA  TTCTTCCGT AAGAAAGTCA AA  CTTC GCAAAGC
EF198106    (851) GC  AGCACA  TTCTTCCGT AAGAAAGTCA AA  CTTC GCAAAGC
FJ437239    (851) GC  AGCACA  TTCTTCCGT AAGAAAGTCA AA  CTTC GCAAAGC
NC_000964   (851) GC  AGCACA  TTCTTCCGT AAGAAAGTCA AA  CTTC GCAAAGC
sacB(SEQ 3) (851) GC  AGCACA  TTCTTCCGT AAGAAAGTCA AA  CTTC GCAAAGC 901                                                 950
AY150365    (901) G TAAAAAACGC  GCTGA TTAGC AACGGCGC CTCGGTATG T GA
EU668142    (901) GCTAAAAAACGCGGATCCTGAATTAGCGAACGGCGCCCTCGGTATGGTAGA
L05081      (901) G TAAAAAACGC  GCTGA TTAGC AACGGCGC CTCGGTATG T GA
DQ095874    (901) G TAAAAAACGC  GCTGA TTAGC AACGGCGC CTCGGTATG T GA
EF198106    (901) G TAAAAAACGC  GCTGA TTAGC AACGGCGC CTCGGTATG T GA
FJ437239    (901) G TAAAAAACGC  GCTGA TTAGC AACGGCGC CTCGGTATG T GA
NC_000964   (901) G TAAAAAACGC  GCTGA TTAGC AACGGCGC CTCGGTATG T GA
sacB(SEQ 3) (901) G TAAAAAACGC  GCTGA TTAGC AACGGCGC CTCGGTATG T GA 951                                                1000
AY150365    (951) G TAAACGATGA TACACA TGAAAAAAGT ATGAA CGCTGAT AC
EU668142    (951) GTTAAACGATGATTACACATTGAAAAAAGTCATGAAGCCGCTGATCACTT
L05081      (951) G TAAACGATGA TACACA TGAAAAAAGT ATGAA CGCTGAT GC
DQ095874    (951) G TAAACGATGA TACACA TGAAAAAAGT ATGAA CCGCTGAT  C
EF198106    (951) G TAAACGATGA TACACA TGAAAAAAGT ATGAA CGCTGAT  C
FJ437239    (951) G TAAACGATGA TACACA TGAAAAAAGT ATGAA CGCTGAT  C
NC_000964   (951) G TAAACGATGA TACACA TGAAAAAAGT ATGAA CGCTGAT  C
sacB(SEQ 3) (951) G TAAACGATGA TACACA TGAAAAAAGT ATGAA CGCTGAT  C
```

```
                  1251                                              1300
AY150365  (1251)  GCAAGCCAAAGCAAACAATGTCGTGATTACAAGCTATATGACAAACAGAG
EU668142  (1251)  GCAAGCCAAAGCAACAATGTCCTGATCACAAGCTACATGACAAACAGAG
L05081    (1251)  GCAAGCCAAAGCAAACAATGTCGTGATTACAAGCTATATGACAAACAGAG
DQ095874  (1251)  GCAAGCCAAAGCAAACAATGTCGTGATTACAAGCTATATGACAAACAGAG
EF198106  (1251)  GCAAGCCAAAGCAAACAATGTCGTGATTACAAGCTATATGACAAACAGAG
FJ437239  (1251)  GCAAGCCAAAGCAAACAATGTCGTGATTACAAGCTATATGACAAACAGAG
NC_000964 (1251)  GCAAGCCAAAGCAAACAATGTCGTGATTACAAGCTATATGACAAACAGAG
sacB(SEQ3)(1251)  GCAAGCCAAAGCAAACAATGTCGTGATTACAAGCTATATGACAAACAGAG 1301                                              1350
AY150365  (1301)  GATTCTACGGAGAAAACAATCAACGTTTGCACCAAGCTTCGTTCTGAAC
EU668142  (1301)  GCTTCTTTGAGGATAAAAAGCCCGACATTTGCGCCAAGCTTCTTAATGAAC
L05081    (1301)  GATTCTACGGAGAAAACAATCAACGTTTGCGCCAAGCTTCGTTCTGAAC
DQ095874  (1301)  GATTCTACGGAGAAAACAATCAACGTTTGCGCCAAGCTTCGTTCTGAAC
EF198106  (1301)  GATTCTACGGAGAAAACAATCAACGTTTGCGCCTAGCTTCGTTCTGAAC
FJ437239  (1301)  GATTCTACGGAGAAAACAATCAACGTTTGCGCCGAGCTTCGTTCTGAAC
NC_000964 (1301)  GATTCTACGGAGAAAACAATCAACGTTTGCGCCAAGCTTCGTTCTGAAC
sacB(SEQ3)(1301)  GATTCTACGGAGAAAACAATCAACGTTTGCGCCAAGCTTCGTTCTGAAC 1351                                              1400
AY150365  (1351)  ATCAAAGGCAAGAAAACATCGGTTGTGAAAACAGCATCCTTGAACAAGG
EU668142  (1351)  ATCAAAGGCAAGAAAACATCCGTTGTTAAAAACAGCATCCTTGAACAAGG
L05081    (1351)  ATCAAAGGCAAGAAAACATCGGTTGTGAAAACAGCATCCTTGAACAAGG
DQ095874  (1351)  ATCAAAGGCAAGAAAACATCGGTTGTGAAAACAGCATCCTTGAACAAGG
EF198106  (1351)  ATCAAAGGCAAGAAAACATCGGTTGTGAAAACAGCATCCTTGAACAAGG
FJ437239  (1351)  ATCAAAGGCAAGAAAACATCGGTTGTGAAAACAGCATCCTTGAACAAGG
NC_000964 (1351)  ATCAAAGGCAAGAAAACATCGGTTGTGAAAACAGCATCCTTGAACAAGG
sacB(SEQ3)(1351)  ATCAAAGGCAAGAAAACATCGGTTGTGAAAACAGCATCCTTGAACAAGG 1401        1422
AY150365  (1401)  ACAGCTTACGGTTAACCAATAA
EU668142  (1401)  ACAGCTTACGGTTAACAAC---
L05081    (1401)  ACAGCTTACGGTTAACAATAA
DQ095874  (1401)  ACAGCTTACGGTTAACAATAA
EF198106  (1401)  ACAGCTTACGGTTAACAATAA
FJ437239  (1401)  ACAGCTTACGGTTAACAATAA
NC_000964 (1401)  ACAGCTTACGGTTAACAATAA
sacB(SEQ3)(1401)  ACAGCTTACGGTTAACAATAA
```

|  | SacB gene (SEQ ID NO:3) (sequence identity) |
|---|---|
| AY150365 (SEQ ID NO:63) | 98.9% |
| EU668142 (SEQ ID NO:65) | 83.3% |
| L05081   (SEQ ID NO:61) | 99.9% |
| DQ095874 (SEQ ID NO:67) | 99.9% |
| EF198106 (SEQ ID NO:69) | 99.7% |
| FJ437239 (SEQ ID NO:71) | 99.8% |
| NC_000964(SEQ ID NO:73) | 100% |

Figure 31A

Lambda promoter λpR (SEQ ID NO:5) (driving SacB gene on chromosome)
TTGACTATTTTACCTCTGGCGGTGATAATG

P1 promoter 1 (SEQ ID NO:29)
GTGATACGCC TATTTTTATA GGTTAATGTC ATGAT

P1 promoter 2 (SEQ ID NO:83)
atcatgacattaacctataaaaataggcgtatcac

Native promoter cI (SEQ ID NO:30)
GGTGTTAGATATTTATCCCTTGCGGTGATAGATTTAACGT

Lambda promoter λpR + 5' UTR + sacB gene (SEQ ID NO:75)
```
TTGACTATTTTACCTCTGGCGGTGATAATGGTTGCATGTACTAAGGAGGTTGTATGGAACAACGCATAACCCTGAAAGATTATGCAATGCGCTTTGC
GCAAACCAAGACAGCTAAAGATCACTTAAATCGACCAGTAACAGGTTGGCCTTTTGAACAGGGATCACATGGATATGAACATCAAAAAGTTTGCAAAAC
AAGCAACAGTATTAACCTTTACTACCGCACTGCTGGCAGGAGGCGCAACTCAAGCGTTTGCGAAAGAAACGAACCAAAAGCCATATAAGGAAACATA
CCCGCATTTCCCCATATTACACCCCATGATATGCTGCAAATCCCTGAACAGCCAAAAAAATGAAAAATATCAAGTTCCTCAATTCGATTCGTCCACAATT
AAAAAATATCTCTTCTGCAAAAGGCCTGGACGTTTGGGACAGCTGGCCATTACAAAACGCTGACGGCACTGTCGCAAACTATCACGGCTACCACATCG
TCTTTGCATTAGCCGGAGATCCTAAAAATCCGGATGACACATCGATTTACATGTTCTATCAAAAAGTCGGCGAAACTTCTATTGACAGCTGGAAAAA
CCCTGGCCGCCTCTTAAAGACAGGGACAAATTCGATGCAAATGATTCTATCCTAAAAGACCAAACACAAGAATGGTCAGGTTCAGCCACATTTACA
TCTGACGGAAAAATCCGTTTATTCTACACTGATTTCTCCGGTAAACATTACGGCAAACAAACACTGACAACTGCACAAGTTAACGTATCAGCATCAG
ACAGCTCTTTGAACATCAACGGTGTGAGAGGATTATAAATCAATCTTTGACCGTTGACGGAAAAACGTATCAAAATGTACAGCAGTTCATCGATGAAGG
CAACTACAGCTCAGGCGACAACCATACGCTGAGAGATCCTCACTACGTAGAAGATAAAGGCCACAAATACTTAGTATTTGAAGCAAACACTGGAACT
GAAGATGGCTACCAAGGCGAAGAATCTTTATTTAACAAAGCATACTATGGCAAAAGCACATCATTCTTCCCGTCAAGAAAGTCAAAAACTTCTGCAAA
GCGATAAAAAACGCACGGCTGAGTTAGCAAACGGCGCTCTCGGTATGATTGAGCTAAACGATGATTACACACTGAAAAAAGTGATGAAACCGCTGAT
TGCATCTAACACAGTAACAGATGAAATTGAACGCGCGAACGTCTTTAAAATGAACGGCAAATGGTACCTGTTCACTGACTCCCGGGGATCAAAAATG
ACGATTGACGGCATTACGTCTAACGATATTTACATGCTTGGTTATGTTTCTAATTCTTTAACTGGCCCATACAAGCCGCTGAACAAAACTGGCCTTG
TGTTAAAAATGGATCCTGAACCTAACGATGTAACCTTTACTTACTCACACTTCGCTGTACCTCAAGCGAAAGGAAACAATGTCGTGATTACAAGCTA
TATGACAAACAGAGGATTCTACGCAGACAAACAATCAACGTTTGCGCCAAGCTTCCTGCTGAACATCAAAGGCAAGAAAACATCTGTTGTCAAAGAC
AGCATCCTTGAACAAGGACAATTAACAGTTAACAAATAA
```

P1 promoter + cI gene in pPB829 and pPB838 (SEQ ID NO:76)
```
  1 GTGATACGCC TATTTTTATA GGTTAATGTC ATGATAATAA TGGTTTCTTA GACGTCAGGT
 61 GGCACTTTTC GGGGAAATGT GCGCGGAACC CCATTTAAAT TGTCTGCTTA CATAAACAGT
121 AATACAAGGG GTGTTATGAG CACAAAAAAG AAACCATTAA CACAAGAGCA GCTTGAGGAC
181 GCACGTCGCC TTAAAGCAAT TTATGAAAAA AAGAAAAATG AACTGGCTT ATCCCAGGAA
241 TCTGTCGCAG ACAAGATGGG GATGGGGCAG TCAGGCGTTG GTGCTTTATT TAATGGCATC
301 AATGCATTAA ATGCTTATAA CGCCGCATTG CTTACAAAAA TTCTCAAAGT TAGCGTTGAA
361 GAATTAGCC CTTCAATCGC CAGAGAAATC TACGAGATGT ATGAAGCGGT TAGTATGCAG
421 CCGTCACTTA GAAGTGAGTA TGAGTACCCT GTTTTTTCTC ATGTTCAGGC AGGGATGTTC
481 TCACCTAAGC TTAGAACCTT TACCAAAGGT GATGCGGAGA GATGGGTAAG CACAACCAAA
541 AAAGCCAGTG ATTCTGCATT CTGGCTTGAG GTTGAAGGTA ATTCCATGAC CGCACCAACA
601 GGCTCCAAGC CAAGCTTTCC TGACGGAATG TTAATTCTCG TTGACCCTGA GCAGGCTGTT
661 GAGCCAGGTG ATTTCTGCAT AGCCAGACTT GGGGGTGATG AGTTTACCTT CAAGAAACTG
721 ATCAGGGATA GCGGTCAGGT GTTTTTACAA CCACTAAACC CACAGTACCC AATGATCCCA
781 TGCAATGAGA GTTGTTCCGT TGTGGGGAAA GTTATCGCTA GTCAGTGGCC TGAAGAGACG
841 TTTGGCTGA
```

Figure 31B cI native promoter + cI gene in pPB846 and pPB847  (SEQ ID NO:77)
```
GGTGTTAGATATTTATCCCTTGCGGTGATAGATTTAACGT ATG AGCACAAAAA AGAAACCATT AACACAAGAG CAGCTTGAGG
ACGCACGTCG CCTTAAAGCA ATTTATGAAA AAAAGAAAAA TGAACTTGGC TTATCCCAGG AATCTGTCGC AGACAAGATG
GGGATGGGGC AGTCAGGCGT TGGTGCTTTA TTTAATGGCA TCAATGCATT AAATGCTTAT AACGCCGCAT TGCTTACAAA
AATTCTCAAA GTTAGCGTTG AAGAATTTAG CCCTTCAATC GCCAGAGAAA TCTACGAGAT GTATGAAGCG
GTTAGTATGC AGCCGTCACT TAGAAGTGAG TATGAGTACC CTGTTTTTTC TCATGTTCAG GCAGGGATGT
TCTCACCTAA GCTTAGAACC TTTACCAAAG GTGATGCGGA GAGATGGGTA AGCACAACCA AAAAAGCCAG
TGATTCTGCA TTCTGGCTTG AGGTTGAAGG TAATTCCATG ACCGCACCAA CAGGCTCCAA GCCAAGCTTT
CCTGACGGAA TGTTAATTCT CGTTGACCCT GAGCAGGCTG TTGAGCCAGG TGATTCTGC ATAGCCAGAC
TTGCGCGTGA TCAGTTTACC TTCAAGAAAC TGATCACCGA TACCGGTCAG GTGTTTTTAC AACCACTAAA
CCCACAGTAC CCAATGATCC CATGCAATGA GAGTTGTTCC GTTGTGGGGA AAGTTATCGC TAGTCAGTGG
CCTGAAGAGA CGTTTGGC
```

ANTIBIOTIC-FREE PLASMIDS

INCORPORATION BY REFERENCE

This application claims benefit of U.S. provisional application Ser. No. 61/180,755 filed May 22, 2009.

FIELD OF THE INVENTION

The present invention relates to a method of maintaining and producing plasmids in a gram negative bacterium without the use of antibiotic selection pressure. Further, the invention relates to the drugless plasmids produced as well as formulations and/or compositions containing the drugless plasmids, and formulations and/or compositions containing the protein or immunogen produced using the drugless plasmids, and to methods of administering the formulations and/or compositions to a host. The invention relates to gram negative bacteria containing the drugless plasmids.

BACKGROUND OF THE INVENTION

To date, there is an absence of plasmid DNA vectors that are considered safe, potent, and efficient for medicinal use. The presence of antibiotic resistance genes in the delivered plasmids is one of the drawbacks of modern gene therapy and DNA vaccine applications.

Plasmids are extra-chromosomal DNA molecules that are separate from the chromosomal DNA and are capable of replicating independently of the chromosomal DNA (Lipps G. (editor). (2008). Plasmids: Current Research and Future Trends. Caister Academic Press. ISBN 978-1-904455-35-6). Plasmids usually occur naturally in bacteria, but are sometimes found in eukaryotic organisms. They are considered transferable genetic elements, or replicons, capable of autonomous replication within a suitable host. Plasmids are naked DNA and do not encode genes necessary to encase the genetic material for transfer to a new host. Therefore host-to-host transfer of plasmids requires direct, mechanical transfer by conjugation or changes in host gene expression allowing the intentional uptake of the genetic element by transformation (Lipps G. 2008).

The use of plasmid DNA (pDNA) for gene therapy and vaccination is a novel technology with considerable potential in human and animal health care (Mairhofer, J. et al., Biotechnol. J., 3, 83-89, 2008). In addition, plasmids serve as important tools in genetics and biotechnology labs, where they are commonly used to multiply or express particular genes (Russell, David W.; Sambrook, Joseph (2001), Molecular cloning: a laboratory manual. Cold Spring Harbor, N.Y: Cold Spring Harbor Laboratory).

Plasmids provide a mechanism for horizontal gene transfer within a population of microbes and typically provide a selective advantage under a given environmental state. For example, plasmids may carry genes that provide resistance to naturally occurring antibiotics. Alternative markers besides antibiotics also exist. For example, the proteins produced by the plasmid may act as toxins which also provide a selective advantage under a given environmental state. Plasmids also can provide bacteria with an ability to fix elemental nitrogen or to degrade recalcitrant organic compounds which provide an advantage under conditions of nutrient deprivation (Lipps G., 2008).

For selection using antibiotic resistant genes, plasmids are prepared wherein a gene is inserted that generates a protein which makes cells resistant to a particular antibiotic. Next, the plasmids are inserted into bacteria by a process called transformation. Then, the bacteria are exposed to the particular antibiotics. Only bacteria which take up copies of the plasmid survive the antibiotic, since the plasmid makes them resistant.

Genes of interest may be delivered using a plasmid containing an antibiotic-resistant marker. Such a gene is typically inserted at a multiple cloning site (MCS, or polylinker). The antibiotic-resistant genes are expressed and the expressed proteins break down the antibiotics. In this way the antibiotics act as a filter to select only the modified bacteria. Now these bacteria can be grown in large amounts, harvested and lysed (often/using the alkaline lysis method) to isolate the plasmid of interest.

The very success of antibiotics in medicine has now become a problem. Many bacteria, including pathogens of infectious diseases, are already resistant and can no longer be controlled with the particular antibiotic. Antibiotics have been used too frequently in human and animal medicine. Moreover, of even far greater significance is the fact that for a long time they were added to animal feed as a performance enhancer. This practice is now largely outlawed, but the pervasive antibiotics have given a survival advantage to those bacteria that have a corresponding resistance gene. Moreover, resistance genes in bacteria are often located on mobile DNA units, which can be exchanged between different species.

Against this background there is concern that bacteria could absorb marker genes eventually resulting in pathogens, against which antibiotics currently being prescribed are ineffective. There might be a gene transfer to environmental microorganisms, e.g., pathogens (Murphy, D. B., Epstein, S. L., Guidance for Industry: Guidance for human somatic cell therapy and gene therapy, Food and Drug Administration, Rockville 1998). Another safety concern is the possible integration of the antibiotic resistance gene into the human chromosome (Smith, H. A., Klinman, D. M., Curr. Opin. Biotechnol. 12, 299-203, 2001). Further, such genes may have a considerable impact on the plasmid production process, as constitutive expression of these genes imposes an unnecessary metabolic load on the bacterial host cell (Cranenburgh, R. M., et al., Nucleic Acids Res. 2001, 29, e26; Rozkov, A., et al., Enzyme Microb. Technol. 2006, 39, 47-50). Reducing the size of the plasmids by eliminating these genes would lead to improved stability and yield of pDNA obtained by the fermentation process (Smith, M. A., et al., Can. J. Microbiol. 1998, 44, 351-355).

Therefore, there is an absolute need in the art to avoid the use of antibiotic resistance genes in the final (commercial) product (naked DNA vaccine) as there is a potential acceptance risk by the public/consumers following current recommendations from regulatory authorities. The Food and Drug Administration (FDA) and the World Health Organization (WHO) regulate the use of antibiotic resistance markers to assure the quality of DNA vaccines and to prevent infectious diseases. Similarly, the EU Deliberate Release Directive, which has been in effect since 2002, requires "the phasing out of the use of antibiotic-resistance markers in genetically modified organisms which may have a harmful impact on human health or the environment".

The drawbacks of traditional markers are becoming apparent even in practical research. For example, there is a need to have an antibiotic-free delivery system for the commercial applications of bactofection technology. Bactofection technology is the delivery of plasmid DNA into eukaryotic cells using invasive bacteria. Moreover, there exists a technical need to reduce unnecessary metabolic burdens during the fermentation process, which will achieve higher ODs and higher yields in DNA plasmid.

Alternative selection strategies have been designed to address concerns regarding dissemination of antibiotic resistance genes to a patient's enteric bacteria including auxotrophy complementation, repressor titration, protein based antidote/poison selection schemes, and the use of RNA based selectable markers (see Williams J. A. et al., Plasmid DNA vaccine vector design: Impact on efficacy, safety and upstream production, Biotechnol Adv (2009), doi:10.1016/j.biotechadv.1009.02.003).

Cranenburgh, R. M. et al. reported the construction of two novel *Escherichia coli* strains (DH1lacdapD and DH1lacP2dapD) that facilitate the antibiotic-free selection and stable maintenance of recombinant plasmids in complex media. They contain the essential chromosomal gene, dapD, under the control of the lac operator/promoter (Cranenburgh, R. M., et al., 2001). Unless supplemented with IPTG (which induces expression of dapD) or DAP, these cells lyse, however, when the strains are transformed with a multicopy plasmid containing the lac operator, the operator competitively titrates the LacI repressor and allows expression of dapD from the lac promoter. Thus transformants can be isolated and propagated simply by their ability to grow on any medium by repressor titration selection. No antibiotic resistance genes or other protein expressing sequences are required on the plasmid, and antibiotics are not necessary for plasmid selection.

Mairhofer et al. recently investigated designing bacterial host strains that serve to select and maintain plasmids without the use of any selection marker or other additional sequence on the plasmid. Several bacterial strains were modified, so that the plasmid's replicational inhibitor RNA I could suppress the translation of a growth essential gene by RNA-RNA antisense reaction (Mairhofer, J. et al., Biotechnol. J., 3, 83-89, 2008). An essential gene (murA) was modified such that a repressor protein (tetR) would hamper its expression (Mairhofer, J. et al., 2008). Only in the presence of plasmid and, hence, RNA I, was tetR turned down and murA expressed. The authors reported that different commercially available plasmids could be selected by various modified *Escherichia coli* strains. They further designed a minimalistic plasmid devoid of any selection marker.

Citation or identification of any document in this application is not an admission that such document is available as prior art to the present invention.

SUMMARY OF THE INVENTION

Antibiotic-free plasmids as well as gram-negative bacteria comprising the antibiotic-free plasmids are provided. Compositions comprising the antibiotic-free plasmids comprising a heterologous gene encoding an immunogen or a protein and compositions comprising the immunogen or the protein expressed using the antibiotic-free plasmids are also provided. The gram-negative bacteria are engineered to contain one or more heterologous polynucleotide in the nonessential region of the bacterial chromosome. The antibiotic-free plasmids comprise a polynucleotide encoding a repressor which regulates the expression of the heterologous polynucleotide on the bacterial chromosome. The antibiotic-free plasmids may further comprise one or more polynucleotide encoding an immunogen or a protein.

Methods of the invention include methods of producing antibiotic-free plasmids and methods for transfer of foreign genes into mammalian cells using the antibiotic-free plasmids.

These and other embodiments are disclosed or are obvious from and encompassed by, the following Detailed Description.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 6A provides an overview; FIG. 6B illustrates that the ΔpurN (or ΔedA) parental strain is resistant to kanmaycin and expresses constitutively SacB$^+$ conferring its sensitivity to sucrose when the cells are incubated at 30° C.-37° C. When the ΔpurN (or ΔedA) parental strain are transformed with either the pPB829 or pPB838 plasmids, these cells gain the ability to survive and grow in the presence of sucrose when incubated at 30-37° C.; FIG. 6C illustrates that the ΔpurN (or ΔedA) parental strain transformed with either the pPB829 or pPB838 plasmids (cI plasmids) is able to grow in LB medium containing either kanamycin, sucrose or chloramphenicol as well. The switch of temperature from 30-37° C. to 42° C. leads to the cell death when plated in the presence of sucrose.

FIGS. 8A and 8B illustrate the generation of the λPr::sacB Ωkan cassette to be inserted by allelic replacement of edA or purN gene, respectively, into the E. coli chromosome. FIG. 8C illustrates the engineering of the full sacB cassette (ΔpurN-ΩλPr::sacB cat) by PCR and joining PCR used for the allelic replacement of the edA gene into the ΔpurNΩλPr::sacB Km E. coli host strain for the generation of the double sacB cassette E. coli strain.

FIG. 9A illustrates in part the two PCR products (respectively 151 and 729 bp) that were purified and used as a template in a second PCR step with the PB1186 and PB1189 primers and the Phusion DNA polymerase. FIG. 9B illustrates the PCR check showing that the λPr::sacB$^+$ΩKan cassette is introduced into the chromosome of E. coli. FIG. 9C illustrates that the λPr::sacB$^+$ΩKan cassette is correctly inserted at the locus by allelic replacement of either edA and/or purN gene(s). As shown in FIG. 9D: Lanes 1: BJ5183 wt; 2: BJ5138 ΔpurN; 3: BJ5138 ΔedA; 4: BJ5183 ΔpurN ΔedA not diluted 1 μl; 5: BJ5183 ΔpurN ΔedA diluted 1/10; 6: Water, 0 by (control); A: BJ5183 wt; B: BJ5138 ΔpurN; C: BJ5138 ΔedA; D: BJ5183 ΔpurN ΔedA not diluted 3 μl; E: BJ5183 ΔpurN ΔedA not diluted 1 μl; F: BJ5183 ΔpurN ΔedA diluted 1/10; G: BJ5183 ΔpurN ΔedA diluted 1/50; H: Water, 0 by (control).

FIGS. 10B-C demonstrate that the dual sacB cassettes E. coli strain (ΔpurN λPr::sacB$^+$Ωkan ΔedA λPr::sacB$^+$ΩCat) is highly sensitive (no growth) in the presence of sucrose when incubated at 30° C. and 42° C. while some spontaneous mutants appear with the one sacB cassette E. coli strain plated on sucrose. FIG. 10C also demonstrates the lowest sucrose concentration required for the dual sacB cassettes E. coli strain compared to the one sacB cassette E. coli strain (from 10% to 2% final).

FIGS. 12B-C demonstrate that the presence of two sacB cassettes (rather than one) confers a better robustness to sucrose sensitivity (still optimal at 2% sucrose) at temperatures ranging from 30° C. to 37° C. The presence of one sacB cassette on the E. coli chromosome was less robust at sucrose concentration ranging from 2% to 4% at similar temperatures. As confirmed in this plating assay, the mutation rate to sucrose with the two sacB cassettes E. coli strain was undetectable at the lowest sucrose concentration (2%) when incubated at 37° C. while the mutation rate with the one sacB cassette E. coli strain was ranging from 3.8×10$^{-6}$ to 5×10$^{-5}$. An independent set of experiment showed that the mutation rate in the two sacB cassettes E. coli strain was nearly 5×10$^{-10}$ when incubated at 37° C. in the presence of 2% sucrose.

FIGS. 13A-B show the experimental procedures to enable the screening of the transformed cells by the chloramphenicol (Cat) marked cI plasmids without the use of antibiotic as selection pressure on agar plates.

FIGS. 14A-C illustrate the efficacy of the experimental procedure to select transformed cells with the cI plasmid only (pPB829 and pPB838) without the use of antibiotic as selection pressure.

FIG. 15F illustrates the plasmid transfection efficacy (GFP expression) in CHO cells of the antibiotic-free plasmid (pPB896/Sucrose as selection pressure) and antibiotic plasmid (pCG105/Cat as selection pressure). No obvious difference is observed in terms of expressed GFP protein between these two selection pressure (Sucrose versus Cat as antibiotic).

FIG. 26 shows the sequence alignment of cI repressor proteins and sequence identity percentage.

Figure 27A:
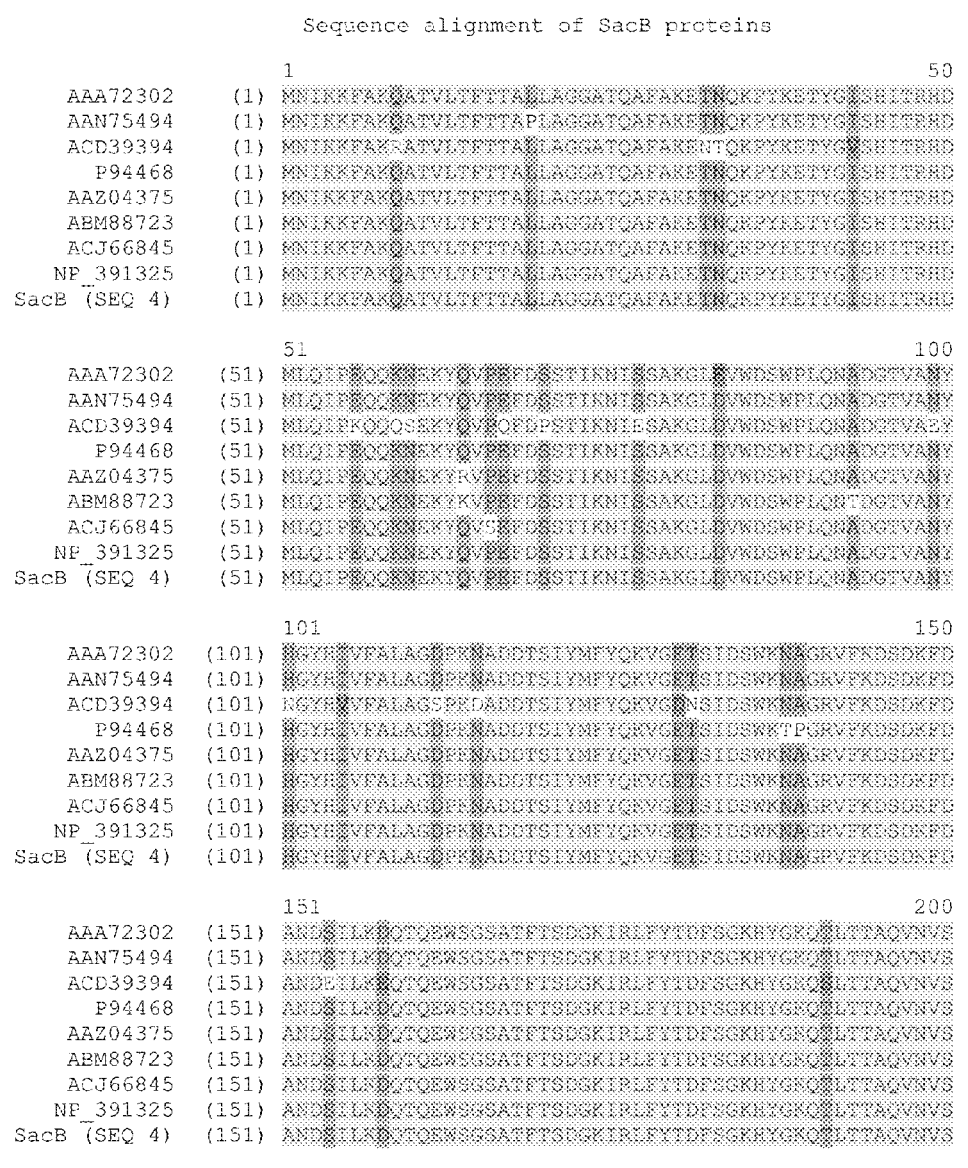

FIG. 27 shows the sequence alignment of sacB proteins and sequence identity percentage.

FIG. 28 is a table showing the SEQ ID NO assigned to the polynucleotide and protein.

Figure 29C:
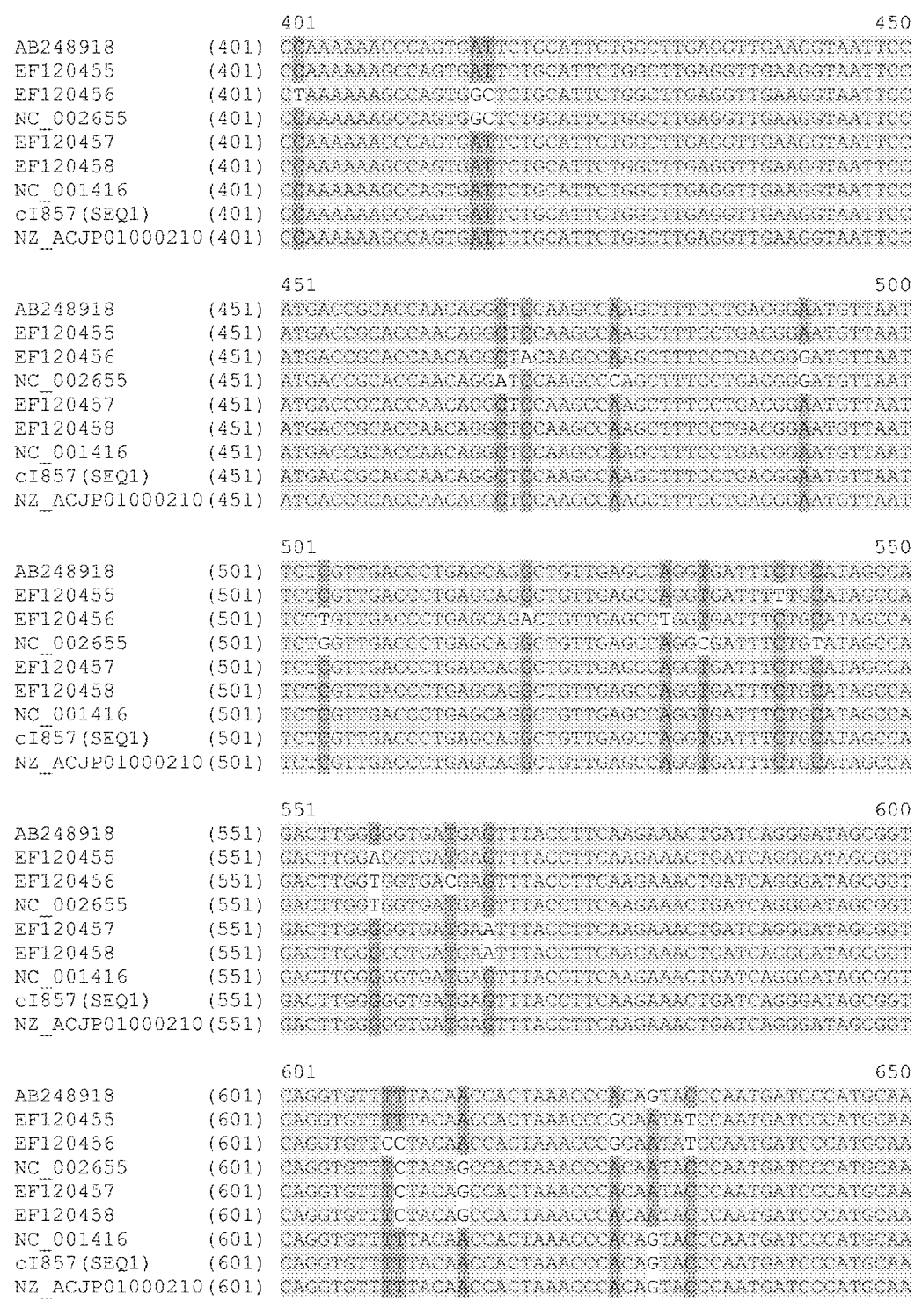

FIG. 29 shows the sequence alignment of the polynucleotides encoding cI repressor proteins and sequence identity percentage at the nucleotide level.

Figure 30B:
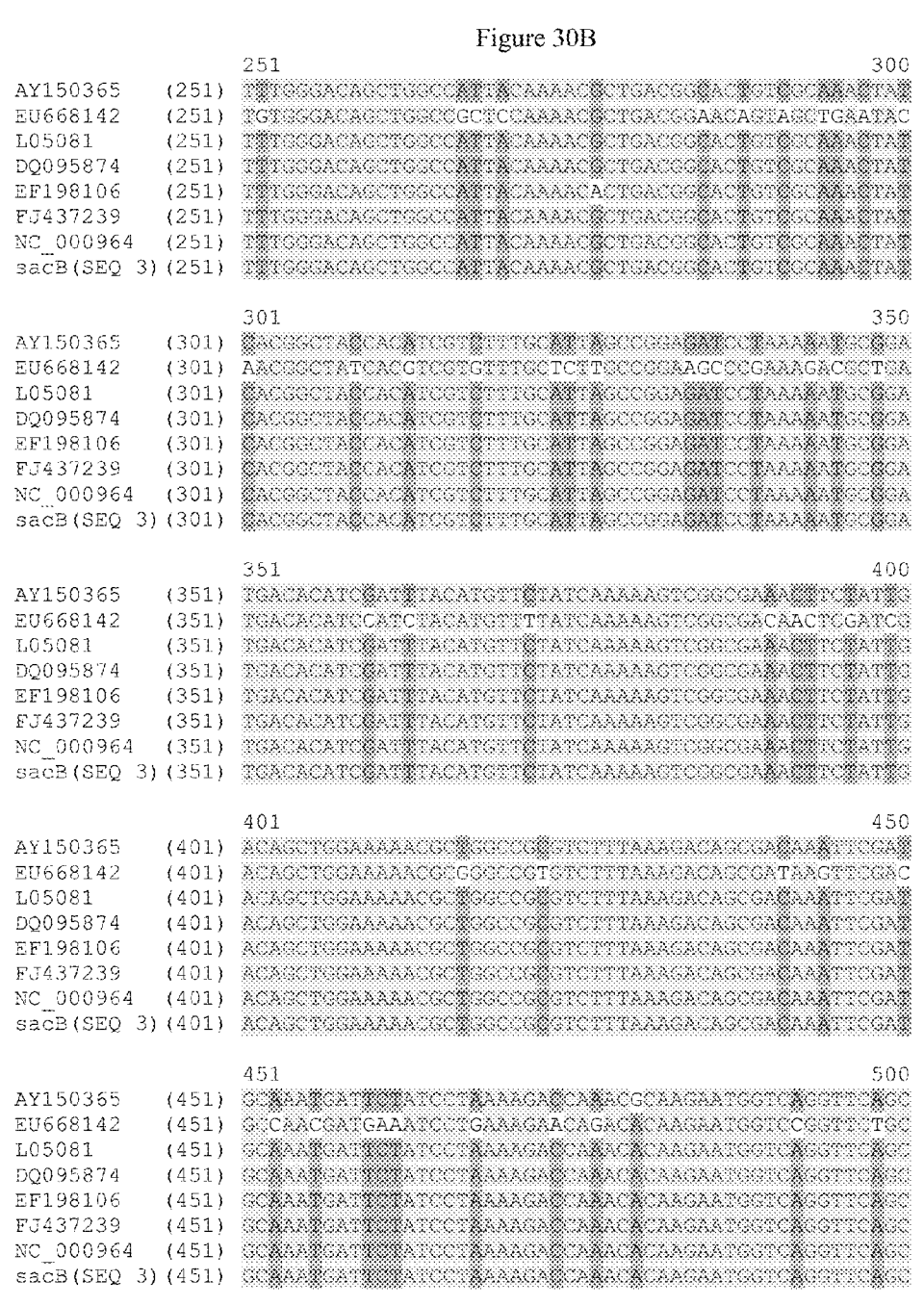
Figure 30E:
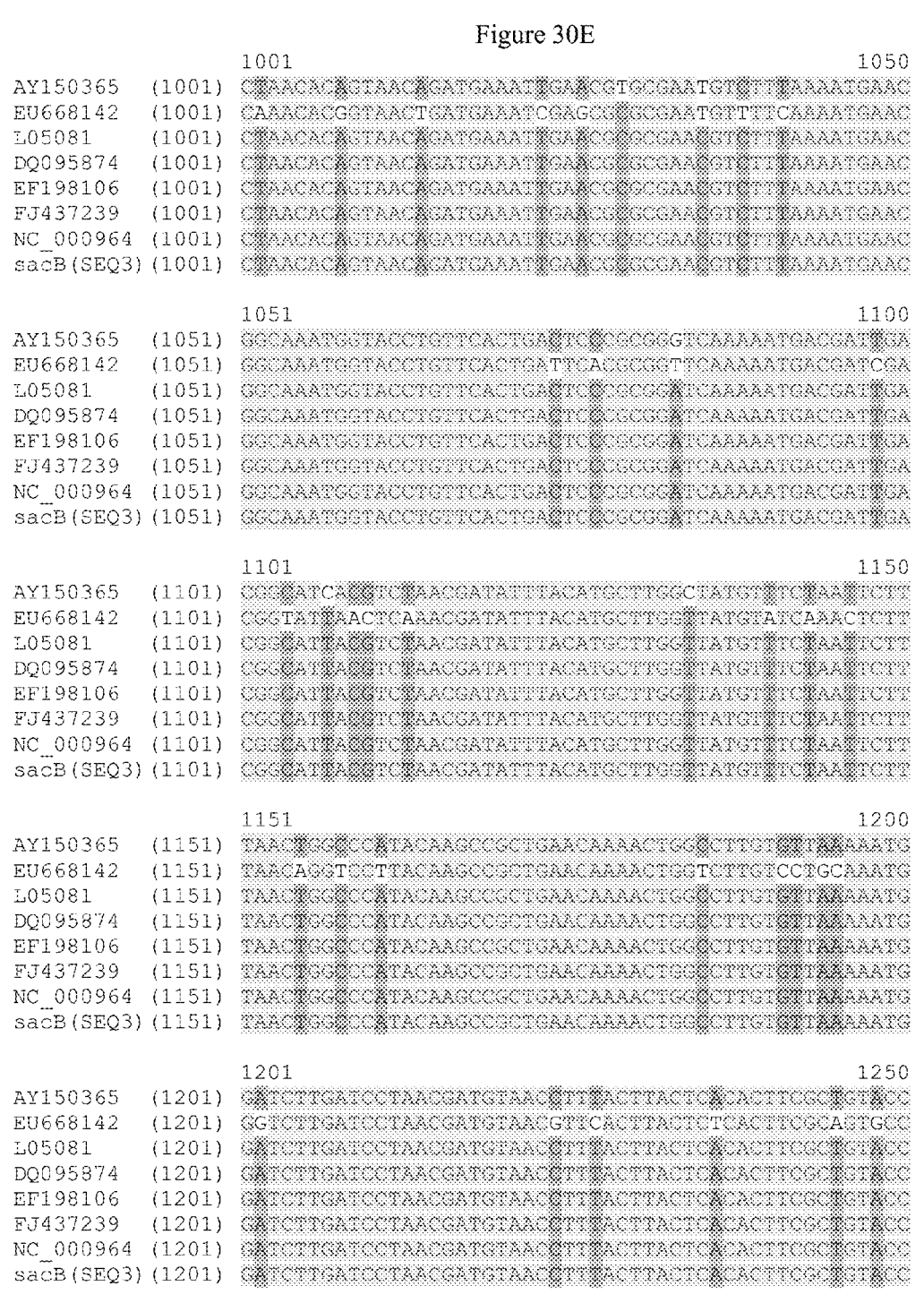

FIG. 30 shows the sequence alignment of the polynucleotides encoding sacB proteins and sequence identity percentage at the nucleotide level.

FIG. 31 shows the sequences for P1 promoter, cI native promoter, λPr promoter, λPr promoter+5' UTR+sacB gene, P1 promoter+cI gene, and cI native promoter+cI gene.

DETAILED DESCRIPTION

Figure 1:
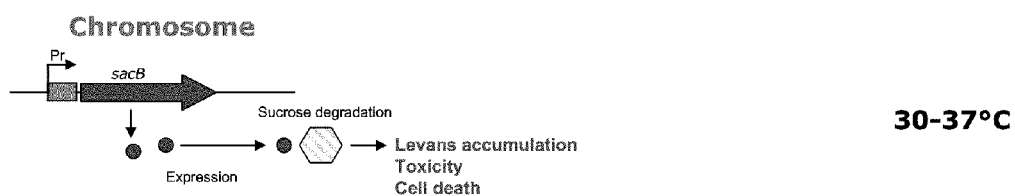
FIG. 1 describes the first component of the drugless concept which is the cloning of the sacB gene coding for levansucrase in gram-negative bacteria that leads to the rapid death of the transformed bacteria when plated on a medium containing sucrose.

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

By "animal" is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "nucleic acid" or "polynucleotide" is used interchangeably and refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "drugless plasmid" or "antibiotic-free plasmid" is used interchangeably and refers to a DNA plasmid which does not contain an antibiotic selection gene.

The term "gene" is used broadly to refer to any segment of polynucleotide associated with a biological function. Thus, genes include introns and exons as in genomic sequence, or just the coding sequences as in cDNAs and/or the regulatory sequences required for their expression.

For example, gene also refers to a nucleic acid fragment that expresses mRNA or functional RNA, or encodes a specific protein, and which includes regulatory sequences.

The subject matter disclosed herein relates to a novel approach to generating bacterial plasmid DNA vectors by circumventing the use of antibiotic resistance genes to produce safer vaccines and immunogenic compositions.

The subject matter disclosed herein demonstrates a new concept for maintaining a high number of plasmid copies within a gram negative bacterium host cell which is based on three components. The first component is a gram negative bacterium host which expresses a toxic product for the bacterium under defined culture conditions wherein the toxic gene is inserted into a non-essential region of the bacterium chromosome. The second component is the presence of a gene on the gram negative bacterium chromosome wherein the gene encodes a toxic product under the control of a constitutive promoter that can be tightly regulated. The third component is the expression of a specific repressor from a plasmid that regulates the promoter operably linked to the toxic gene on the host chromosome.

The gram negative bacteria contemplated in the present invention include, but are not limited to, *Avibacterium, Brucella, Escherichia coli, Haemophilus* (e.g., *Haemophilus suis*), *Salmonella* (e.g., *Salmonella enteridis, Salmonella typhimurium, Salmonella infantis*), *Shigella, Pasteurella*, and *Rimeirella*.

In one embodiment, the toxic gene is a structural sacB gene that encodes levansucrase. In another embodiment, the toxic gene is a structural sacB gene of *Bacillus subtilis* which encodes the *Bacillus subtilis* levansucrase. Expression of sacB in its natural environment is harmless to gram positive bacterium but when expressed in gram negative bacterium, it leads to rapid death of the transformed bacterium when they are plated on a medium containing sucrose.

In one aspect, the present invention provides a sacB protein (levansucrase). In another aspect, the present invention provides a sacB protein having a sequence as set forth in SEQ ID NO:4, 60, 62, 64, 66, 68, 70, 72 or 74, and variant or fragment thereof. In yet another aspect, the present invention provides a sacB protein having at least 70%, at least 75%, at least 80%, at least 85%, at least 90%, at least 95%, 96%, 97%, 98% or 99% sequence identity to a polypeptide having a sequence as set forth in SEQ ID NO:4, 60, 62, 64, 66, 68, 70, 72 or 74. In yet another aspect, the present invention provides fragments and variants of the sacB protein identified above (SEQ ID NO:4, 60, 62, 64, 66, 68, 70, 72 or 74) which may readily be prepared by one of skill in the art using well-known molecular biology techniques. Variants are homologous polypeptides having an amino acid sequence at least about 75%, 80%, 85%, 90%, 95%, 96%, 97%, 98%, or 99% identity to the polypeptides of the invention, particularly to the amino acid sequence as set forth in SEQ ID NO:4, 60, 62, 64, 66, 68, 70, 72 or 74.

In another aspect, the present invention provides a polynucleotide, such as a sacB gene, encoding a sacB protein (levansucrase), for example, a polynucleotide encoding a sacB protein having a sequence as set forth in SEQ ID NO:4, 60, 62, 64, 66, 68, 70, 72 or 74. In yet another aspect, the present invention provides a polynucleotide encoding a sacB protein having at least 70%, at least 75%, at least 80%, at least 85%, at least 90%, at least 95%, 96%, 97%, 98% or 99% sequence identity to a polypeptide having a sequence as set forth in SEQ ID NO:4, 60, 62, 64, 66, 68, 70, 72 or 74, or a conservative variant, an allelic variant, a homolog or a fragment comprising at least eight or at east ten consecutive amino acids of one of these polypeptides, or a combination of these polypeptides. In another aspect, the present invention provides a polynucleotide having a nucleotide sequence as set forth in SEQ ID NO:3, 61, 63, 65, 67, 69, 71, or 73, or a variant thereof. In yet another aspect, the present invention provides a polynucleotide having at least 70%, at least 75%, at least 80%, at least 85%, at least 90%, at least 95%, 96%, 97%, 98% or 99% sequence identity to one of a polynucleotide having a sequence as set forth in SEQ ID NO:3, 61, 63, 65, 67, 69, 71, or 73, or a variant thereof.

Other toxic genes which may be utilized in the present invention include, but are not limited to, *Listeria* or *Staphylococcus* genes. A toxic gene can be a DNA that is expressed as a toxic gene product (a toxic protein or RNA), or can be toxic in and of itself. Examples of such toxic gene products are well known in the art, and include, but are not limited to, restriction endonucleases (e.g., DpnI), CcdA/CcdB (Maki S. et al. J. Mol. Biol. 256: 473-482, 1996) and genes that kill hosts in the absence of a suppressing function, e.g. kicB. A toxic gene can alternatively be selectable in vitro, e.g., a restriction site.

As used herein, the term "homologs" includes orthologs, analogs and paralogs. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type polypeptide or polynucleotide sequences, and will exhibit a similar function.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of gene of interest, are intended to be within the scope of the invention.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for the polypeptides of the present invention, the DNA sequence of the polypeptide can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of the polypeptide of the present invention, such as a sacB protein or a cI repressor protein, in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the polypeptide encoded by the nucleotide sequence is functionally unchanged.

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences. The sequence identity or sequence similarity of two amino acid sequences, or the sequence identity between two nucleotide sequences can be determined using Vector NTI software package (Invitrogen, 1600 Faraday Ave., Carlsbad, Calif.).

In another embodiment, the promoter which is operably linked to the toxic gene of the present invention is a promoter from λ phage. λ phage is a temperate phage that lives in *E. coli*. Once the phage is inside its host, it may integrate itself into the host's DNA. In this state, λ is called a prophage and stays resident within the host's genome, without causing much harm to the host. This way, the prophage gets duplicated with every cell division of the host. The DNA of the prophage that is expressed in this state codes for proteins that look out for signs of stress in the host cell. Stress can be a result of starvation, poisons (like antibiotics), and other factors that can damage or destroy the host. When the stress condition is detected, the prophage becomes active again, excises itself from the DNA of the host cell and enters its lytic cycle. The reactivated phage takes apart the host's DNA and reprograms its protein factory to produce new phages in multiple copies. When all resources of the host are depleted from building new phages, the cell is lysed (the cell membrane is broken down), and the new phages are released.

The lambda repressor gene system consists of (from left to right on the chromosome): cI gene, OR3, OR2, OR1, cro gene. cI gene codes for the λ repressor ("the cI repressor protein"). The region of the genome that codes for the cI repressor protein is known as the immunity region. The cI repressor protein is both a positive and a negative regulator of gene transcription. It allows the phage λ to stay "latent" on the chromosome of its host bacterium. The lysogenic state of the λ bacteriophage is maintained by binding of regulatory protein cI to the OR (right operator) and OL (left operator) operators from λPl and λPr promoters, respectively, preventing transcription of the proteins necessary for the lytic stage. Bacterial cells harboring a lysogenic λ phage are immune to further infection by λ phage. The cI repressor protein inhibits the lytic development of any additional infecting phage particles.

In one aspect of the embodiment, the promoter comprises a polynucleotide having a sequence as set forth in SEQ ID NO:5. In another aspect, the promoter comprises a polynucleotide having at least 70%, at least 75%, at least 80%, at least 85%, at least 90%, at least 95%, 96%, 97%, 98% or 99% sequence identity to a polynucleotide having a sequence as set forth in SEQ ID NO:5.

In one embodiment, the repressor protein of the present invention is a cI repressor protein, such as the cI857 repressor which is temperature sensitive. A λ phage carrying cI857 as a lysogen will grow at temperatures below 39° C. but will then induce lytic growth by an increase in temperature. At 30° C., the cI repressor protein is active and binds to the right and left operators of the infecting phage. This prevents transcription of any phage proteins and thus prevents lysis. However, at 42° C., the cI repressor is inactivated and cannot bind the promoter operators.

In one aspect, the present invention provides a cI repressor protein. In another aspect, the present invention provides a cI repressor protein having a sequence as set forth in SEQ ID NO:2, 44, 46, 48, 50, 52, 54, 56, or 58, and variant or fragment thereof. In yet another aspect, the present invention provides a cI repressor protein having at least 70%, at least 75%, at least 80%, at least 85%, at least 90%, at least 95%, 96%, 97%, 98% or 99% sequence identity to the polypeptide having a sequence as set forth in SEQ ID NO:2, 44, 46, 48, 50, 52, 54, 56, or 58. In yet another aspect, the present invention provides fragments and variants of the cI repressor protein identified above (SEQ ID NO:2, 44, 46, 48, 50, 52, 54, 56, or 58) which may readily be prepared by one of skill in the art using well-known molecular biology techniques. Variants are homologous polypeptides having an amino acid sequence at least about 75%, 80%, 85%, 90%, 95%, 96%, 97%, 98%, or 99% identity to the polypeptides of the invention, particularly to the amino acid sequence as set forth in SEQ ID NO:2, 44, 46, 48, 50, 52, 54, 56, or 58.

In another aspect, the present invention provides a polynucleotide, such as a cI gene, encoding a cI repressor protein, such as a polynucleotide encoding a cI repressor protein having a sequence as set forth in SEQ ID NO:2, 44, 46, 48, 50, 52, 54, 56, or 58. In yet another aspect, the present invention provides a polynucleotide encoding a cI repressor protein having at least 70%, at least 75%, at least 80%, at least 85%, at least 90%, at least 95%, 96%, 97%, 98% or 99% sequence identity to a polypeptide having a sequence as set forth in SEQ ID NO:2, 44, 46, 48, 50, 52, 54, 56, or 58, or a conservative variant, an allelic variant, a homolog or a fragment comprising at least eight or at east ten consecutive amino acids of one of these polypeptides, or a combination of these polypeptides. In another aspect, the present invention provides a polynucleotide having a nucleotide sequence as set forth in SEQ ID NO:1, 45, 47, 49, 51, 53, 55, 57, or 59, or a variant thereof. In yet another aspect, the present invention provides a polynucleotide having at least 70%, at least 75%, at least 80%, at least 85%, at least 90%, at least 95%, 96%, 97%, 98% or 99% sequence identity to a polynucleotide having a sequence as set forth in SEQ ID NO: 1, 45, 47, 49, 51, 53, 55, 57, or 59, or a variant thereof.

In one embodiment, the promoter driving the cI gene is the native cI gene promoter. In another embodiment, the promoter driving the cI gene is the weak promoter of Kanamycin gene (P1). In another embodiment, the promoter comprises a polynucleotide having a sequence as set forth in SEQ ID NO:29, 83, or 30. In yet another embodiment, the promoter comprises a polynucleotide having at least 70%, at least 75%, at least 80%, at least 85%, at least 90%, at least 95%, 96%, 97%, 98% or 99% sequence identity to a polynucleotide having a sequence as set forth in SEQ ID NO:29, 83, or 30.

Other promoter/repressor pairs which may be utilized in the methods of the present invention include, but are not limited to, a carB promoter controlled by the CarA-CarS repressor-antirepressor pair, growth hormone gene promoters and repressors and Lac repressor (lad) and the Ptrc-2 promoter.

The mutant promoter/repressor pair to serve as the substrate for the mutagenesis may be selected from among such mutants presently available and described in the art. Studies of the binding of mutant repressors to their operators [See, e.g., Nelson and Sauer, Cell, 42:549 (1985); Nelson and Sauer, J. Mol. Biol. 192:27 (1986); and Gussin, et al., Lambda II, (Hendrix, Roberts, Stahl, and Weisberg, eds) Cold Spring Harbor Press, Cold Spring Harbor, N.Y., p. 93-123 (1983)] permit the selection of known mutant promoter and/or mutant repressor sequences which may provide reduced, but not abolished, transcriptional rates. This selected promoter region is incorporated into a heterologous expression plasmid and then altered by conventional site-directed mutagenesis (see, e.g., Morinaga, et al., Biotechnology, 2:636, 1984). Alternatively, the repressor-encoding sequence is altered in an analogous fashion. The resultant mutant repressor/promoter pair is analyzed for its ability to promote secretion of the heterologous protein by comparison of expression with the wild-type plasmid not having been subjected to the site-directed mutagenesis.

The subject matter disclosed herein provides a drugless or antibiotic-free concept wherein the repressor activity (such as the cI repressor), expressed from the plasmid, inhibits transcription of a toxic gene product (such as the sacB gene product) placed under a λ phage promoter located on the cell host chromosome and wherein the host cells' viability in the presence of a substrate, such as sucrose, is ensured by a sufficient expression level from the plasmid of a repressor protein from the plasmid (such as the λcI repressor protein).

The growth of the host strain containing the antibiotic-free plasmid in the presence of sucrose ensures an efficient system to maintain and produce DNA plasmids.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

One embodiment of the present invention relates to a drugless plasmid comprising one or more repressor gene operably linked to one or more promoter. In one aspect, the drugless plasmid comprises a polynucleotide encoding a cI repressor protein. In another aspect, the drugless plasmid comprises a promoter operably linked to the polynucleotide encoding the cI repressor protein. The promoter may be the native cI gene promoter or the weak promoter of Kanamycin gene. In another aspect, the drugless plasmid further comprises a heterologous polynucleotide encoding an immunogen or a protein. In another aspect, the drugless plasmid comprises a promoter operably linked to the heterologous polynucleotide encoding the immunogen or protein. Any suitable promoter known in the art can be employed in the drugless plasmids according to the present invention, including bacterial, yeast, fungal, insect, mammalian, and plant promoters. The promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995). The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. Other promoters from gram-negative bacteria are also suitable including, but not limited to, promoters isolated from *Avibacterium, Brucella, Escherichia coli, Haemophilus* (e.g., *Haemophilus suis*), *Salmonella* (e.g., *Salmonella enteridis, Salmonella typhimurium, Salmonella infantis*), *Shigella, Pasteurella,* and *Rimeirella*.

The plasmids may comprise other expression control elements. It is particularly advantageous to incorporate stabilizing sequence, e.g., intron sequence, for example, the first intron of the hCMV-IE (PCT Application No. WO1989/01036), the intron II of the rabbit β-globin gene (van Ooyen et al., 1979). In another embodiment, the plasmids may comprise 3' UTR. The 3' UTR may be, but not limited to, *agrobacterium* nopaline synthase (Nos) 3' UTR.

As to the polyadenylation signal (polyA) for the plasmids and viral vectors other than poxviruses, use can be made of the poly(A) signal of the bovine growth hormone (BGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Another embodiment of the present invention relates to a gram-negative bacterium host strain comprising a drugless plasmid. One aspect of the embodiment relates to a gram-negative bacterium host train comprising the drugless plasmid and a heterologous polynucleotide inserted in one or more non-essential region of the host chromosome, and wherein the heterologous polynucleotide is operably linked to a promoter which can be tightly regulated by a repressor. In another aspect of the embodiment, the heterologous polynucleotide inserted in the host chromosome is a sacB gene. In another aspect of the embodiment, the sacB gene is operably linked to a promoter, such as the right promoter of the λ phage. It is recognized that the sacB gene and the promoter may be inserted in multiple copies, for example, two or three copies, in the host chromosome. The non-essential region of the host strain may be the deA or purN gene on the *E. coli* chromosome. The deA and purN genes are nonessential and deletion of the these genes does not affect the growth rate of the bacteria (Kim, J. et al., Biochemistry. 46, 44:12501-12511). In one aspect, one copy of the sacB gene and promoter cassette is inserted in either deA locus or purN locus by allelic replacement. In another aspect, two copies of the sacB gene and promoter cassette are inserted in either deA locus or purN locus. In yet another aspect, two copies of the sacB gene and promoter cassette are inserted in the host chromosome, wherein one copy of the sacB gene and promoter cassette is inserted in the deA locus and the other copy is inserted in the purN locus. The sacB gene and promoter cassette refers to the polynucleotide comprising the sacB gene operably linked to a promoter. In one aspect, the sacB gene and promoter cassette comprises a sacB gene and the right promoter of the λ phage. In another aspect, the sacB gene and promoter cassette comprises a polynucleotide having the sequence as set forth in SEQ ID NO:75.

The subject matter disclosed herein further relates to a vaccine or composition comprising the drugless plasmids comprising a heterologous gene encoding an immunogen or a protein, or a vaccine or composition comprising the immunogen or protein expressed using the drugless plasmids. The vaccine or composition may further comprise a pharmaceutical acceptable carrier.

In one embodiment, the immunogen is selected from a feline pathogen such as, but not limited to, feline herpesvirus (FHV), feline calicivirus (FCV), feline leukemia virus (FeLV), feline immunodeficiency virus (FIV), rabies virus, and the like, and combinations thereof.

In another embodiment, the immunogen is selected from a canine pathogen including, but not limited to, rabies virus, canine herpesvirus (CHV), canine parvovirus (CPV), canine coronavirus, *Leptospira canicola, Leptospira icterohaemorragiae, Leptospira grippotyphosa, Borrelia burgdorferi, Bordetella bronchiseptica* and the like, and combinations thereof.

In yet another embodiment, the immunogen is selected from an equine pathogen, such as equine herpesvirus (type 1 or type 4), equine influenza virus, tetanus, west nile virus, *Streptococcus equi, Rhodococcus equi* and the like or combinations thereof.

In yet another embodiment, the immunogen is selected from a bovine pathogen, such as rabies virus, bovine rotavirus, bovine parainfluenza virus type 3 (bPIV-3), bovine coronavirus, bovine viral diarrhea virus (BVDV), foot and mouth disease virus (FMDV), bovine respiratory syncytial virus (BRSV), Infectious Bovine Rhinotracheitis virus (IBR), *Escherichia coli, Pasteurella multocida, Pasteurella haemolytica, salmonella, Cryptosporidium* and the like and combinations thereof.

In still another embodiment, the immunogen is selected from a porcine pathogen such as, but not limited to, swine influenza virus (SIV), porcine circovirus type 2 (PCV-2), porcine reproductive respiratory syndrome virus (PRRS), pseudorabies virus (PRV), porcine parvovirus (PPV), FMDV, *Mycoplasma hyopneumoniae, Erysipelothrix rhusiopathiae, Pasteurella multocida, Bordetella bronchiseptica, Escheri-*

*chia coli*, Bluetongue virus, African Horse Sickness virus, Rift Valley Fever, Nipah virus and the like, and combinations thereof.

The term "antigen" or "immunogen" is used interchangeably and means a substance that induces a specific immune response in a host animal. The antigen may comprise a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

The cationic lipids containing a quaternary ammonium salt which are advantageously but not exclusively suitable for plasmids, are advantageously those having the following formula:

$$R_1-O-CH_2-CH-CH_2-\overset{CH_3}{\underset{CH_3}{\overset{|+}{N}}}-R_2-X$$
$$\phantom{R_1-O-CH_2-}OR_1\phantom{-CH_2-}CH_3$$

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50: about 1 and about 1:about 10, such as about 10:about 1 and about 1:about 5, and advantageously about 1:about 1 and about 1:about 2, e.g., 1:1 and 1:2.

In another embodiment, pharmaceutically or veterinarily acceptable carrier, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (Tween 80®), available from AppliChem, Inc., Cheshire, Conn.) and sorbitan esters (e.g., sorbitan monooleate (Span 80®), available from Sigma Aldrich, St. Louis, Mo.). In addition, with respect to a water-in-oil emulsion, see also U.S. Pat. No. 6,919,084, e.g., Example 8 thereof, incorporated herein by reference. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (see, e.g., U.S. Pat. No. 6,358,500, incorporated herein by reference). Examples of other suitable emulsions are described in U.S. Pat. No. 7,371,395, incorporated herein by reference.

The vaccine or composition can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). The vaccine or composition can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. The vaccine or composition may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The subject matter disclosed herein further relates to a method of producing a drugless plasmid comprising the steps of 1) engineering a gram negative bacterium host strain comprising a heterologous polynucleotide inserted by allelic replacement in one or more non-essential region of the host chromosome; 2) constructing a DNA plasmid comprising a polynucleotide encoding a cI repressor protein; 3) transforming the bacterium host strain with the DNA plasmid comprising the gene encoding the cI repressor protein; 4) growing the transformed bacterium host stain in the presence of sucrose at a temperature ranging from 30° C. to 42° C.; and 5) recovering the DNA plasmid.

In one aspect of the embodiment, the DNA plasmid further comprises a heterologous polynucleotide encoding an immunogen or a protein, wherein the heterologous polynucleotide is operably linked to a promoter. The promoter may be a promoter functional in prokaryotic or eukaryotic cell, such as a CMV promoter.

The subject matter disclosed herein further relates to a method of producing a protein or an immunogen using the drugless plasmids comprising the steps of 1) engineering a gram negative bacterium host strain comprising a heterologous polynucleotide inserted by allelic replacement in one or more non-essential region of the host chromosome; 2) constructing a DNA plasmid comprising a polynucleotide encoding a cI repressor protein and a gene encoding an immunogen or a protein; 3) transforming the bacterium host strain with the DNA plasmid comprising the polynucleotide encoding the cI repressor protein and the gene encoding the immunogen or protein; 4) growing the transformed bacterium host stain in the presence of sucrose at a temperature ranging from 30° C. to 42° C.; and 5) recovering the immunogen or protein.

In one aspect of the embodiment, the gene encoding an immunogen or a protein is operably linked to a promoter functional in prokaryotic cells. The promoter may be promoter from gram-negative bacteria, including, but not limited to, promoters isolated from *Avibacterium, Brucella, Escherichia coli, Haemophilus* (e.g., *Haemophilus suis*), *Salmonella* (e.g., *Salmonella enteridis, Salmonella typhimurium, Salmonella infantis*), *Shigella, Pasteurella,* and *Rimeirella*.

In one aspect of the embodiment, the heterologous polynucleotide inserted in the host chromosome encodes a sacB protein. In another aspect, the sucrose concentration may range from 0% to about 20%, about 1% to about 20%, about 1% to about 15%, about 1% to about 10%. In yet another aspect, the sucrose contraction may range from about 1% to about 10%, about 1% to about 2%, about 2% to about 3%, about 3% to about 4%, about 4% to about 5%, about 5% to about 6%, about 6% to about 7%, about 7% to about 8%, about 8% to about 9%, or about 9% to about 10%. In yet another aspect, the sucrose contraction may be about 1%, about 2%, about 3%, about 4%, about 5%, about 6%, about 7%, about 8%, about 9%, or about 10%.

In one aspect of the embodiment, the temperature may range from about 30° C. to about 42° C. In another aspect, the temperature may range from about 30° C. to about 41° C., about 30° C. to about 39° C., about 30° C. to about 38° C., about 30° C. to about 37° C. In yet another aspect, the temperature may be about 30° C., about 31° C., about 32° C., about 33° C., about 34° C., about 35° C., about 36° C., about 37° C., about 38° C., about 39° C., about 40° C., or about 41° C.

The term recovering includes but is not limited to collecting, extracting, harvesting, or purifying from the culture medium.

An "isolated" biological component (such as a polynucleotide, DNA plasmid, protein or organelle) refers to a component that has been substantially separated or purified away from other biological components in the cell of the organism in which the component naturally occurs, for instance, other chromosomal and extra-chromosomal DNA and RNA, proteins, and organells. Polynucleotides (including DNA plasmids) and proteins that have been "isolated" include polynucleotides and proteins purified by standard purification methods, for example, see Russell, David W.; Sambrook, Joseph (2001), Molecular cloning: a laboratory manual. Cold Spring Harbor, N.Y: Cold Spring Harbor Laboratory. The term also embraces polynucleotides and proteins prepared by recombinant technology as well as chemical synthesis.

The term "purified" as used herein does not require absolute purity; rather, it is intended as a relative term. Thus, for example, a purified polypeptide or polynucleotide preparation is one in which the polypeptide or polynucleotide is more enriched than the polypeptide or polynucleotide is in its natural environment. That is the polypeptide or polynucleotide is separated from cellular components. By "substantially purified" is intended that such that at least 60%, at least 70%, at least 80%, at least 90%, at least 95%, or at least 98%, or more of the cellular components or materials have been removed. Likewise, the polypeptide or polynucleotide may be partially purified. By "partially purified" is intended that less than 60% of the cellular components or material is removed.

The present invention further provides for methods for inducing an immune or protective response in an animal, comprising administering to the animal an immunological composition, a vaccine or a composition according to the invention. The immune responses elicited are notably antibody and/or cellular immune responses, and in particular, a gamma-interferon response.

In particular, the present invention provides for methods to immunize against, or to prevent or to reduce the symptoms caused by, infection of an animal with a pathogenic organism (for example, infection by a virus, bacteria, fungus, or protozoan parasite). The method of the present invention is useful in vertebrate animals including, but not limited to, humans, canines (e.g., dogs), felines (e.g., cats); equines (e.g., horses), bovines (e.g., cattle) and porcine animals (e.g., pigs), as well as in avians including, but not limited to, chickens, turkeys, ducks, geese, a quail, a pheasant, parrots, finches, hawks, crows and ratites (ostrich, emu, cassowary, and the like). The method of the present invention is also useful for providing fish DNA vaccines.

In a particular aspect of the invention, these methods consist of the vaccination of pregnant females before parturition by administering a vaccine composition made according to the invention. These methods further include the induction of protective antibodies elicited by the vaccination protocol and the transfer of these protective antibodies from vaccinated pregnant females to their offspring. The transfer of such maternal antibodies subsequently protects the offspring from disease.

The dosage of the vaccine composition made according to the present invention will depend on the species, breed, age, size, vaccination history, and health status of the animal to be vaccinated. Other factors like antigen concentration, additional vaccine components, and route of administration (i.e., subcutaneous, intradermal, oral, intramuscular or intravenous administration) will also impact the effective dosage. The dosage of vaccine to administer is easily determinable based on the antigen concentration of the vaccine, the route of administration, and the age and condition of the animal to be vaccinated. Each batch of antigen may be individually calibrated. Alternatively, methodical immunogenicity trials of different dosages, as well as MPD (Minimum Protective Dose) studies and other screening procedures can be used to determine effective dosage for a vaccine composition in accordance with the present invention without undue experimentation. From the examples presented below, it will be readily apparent what approximate dosage and what approximate volume would be appropriate for using the vaccine composition described herein. The critical factor is that the dosage provides at least a partial protective effect against natural infection, as evidenced by a reduction in the mortality and morbidity associated with natural infection. The appropriate volume is likewise easily ascertained by one of ordinary skill in the art. For example, in avian species the volume of a dose may be from about 0.1 ml to about 0.5 ml and, advantageously, from about 0.3 ml to about 0.5 ml. For feline, canine and equine species, the volume of a dose may be from about 0.2 ml to about 3.0 ml, advantageously from about 0.3 ml to about 2.0 ml, and more advantageously, from about 0.5 ml to about 1.0 ml. For bovine and porcine species, the volume of dose may be from about 0.2 ml to about 5.0 ml, advantageously from about 0.3 ml to about 3.0 ml, and more advantageously from 0.5 ml to about 2.0 ml.

Repeated vaccinations may be preferable at periodic time intervals to enhance the immune response initially or when a long period of time has elapsed since the last dose. In one embodiment of the present invention, the vaccine composition is administered as a parenteral injection (i.e., subcutaneously, intradermally, or intramuscularly). The composition may be administered as one dose or, in alternate embodiments, administered in repeated doses of from about two to about five doses given at intervals of about two to about six weeks, preferably from about two to about five weeks. However, one of skill in the art will recognize that the number of doses and the time interval between vaccinations depends on a number of factors including, but not limited to, the age of the animal vaccinated; the condition of the animal; the route of immunization; amount of antigen available per dose; and the like. For initial vaccination, the period will generally be longer than a week and preferably will be between about two to about five weeks. For previously vaccinated animals, a booster vaccination, before or during pregnancy, at about an annual interval may be performed.

The present invention also contemplates administering a vaccine composition using a needlefree injector such as Pigjet®, Avijet®, Dermojet® or Biojector® (Bioject, Oreg., USA). An person of ordinary skill in the art is able to adjust the specifications of the injector as required with regard to factors such as the species of the animal to be vaccinated; the age and weight of the animal, and the like without undue experimentation.

The present invention further relates to a kit comprising a first vial containing an active ingredient such as an immunogen or pharmaceutical composition and, in a second vial, a diluent made according to the present invention. The immunogen may be in a lyophilized form, a dried form or in aqueous solution as described herein.

The invention will now be further described by way of the following non-limiting examples.

EXAMPLES

Example 1

The Antibiotic-Free Plasmid Maintenance Concept

The following example demonstrates a new concept for maintaining a high number of plasmid copies within a gram-negative host cell which is based on three components:
1. a gram-negative bacterium host which expresses a toxic product for the gram-negative bacterium under defined culture conditions wherein the toxic gene is inserted into one or more non essential region of bacterium host chromosome.
2. The presence on the bacterium chromosome of a gene encoding the toxic product under the control of a constitutive promoter that can be tightly regulated; and
3. Expression of a specific repressor from the plasmid that regulates the promoter operably linked to the toxic gene on the host chromosome.

In this design, it is the presence of the plasmid that controls the multiplication of the gram-negative bacterium host when it is under defined culture conditions (e.g. in the presence of sucrose).

In the first component, the gram negative bacterium is transformed to express the sacB gene coding for levansucrase (see FIG. 1). The second and third components relate to the cI repressor gene product and the Right λ promoter. The cI gene of λ bacteriophage codes for the λ repressor.

Figure 2:
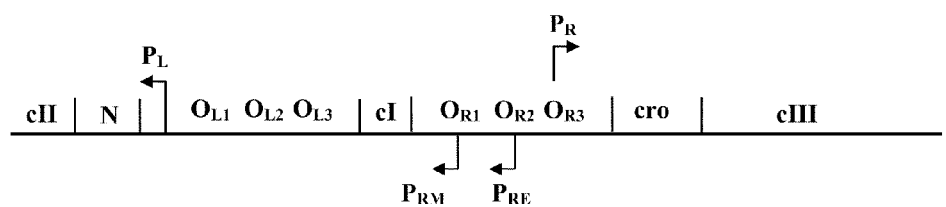
FIG. 2 describes the second and third components of the drugless or antibiotic-free concept which is the immunity region of phage λ, wherein cI codes for cI repressor; cro codes for Cro protein; N codes for the transcription anti-terminator; cII codes for cI activator; cIIIcodes for the cIII protease inhibitor; OL 1, 2 and 3 and OR 1, 2 and 3 are operators; PL and PR are the rightward and leftward promoters; PRE is the promoter for repressor establishment; PRM is the promoter for repressor maintenance.

The region of the genome that codes for the cI repressor protein is known as the immunity region. The immunity region is illustrated in FIG. 2. A plasmid system expressing the cI gene product should inhibit the transcription of the sacB gene placed under the control of the λ promoter. Such a repression should confer resistance to sucrose and allow both the plasmid maintenance and propagation in the host cells (see FIG. 1).

Figure 3:
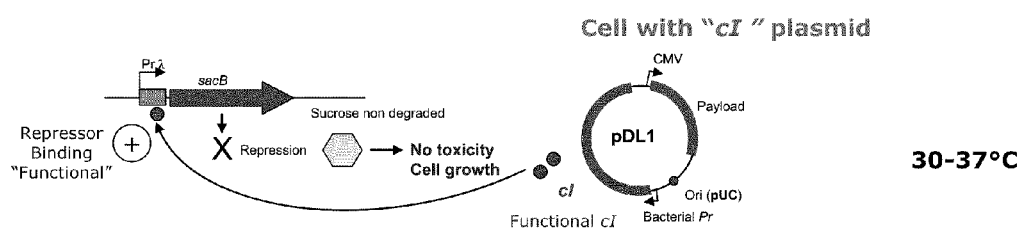
FIG. 3 describes the theoretical overview of the "drugless" concept wherein the cI repressor activity, expressed from the pDL1 (DrugLess Plasmid) plasmid, inhibits transcription of the toxic sacB gene product placed under the λPr promoter located on the cell host chromosome and wherein the host *E. coli* cells' viability in the presence of sucrose is ensured by a sufficient expression level of the λcI repressor protein from the plasmid.

FIG. 3 describes the overview of the "drugless" concept wherein the cI repressor activity, expressed from the plasmid, inhibits transcription of the toxic sacB gene product placed under the λPr promoter located on the cell host chromosome and wherein the host E. coli cells' viability in the presence of sucrose is ensured by a sufficient expression level of the λcI repressor protein from the plasmid. The cI repressor binding to its specific promoter is optimal at temperatures between 30° C. and 37° C. (see FIG. 3).

Figure 6A:
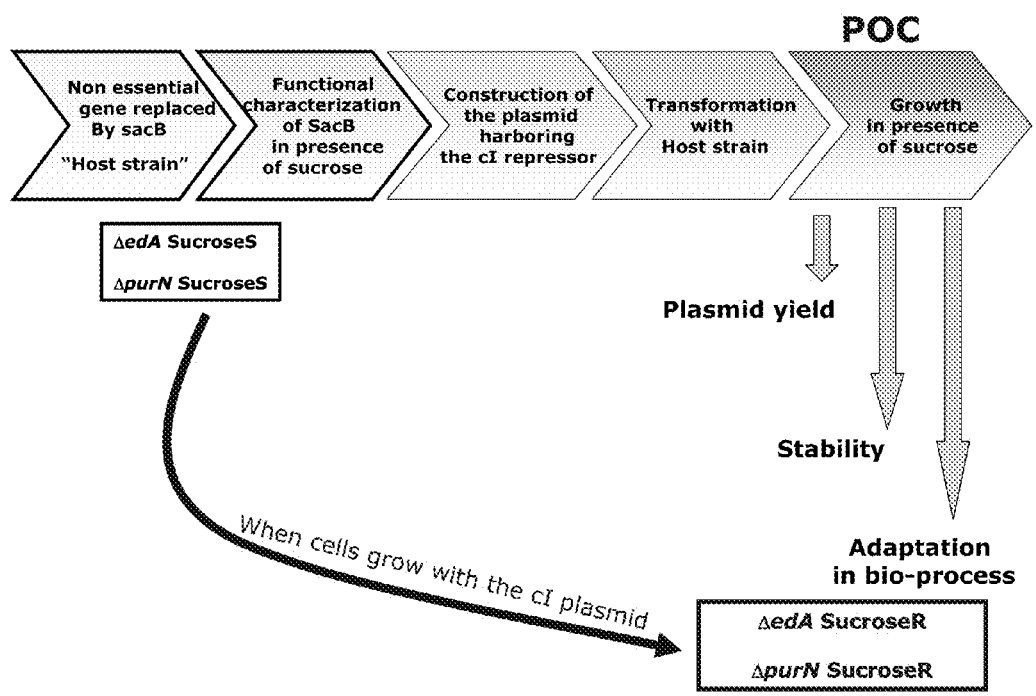
FIGS. 6A-6C illustrate the experimental plan.
Figure 6B:
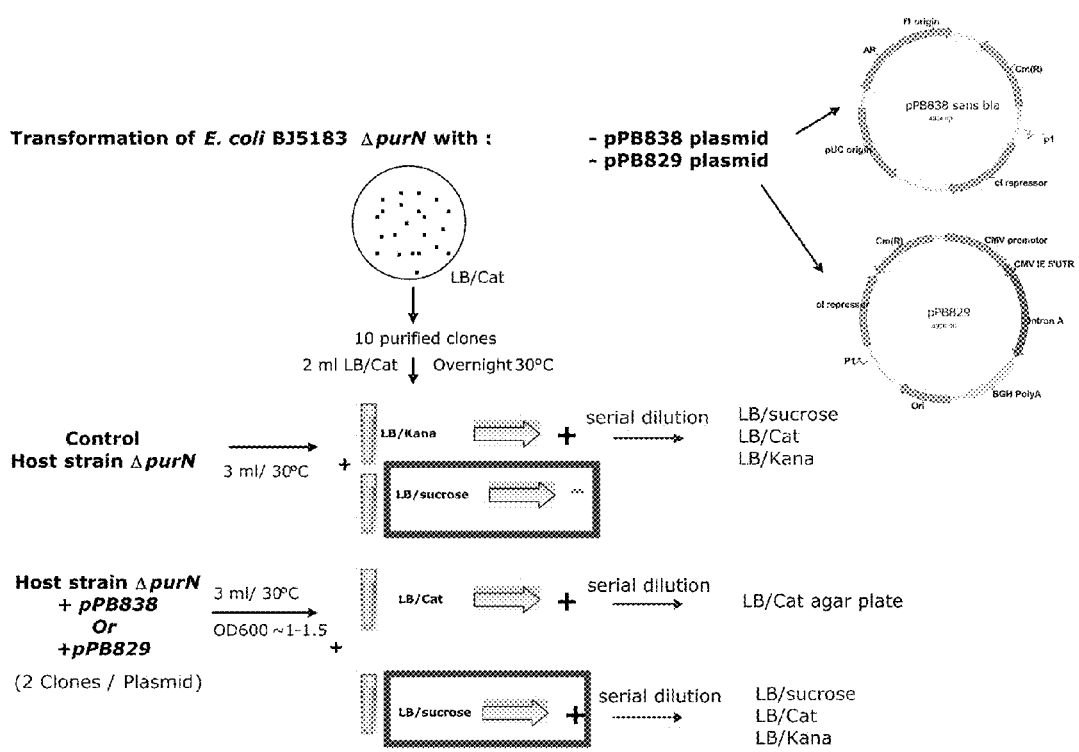
Figure 6C:
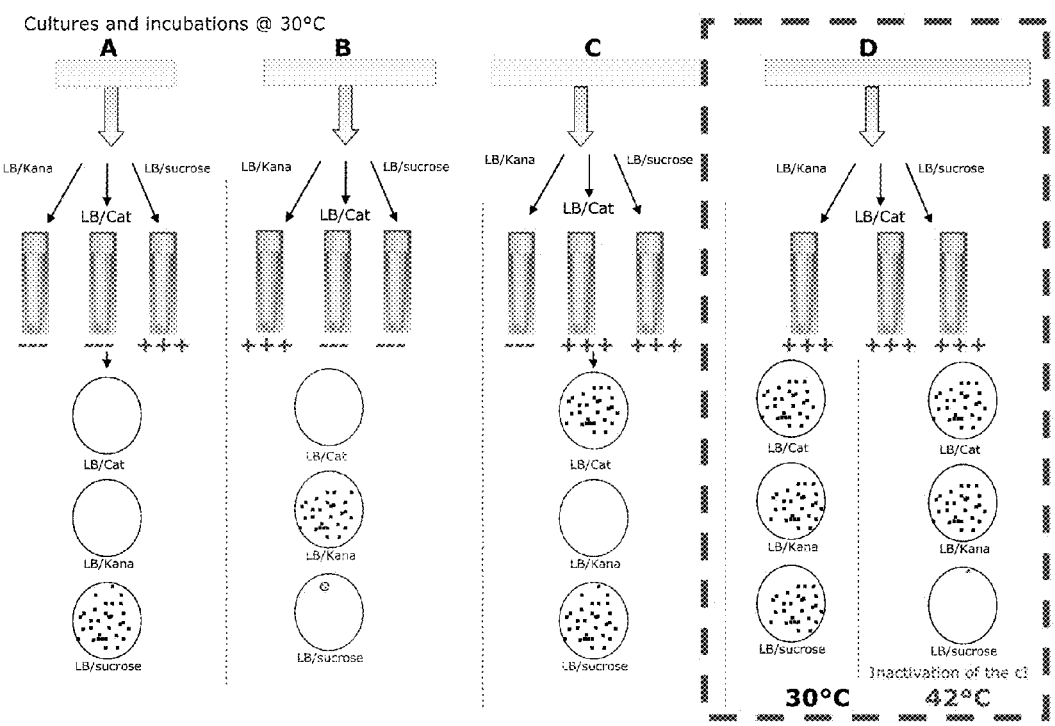

In specific case (such as when using the temperature sensitive cI857 repressor), the cI repressor will not bind the promoter at temperatures higher than 40° C. Therefore, a switch to 42° C. inhibits the binding activity of cI repressor to the λPr promoter and should render the host cells sensitive to sucrose (more particularly the levan subproducts) as a consequence. The 42° C. temperature incubation in the presence of sucrose is a condition ad hoc to validate the functionality of the entire system and constitutes a "negative proof" in support of the full functionality of the system (see FIG. 4 and FIG. 6C). Indeed, the parental cells λPr::sacB purNΩkan transformed with either the pPB829 or pPB838 plasmid growing in the presence of either Cat or Sucrose were not viable when plated on LB sucrose agar upon incubation at 42° C. This demonstrates that the viability of the parental cells is dependent on the maintenance of plasmid comprising the cI gene.

Example 2

Generation of the E. Coli Host Strain Harboring the λPromoter/Levansucrase Gene

Two engineered host strains containing the λPr::sacBΩkan cassette were prepared wherein the cassette, containing the sacB gene under the control of the lambda promoter (λPr), is marked with Kanamycin and then introduced into the E. coli chromosome by allelic replacement of either edA or purN gene. These genes are not essential and their deletion does not affect the growth rate. The transformed cells became highly sensitive to sucrose.

Figure 8A:
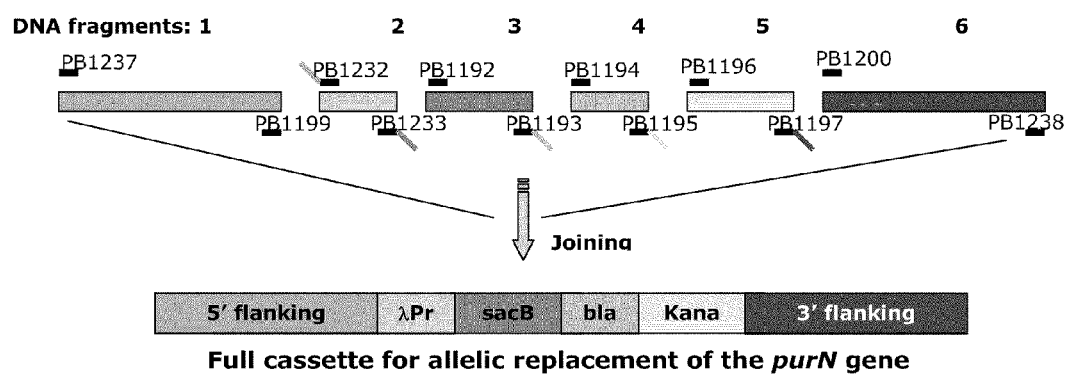
FIGS. 8A-E illustrate host strain engineering.
Figure 8B:
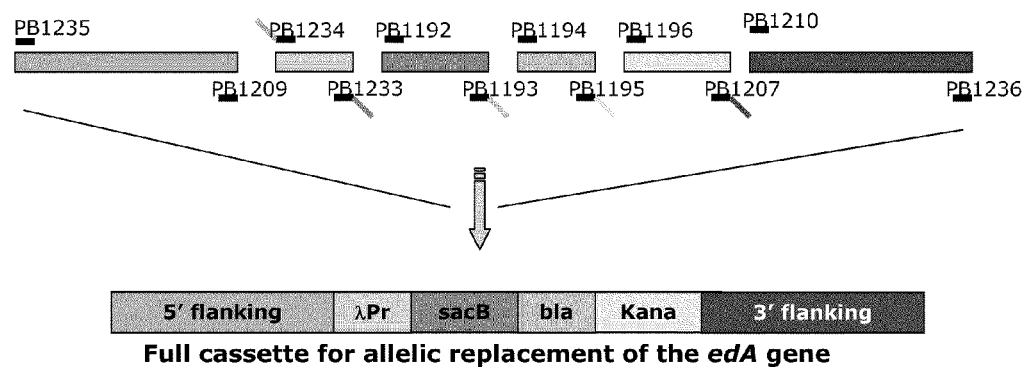

FIGS. 8A-B show that the λPr::sacBΩkan cassette to be inserted by allelic replacement of edA or purN gene, respectively, into the E. coli chromosome is composed of six independent components that were PCR amplified before being fused by joining PCR.

Figure 8C:
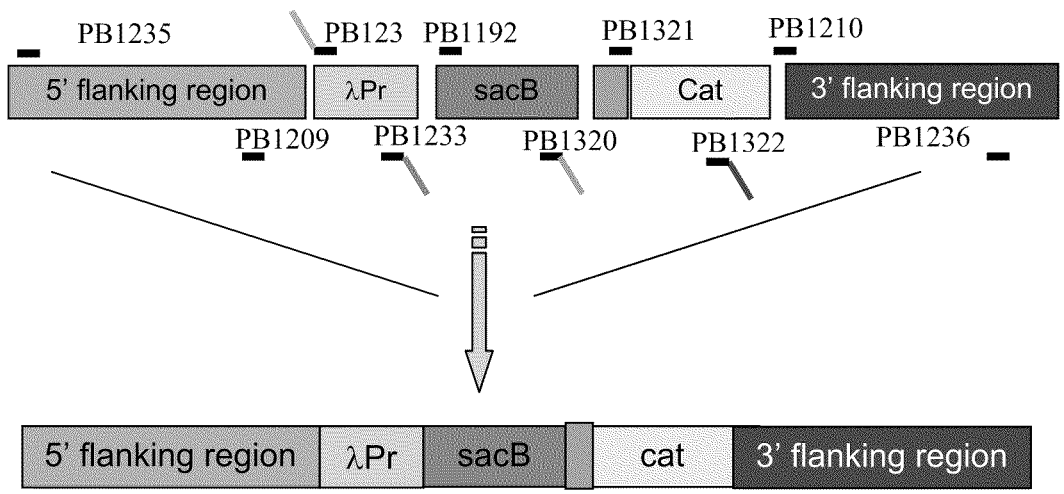
Figure 8D:
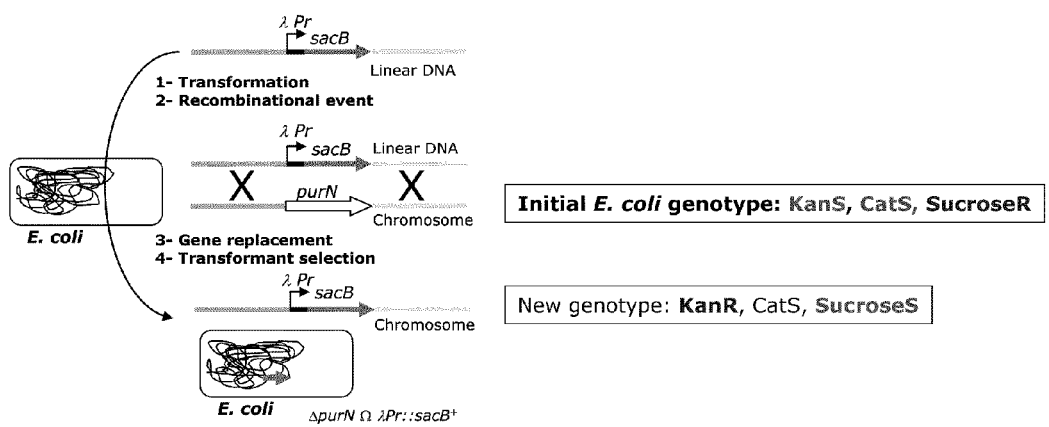

FIG. 8D shows that the λPr::sacBΩkan cassette was inserted into the chromosome of E. coli by allelic replacement of the edA or purN gene. This cassette insertion was performed by transforming E. coli with a linear DNA template, containing a deleted gene flanked by up- and downstream homologous region of the chromosome locus, and transferred into a recombination-proficient *E. coli* strain, such as recD, recB recC sbcA mutants. The *E. coli* strain for the engineering of the parental strain was the BJ5183 strain from Stratagene (ref# 200154), wherein the genotype was endA1 sbcBC recBC galK met thi-1 bioT hsdR (Str$^r$). As shown, the initial phenotype of the *E. coli* wild type was Kan$^S$, Cat$^S$ and Sucrose$^R$. Following the transformation of the strain, the phenotype turned Kan$^R$, Cat$^s$ and Sucrose$^S$. This latest phenotype was one of the parental strain used for the further experiments dealing with the demonstration of the functionality of the antibiotic-free plasmid.

FIG. 8C shows that the λPr:: sacB Ωcat cassette to be inserted by allelic replacement of edA gene into the Prλ:: sacBΩkan *E. coli* chromosome was composed of six independent components that were PCR amplified before being fused by joining PCR. The goal of the new λPr:: sacB Ωcat cassette targeting the deletion of the edA gene by allelic exchange was to engineer a double deletion mutant ΔedA ΔpurN expressing two sacB cassettes.

Figure 8E:
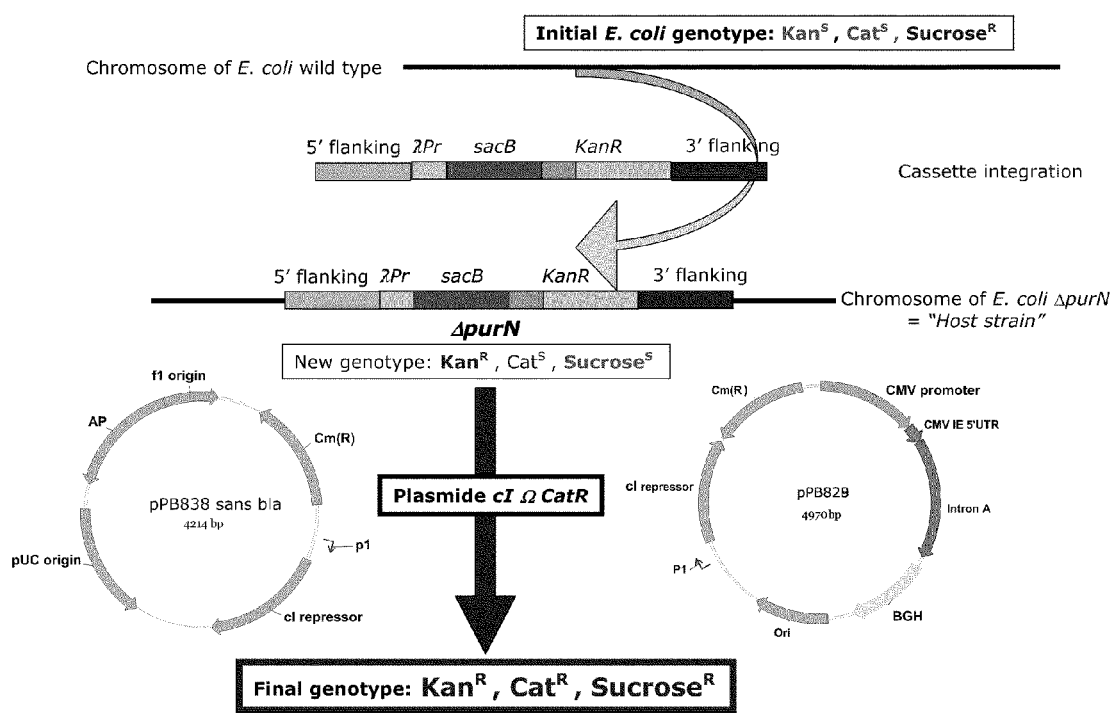

FIG. 8E shows that when the parental strain was transformed with the cI plasmid (pPB829 or pPB838), the cells (parental strain+cI plasmid [pPB829 or pPB838]) became resistant to kanamycin (Kan$^R$), chloramphenicol (Cat$^R$) and sucrose (Sucrose$^R$). The figure illustrates the coexistence of the engineered host strain (ΔpurN λPr::sacB$^+$Ωkan) or (ΔedA λPr::sacB$^+$Ωkan) and drug plasmid to demonstrate proof of concept when the sacB gene was placed under the control of the lambda promoter and the construct was introduced into the chromosome of *E. coli* by allelic replacement of the edA or purN gene. The transformed cells became highly sensitive to sucrose. When the chloramphenicol marked plasmids (pPB838 or pPB829) comprising the cI repressor was introduced into the ΔpurN λPr::sacB$^+$Ωkan or ΔedA λPr::sacB$^+$Ωkan strains, the transformed cells became resistant to kanamycin, chloramphenicol and sucrose.

The λPromoter (λPr) was amplified with PB1232 and PB1233 primers for purN deletion.

```
PB1232 primer (SEQ ID NO: 6):
(CCGAACAACGCGTGGTTATCGACACCGCAAGGGATAAATATCTAAC ACCG)
and PB1233 primer (SEQ ID NO: 7):
(CAAACTTTTTGATGTTCATATCCATCTGATCCTCTTCAAAAGGCCA

CCTG)
```

The λPromoter (λPr) was amplified with PB1234 and PB1233 primers for edA deletion.

```
PB1234 (SEQ ID NO: 8):
(GACGACAAATTTGTAATCAGGCGAGAGCACCGCAAGGGATAAATATC

TAACACCG)
```

The amplification of λPromoter (λPr) (SEQ ID NO:5) was performed using the pLDR8 plasmid (ATCC# 77357) as DNA template. The sacB gene (SEQ ID NO:3) was amplified with the PB1192 (SEQ ID NO:9) (ATGGATATGAACAT-CAAAAAGTTTGC) and PB1193 (SEQ ID NO:10) (AAA-CAAATAGGGGTTCCGCGCACATT-TATTTGTTAACTGTTAATTGTCCTTG) primers using the pNB350 (Merial proprietary property) as DNA template when the joining PCR was used for the engineering of the λPr::sacB Ωkan cassette (see FIG. 8A-B). For the engineering of the λPr::sacB Ωcat cassette, the reverse primer PB1320 (SEQ ID NO:80) (GCCGATCAACGTCTCATTTTCGC-CGTTAACAGATCTTTATTTGTTAACTGTTAATTGT CCTTG) was used in place of PB1193. The bla promoter was amplified with the PB1194 (SEQ ID NO:11) (ATGT-GCGCGGAACCCCTATTTG) and PB1195 (SEQ ID NO:12) (GACGTTTCCCGTTGAATATGGCTCAT-ACTCTTCCTTTTTCAATATTATTGAAGC) primers using the pCMVβ as DNA template. The Kanamycin resistance gene was amplified with the PB1196 (SEQ ID NO:13) (AT-GAGCCATATTCAACGGGAAACG) and PB1197 (SEQ ID NO:14)(GAAAAACGCCAGCGGCAGAGCTGGCGCT-TAGAAAAACTCATCGAGCATCAA ATG) primers using the plasmid pLL14 (containing the weak promoter for Kanamycin gene, Merial proprietary material) as DNA template. The chloramphenicol (cat) resistance genee placed under the control of its native cat promoter was amplified with the PB1321 (SEQ ID NO:81) (AGATCTGTTAACGGC-GAAAATGAG) and PB1322 (SEQ ID NO:82) (AAAACGCTACAAAAATGCCCGATCCTT-TACGCCCCGCCCTGCCACTCATCGC) primers using the pPB829 as DNA template. The 5' flanking region of the purN gene was amplified with PB1237 (SEQ ID NO:15) (TTTGCGGCCGCTGGTGGTGGTCGCCAT-GTGCGTTAATGACC) and PB1199 (SEQ ID NO:16) (TAT-TCGATAACCACGCGTTGTTCGG) using genomic DNA of the *E. coli* SCS1 strain as DNA template. The 3' flanking region of the purN gene was amplified with PB1200 (SEQ ID NO:17) (GCGCCAGCTCTGCCGCTGGCGTTTTTC) and PB1238 (SEQ ID NO:18) (TTTGGATCCGCTGGTG-GATATCATCAAGGCAGTAACGCAGAATG) primers using genomic DNA of the *E. coli* SCS1 strain as DNA template. The 5' flanking region of the edA gene was amplified with the PB1235 (SEQ ID NO:19) (TTTGCGGCCGCTG-GTGGTTGAGAACCAGGTGATTGAAGCC) and PB1209 (SEQ ID NO:20) (CTCTCGCCTGATTA-CAAATTTGTCGTC) primers using genomic DNA of SCS1 as DNA template. The 3' flanking region of the edA gene was amplified with the following primers PB1210 (SEQ ID NO:21) (AGGATCGGGCATTTTTGTAGCGT) and PB1236 (SEQ ID NO:22) (TTTCTAGAGCTGGTGGCGACTAC-CGTGAATCCTGGCAACC) primers using plasmid pLDR8 as template DNA.

These six individual PCR products of the λPr::sacB Ωkan cassette or the λPr::sacB Ωcat to be transferred into the *E. coli* chromosome were fused together following a joining PCR (FIG. 8A-B-C). These six individual amplified fragments were purified with a PCR clean-up kit (Geneclean turbo kit; MP Biomedicals, CA, USA) and a second round PCR was set up with all the 6 fragments and without primers. The PCR condition was as follows: PCR mixture (final 25 μl), 1 μl of each PCR fragment, 2 μl of dNTP (2.5 mM each, 5 μl of 5×PCR buffer, 11.5 μl sterile distilled water, 0.5 μl Phusion DNA polymerase (Finenzymes, Finland); PCR cycles: 98° C. 30 s, (98° C. 10 s, 60° C. 30 s, 72° C. 5 min)*15 cycles and 72° C. 10 min. The third round PCR amplification was performed with 1 μl of the purified second round product by using the PB 1235 and PB1236 primers for purN (allelic replacement) and the PB1237 and PB1238 primers for edA (allelic replacement). The PCR condition was as follows: PCR mixture (final 50 μl), 1 μl of second PCR fragment, 1 μl of dNTP (2.5 mM each, 10 μl of 5×PCR buffer, 37 μl sterile distilled water, 0.25 μl forward primer, 0.25 μl reverse primer, 0.5 μl Phusion DNA polymerase (Finenzymes, Finland); PCR cycles: 98° C. 30 s, (98° C. 15 s, 60° C. 30 s, 72° C. 4 min)*35 cycles and 72° C. 10 min. The final PCR-joined amplicons (4007 by for the purN allelic replacement and 3407 by for the edA allelic replacement) were checked on agarose gel and purified before transformation into *E. coli*. Each joined-PCR amplicon was checked by restriction analysis.

Figure 9B:
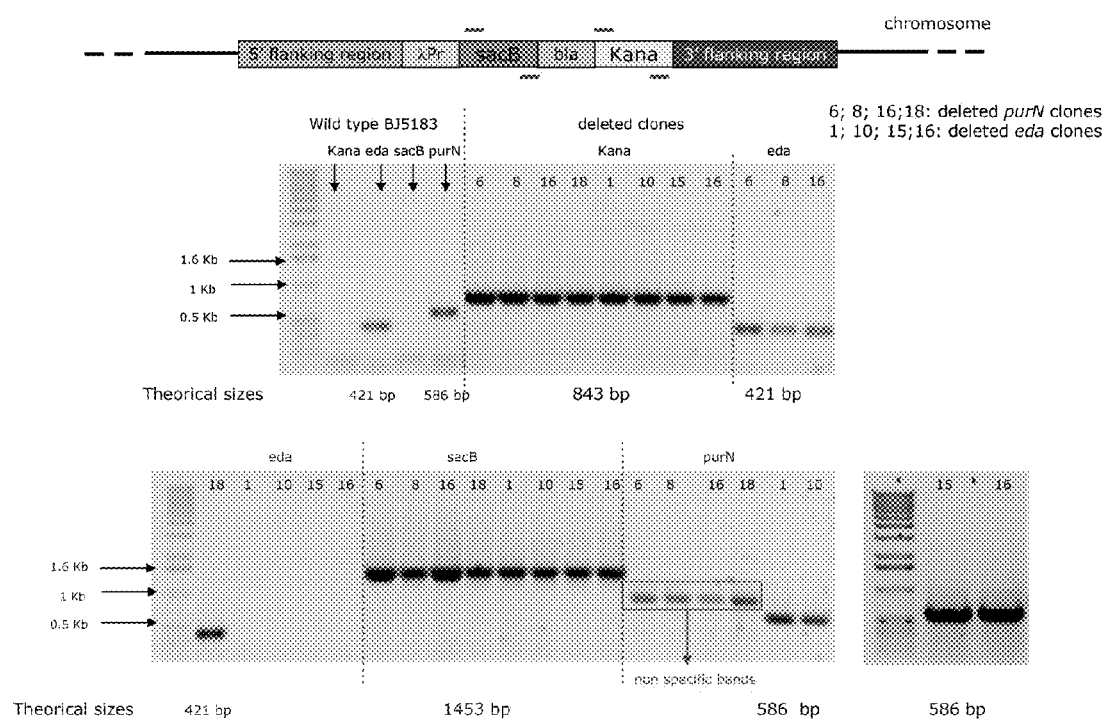
Figure 9C:
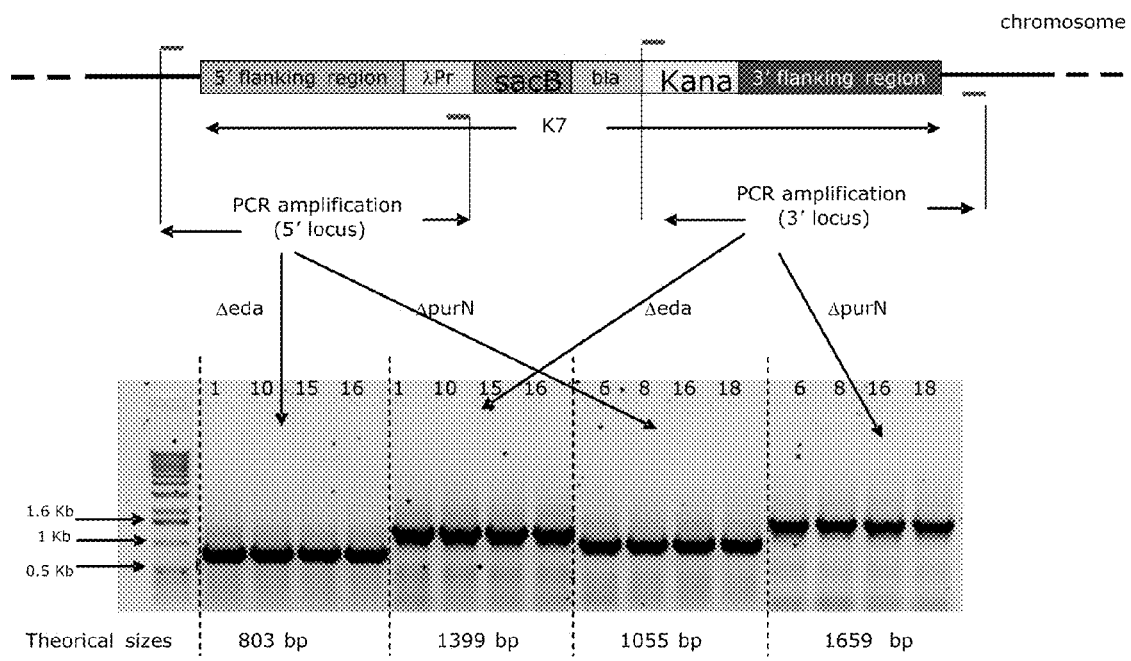
Figure 10A:
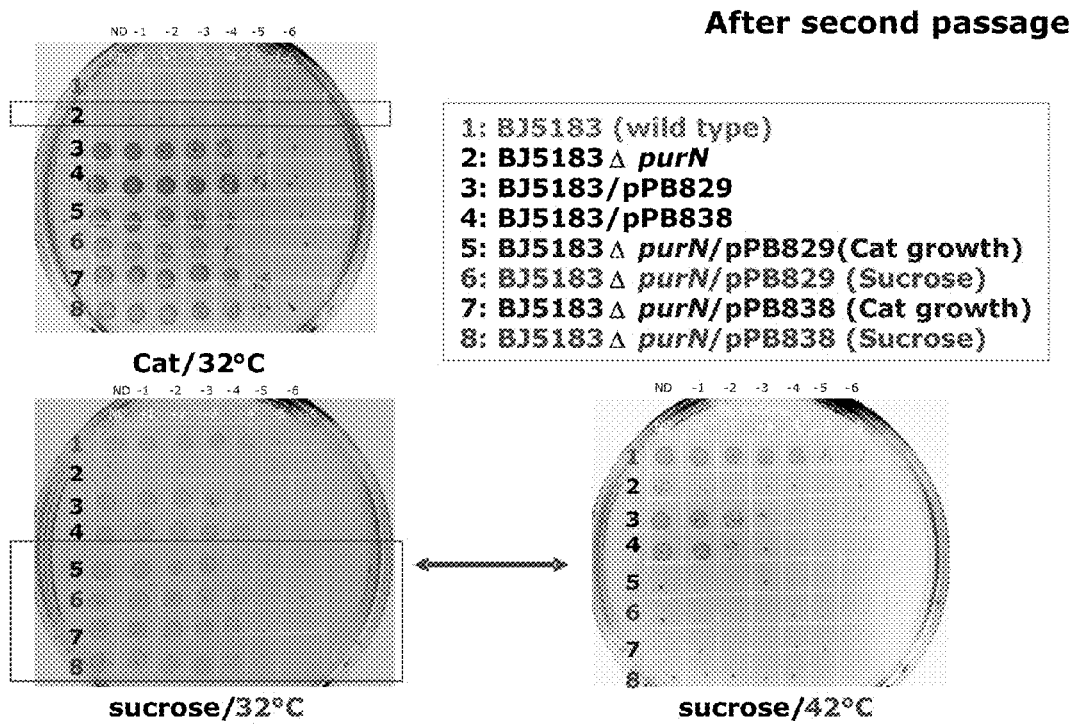
FIG. 10A demonstrates that the host strain (ΔpurN λPr::sacB$^+$Ωkan) is highly sensitive (no growth) to sucrose, that cells transformed either with pPB829 or pPB838 plasmid grew well in the presence of sucrose at 30° C., that sacB gene expression was perfectly repressed by the cI gene product synthesized from each cI plasmid and that the plasmid maintenance was 100% efficient as clearly demonstrated by the control experiment performed in parallel with similar cells growing in the presence of chloramphenicol. Raising the temperature to 42° C. caused inactivation of the cI gene product and death of the cells plated on LB agar containing either sucrose or chloramphenicol. The robustness of this plasmid maintenance experiments was performed after two successive passages of cells growing in the presence of sucrose or chloramphenicol.

The linear DNA fragment (λPr::sacB Ωkan) encoding a sacB gene placed under the control of λPr promoter (SEQ ID NO:75) and Kan resistance gene placed under the control of the bla promoter flanked by two long regions homologous to the DNA sequences bordering the target locus (edA or purN) was integrated into the chromosome of *E. coli* by electroporation. Approximately 300 transformant candidates (ΔpurN Ωkan or ΔedA Ωkan single mutant) were obtained on LB agar plate containing kanamycin as selection pressure. 20 colonies were randomly picked and purified by streaking on plates containing kanamycin and the λPr::sacB Ωkan cassette insertion at edA or purN locus was verified by PCR (see FIG. 9B). The PCR using the PB1196 and PB1197 was performed to check the Kanamycin insertion in the chromosome. The PCR using PB1192 and PB1193 was performed to verify the presence of the sacB gene in the chromosome. The PCR using PB1204 (SEQ ID NO:23) (GTGGTGCTTATTTCCG-GCAACGG) and PB1205 (SEQ ID NO:24) (CCAGC-CACGCGGCGTTTTCGTGC) primers was performed to verify the absence of purN gene in the chromosome. The PCR using PB1214 (SEQ ID NO:25) (GACCACCGGCCCGGT-TGTACCGG) and PB1215 (SEQ ID NO:26) (CGGAC-CCGCGATCGCCTGCAGG) was performed to verify the absence of edA gene) (see FIG. 9B). The PCR using PB1213 (SEQ ID NO:27) (GGTGGATGGCGTCCATTTCTGTGC) and PB1196 primers was performed to verify the right and correct insertion of the cassette at the edA locus. The PCR using the PB1212 (SEQ ID NO:28) (CAAAAGTGT-TAAGCGGTAACCTG) and PB1233 primers was performed to verify the left and correct insertion of the cassette at the edA locus. The PCR using PB1203 and PB1196 primers was performed to verify the right and correct insertion of the cassette at the purN locus. The PCR using the PB1202 and PB1233 primers was performed to verify the left and correct insertion of the cassette at the purN locus (see FIG. 9C). All the PCR checks confirmed the integration at the correct loci. Moreover the functionality of sacB gene has also been confirmed, as shown in FIG. 10. The engineered parental strain ΔpurN λPr:: sacB Ωkan was unable to grow on LB agar plate containing sucrose (FIG. 10).

The linear DNA fragment (λPr::sacB Ωcat) encoding a sacB gene (placed under the control of λPr promoter) and Cat resistance gene (placed under the control of its natural cat promoter) flanked by two long regions homologous to the DNA sequences bordering the target locus (edA) was integrated into the chromosome of the ΔpurN λPr:: sacB Ωkan *E. coli* strain by electroporation. Approximately 200 transformant candidates (ΔpurN λPr:: sacB Ωkan ΔedA λPr:: sacB Ωcat double mutant) were obtained on LB agar plate containing chloramphenicol as selection pressure. 20 colonies were randomly picked and purified by streaking on chloramphenicol and the λPr:: sacB Ωcat cassette insertion at the edA locus was verified by PCR (see FIG. 9C) using the primer set PB1212 and PB1213 (see FIG. 9C). The PCR product was checked by sequencing to validate the identity of the λPr::sacB Ωcat.

Host strain engineering is illustrated in FIG. 8D. FIG. 8E illustrates host strain (one sacB cassette [λPr:: sacB Ωkan]) and drugless plasmid coexistence. The initial *E. coli* genotype is Kan$^S$, Cat$^S$, Sucrose$^R$. Cassette integration into the chromosome of *E. coli* ΔpurN Prλ::sacBΩKan generated a new genotype, Kan$^R$, Cat$^S$, Sucrose$^S$. Introduction of the plasmid harboring the cI repressor generated the final genotype, Kan$^R$, Cat$^R$, Sucrose$^R$.

Example 3

Generation of Plasmids Harboring the cI Repressor Expression Cassette (Plasmids pPB838-pPB844 to pPB847-pPB885-pPB896)

Summary of Plasmid Construction

The pPB828-derived plasmids such as pPB829 and pPB844-pPB847 were generated containing the cI ORF of λ phage, under the control of either its own promoter or the weak promoter of the kanamycin gene (P1).

Figure 19:
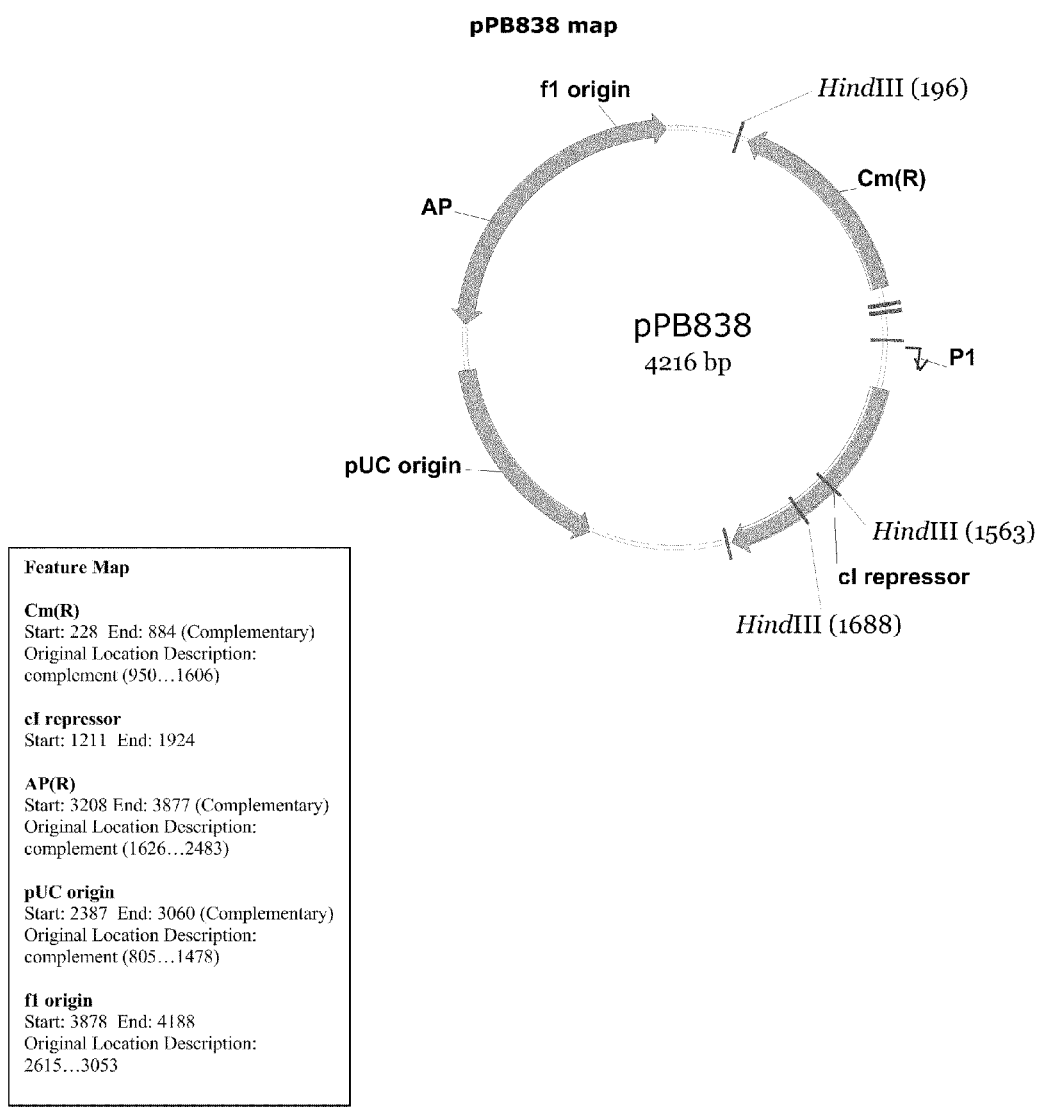
FIG. 19 shows the plasmid map and characteristics of pPB838.

The pPB838 plamid containing cI gene placed under the control of the weak promoter of Kanamycin gene (P1) was generated using an intermediate plasmid commercial vector pMCS5 in which chloramphenicol acetyl transferase gene (cat) replaced the ampicillin resistance gene. (FIG. 19).

Figure 20:
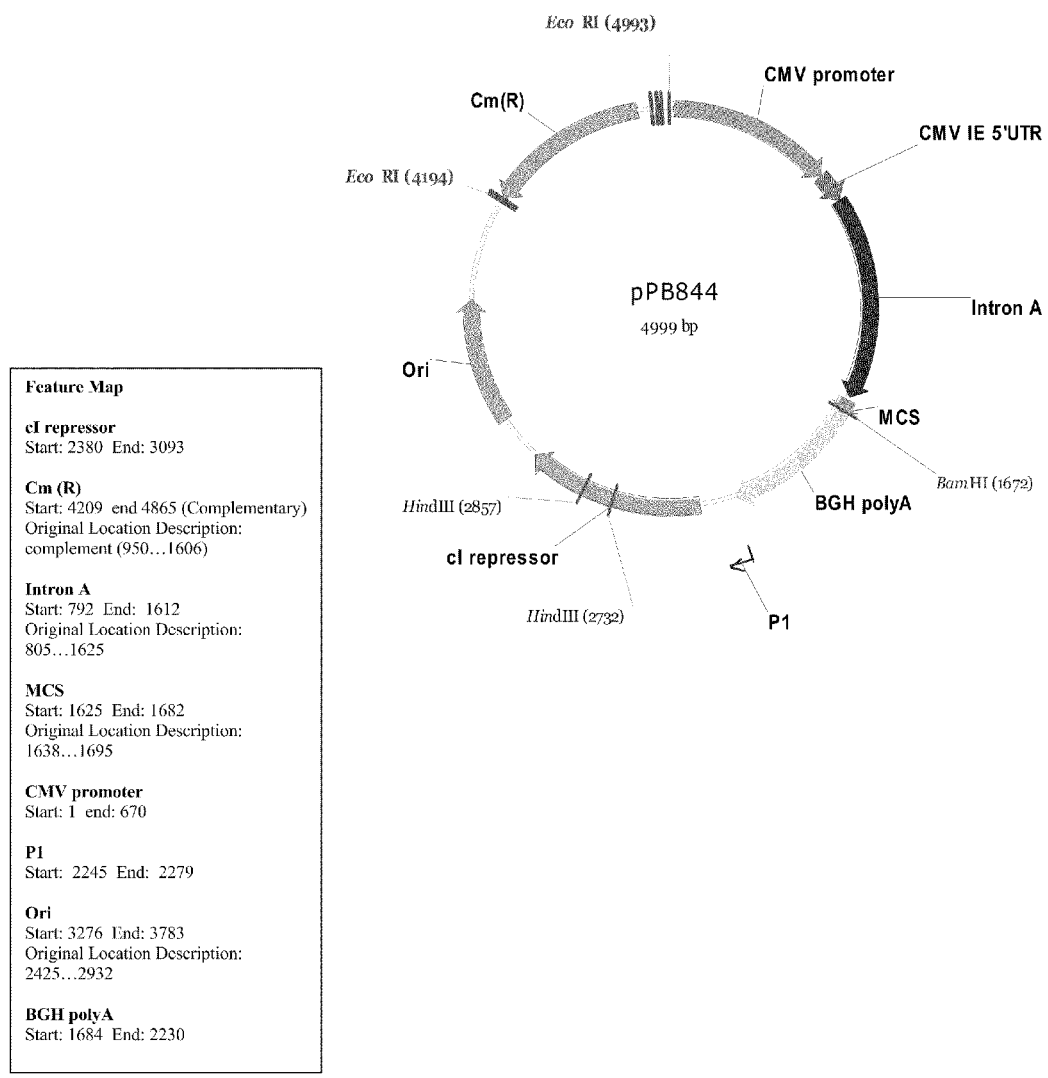
FIG. 20 shows the plasmid map and characteristics of pPB844.
Figure 21:
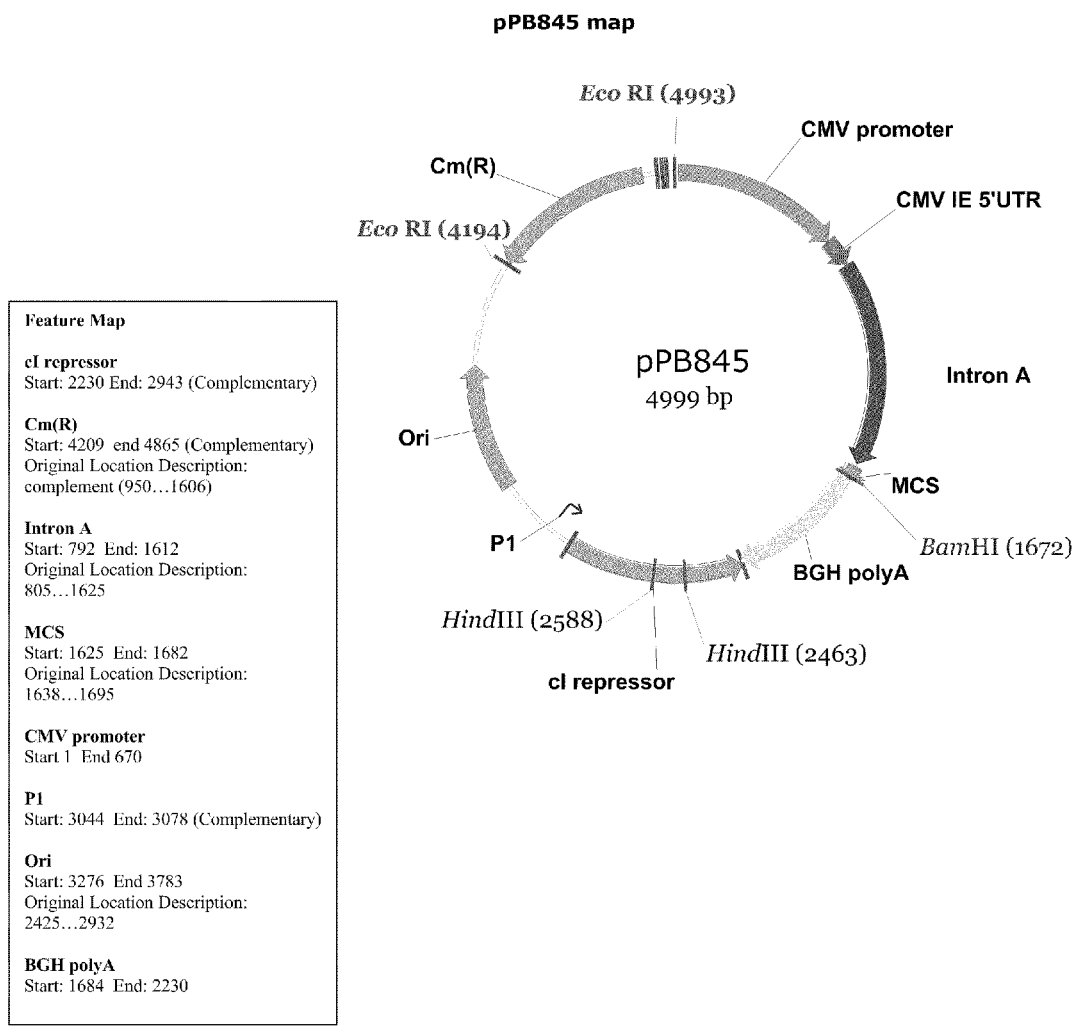
FIG. 21 shows the plasmid map and characteristics of pPB845.

The pPB844 and pPB845 plasmids contain the cI gene (placed under the control of the P1 promoter) cloned into the pPB828 vector which is a pVR1012 derivative (pVR1020 or 1012 plasmid, VICAL Inc.; Luke et al., 1997; Hartikka et al., 1996, see, e.g., U.S. Pat. Nos. 5,846,946 and 6,451,769) containing cat gene. The plasmids differ in the orientation of the cI gene into the plasmid (FIG. 20-21).

Figure 22:
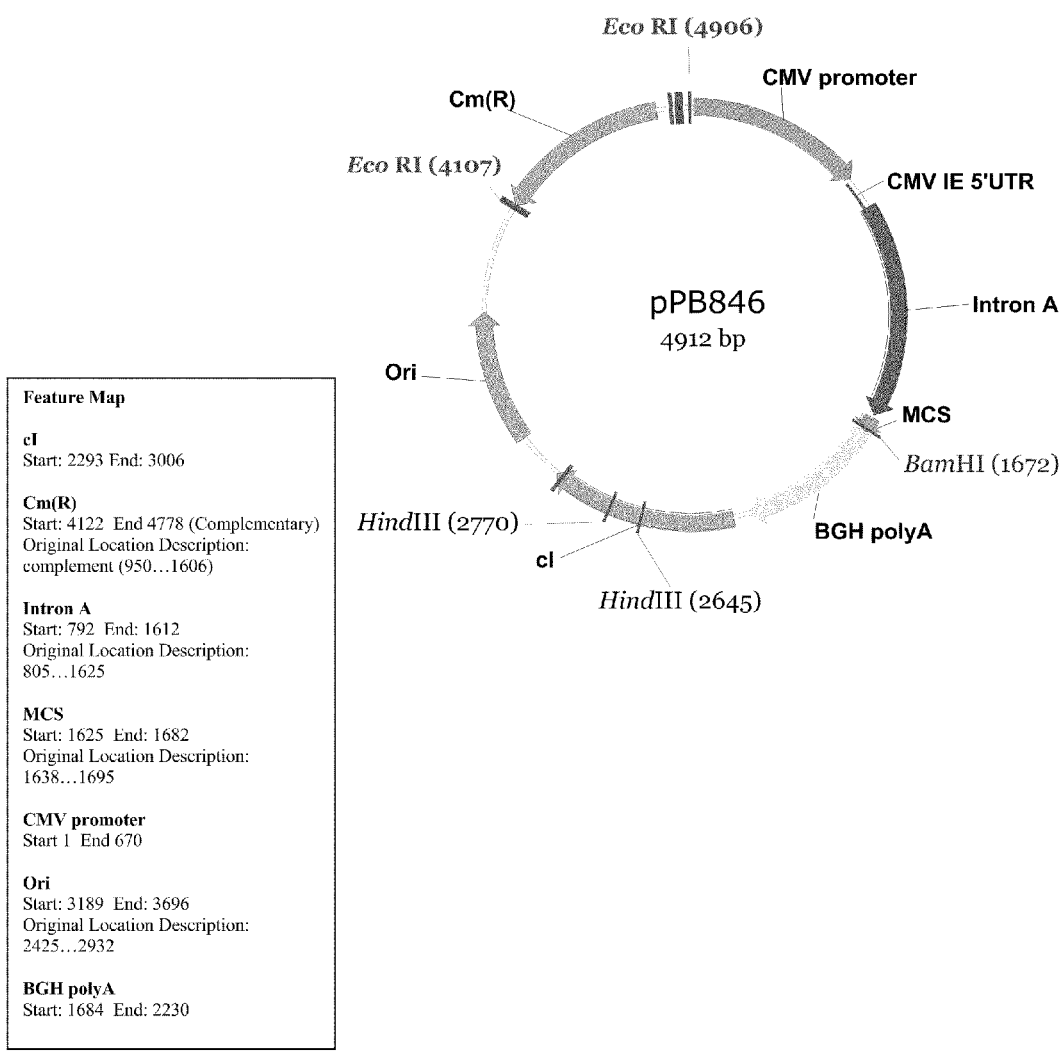
FIG. 22 shows the plasmid map and characteristics of pPB846.
Figure 23:
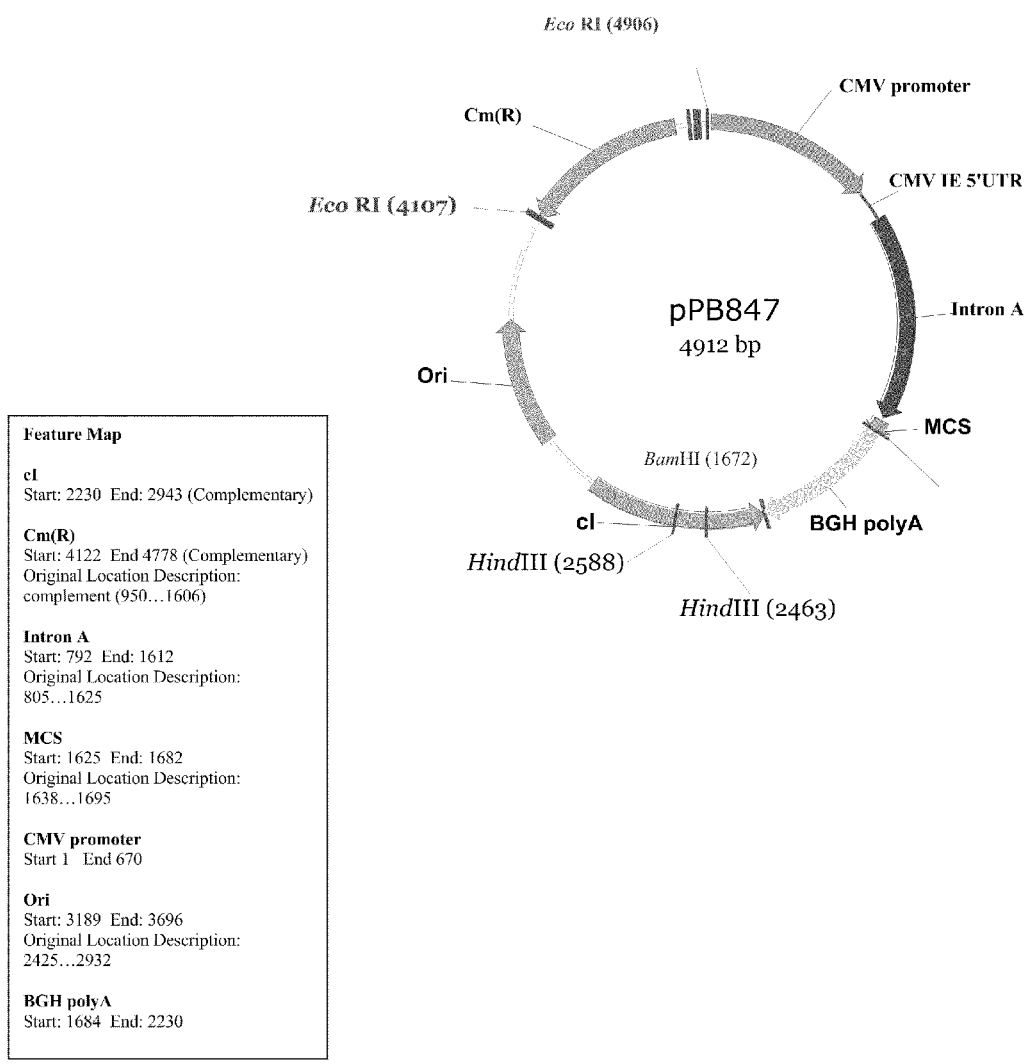
FIG. 23 shows the plasmid map and characteristics of pPB847.

The pPB846 and pPB847 plasmids contain the cI gene (placed under the control of its own (native) promoter SEQ ID NO:30) cloned into pPB828 vector which is a pVR1012 derivative containing cat gene. The plasmids differ in the orientation of the cI gene in the plasmid (FIG. 22-23).

Figure 24:
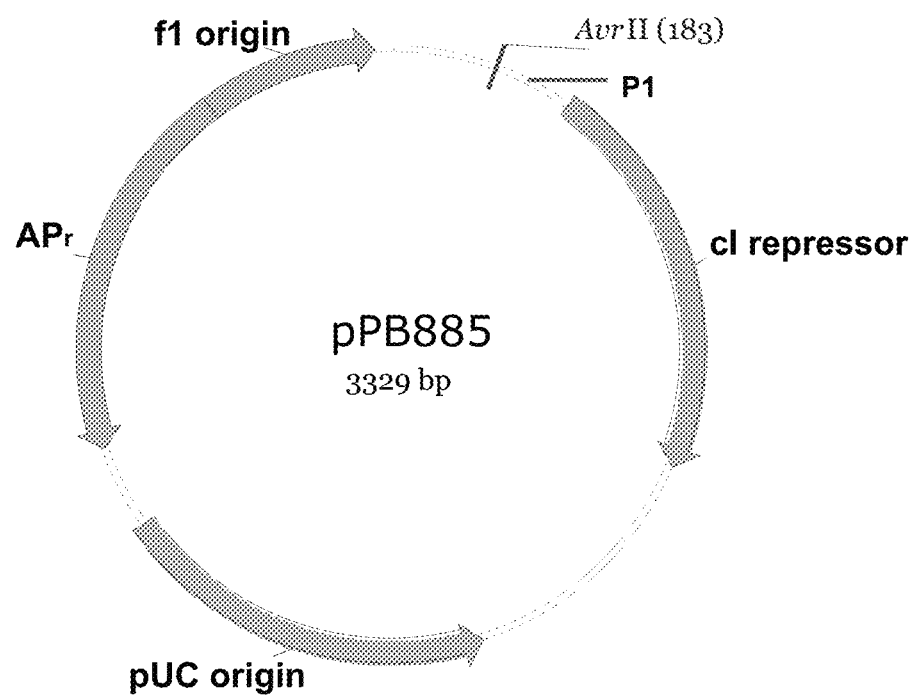
FIG. 24 shows the plasmid map of pPB885. The pPB885 feature map shows: two CDS: cI repressor: 324-1037; AP(R): 2321-2990 (complementary), original location (complement 1626.2483); two replication origin: pUC origin: 1500-2173 (complementary), original location (complement 805.1478); f1 origin: 2991-3301 (original location 2615-3053).

The pPB885 was prepared from the pPB838 plasmid [cI gene placed under the control of the weak promoter of Kanamycin gene (P1)] in which the chloramphenicol acetyl transferase gene (cat) was removed by AvrII restriction digestion (FIG. 24).

Figure 25:
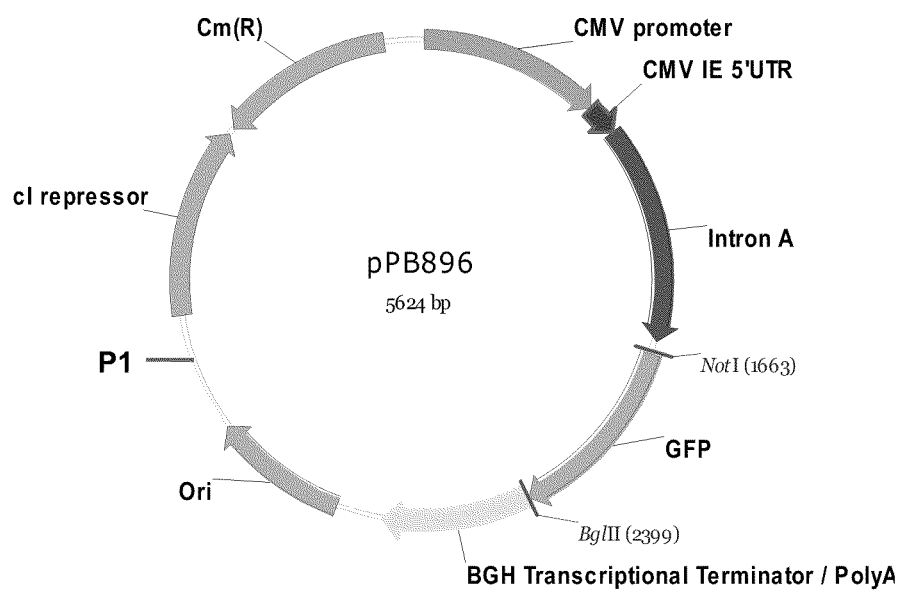
FIG. 25 shows the plasmid map of the pPB896. The pPB896 feature map shows: three CDS: GFP: 1675-2397 (original location 1676 . . . 2398); cI repressor: 4089-4802; Cm(R): 4828-5484 (complementary), complement (950-1606); one intron: intron A: 805-1625 (original location 805-1625); one eukaryotic promoter: CMV promoter: 1-683; one replication origin: 3133-3640 (original location 2425.2932); one terminator: BGH transcriptional terminator/PolyA: 2405-2951 (original location 1697.2243); one 5' UTR: CMV IE 5' UTR: 684-804 (original location 684.804).

The pPB829-derived plasmids such as pPB896 contains cI gene placed under the control of the weak promoter of Kanamycin gene (P1). The pPB896 plasmid contains the GFP marker gene placed under the control of the eukaryotic CMV promoter (FIG. 25).

These plasmids were used as vectors for cloning a heterologous polynucleotide, a gene of interest (transgene) in the drugless system. Each plasmid harbors the antibiotic resistance gene (cat) that can be excised and removed by a unique restriction enzyme to allow the plasmid propagation in the appropriate *E. coli* sacB$^+$ strain in the presence of sucrose without antibiotic selection pressure (such as chloramphenicol).

The antibiotic resistance gene (cat) on these plasmids was used only for proof of concept. The cat gene is finally removed in the final drugless plasmids (see FIGS. 13-15 and Example 4).

The cI gene sequence from plasmid pLDR8 (ATCC Number # 77357) produces a repressor protein cI857 mutant (NCBI: AB248924, Cloning vector pND707, Love, C. A. et al., Gene. 17; 176(1-2):49-53; 1996)

Figure 17:
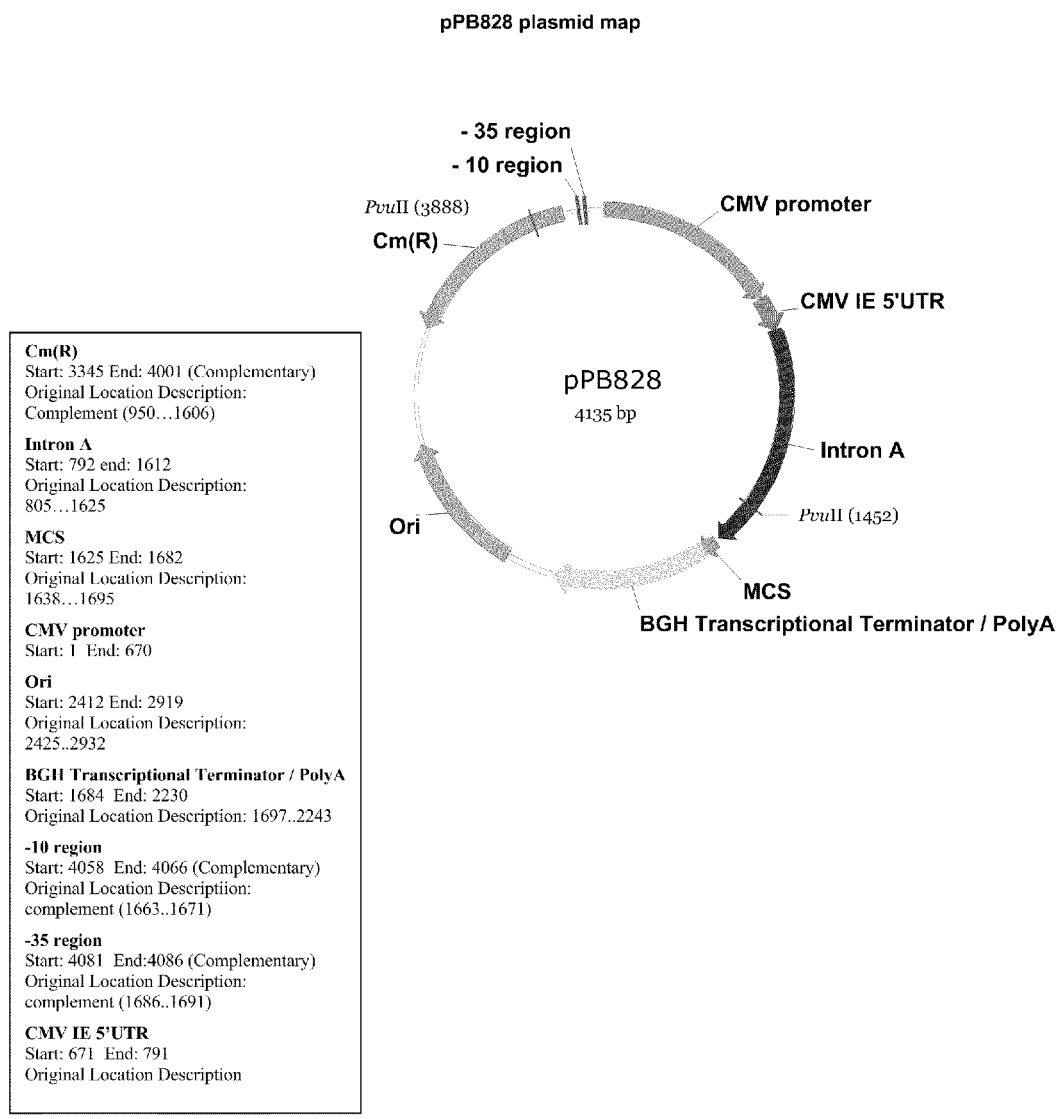
FIG. 17 shows the restriction map and characteristics of pPB828.

A. Construction of the Plasmid pPB829 Containing the cI Repressor ORF Placed Under the Control of the Weak Promoter P1 pPB828 Plasmid: (pVR1012-Based Plasmid+Cat Gene) (FIG. 17)

Figure 16:
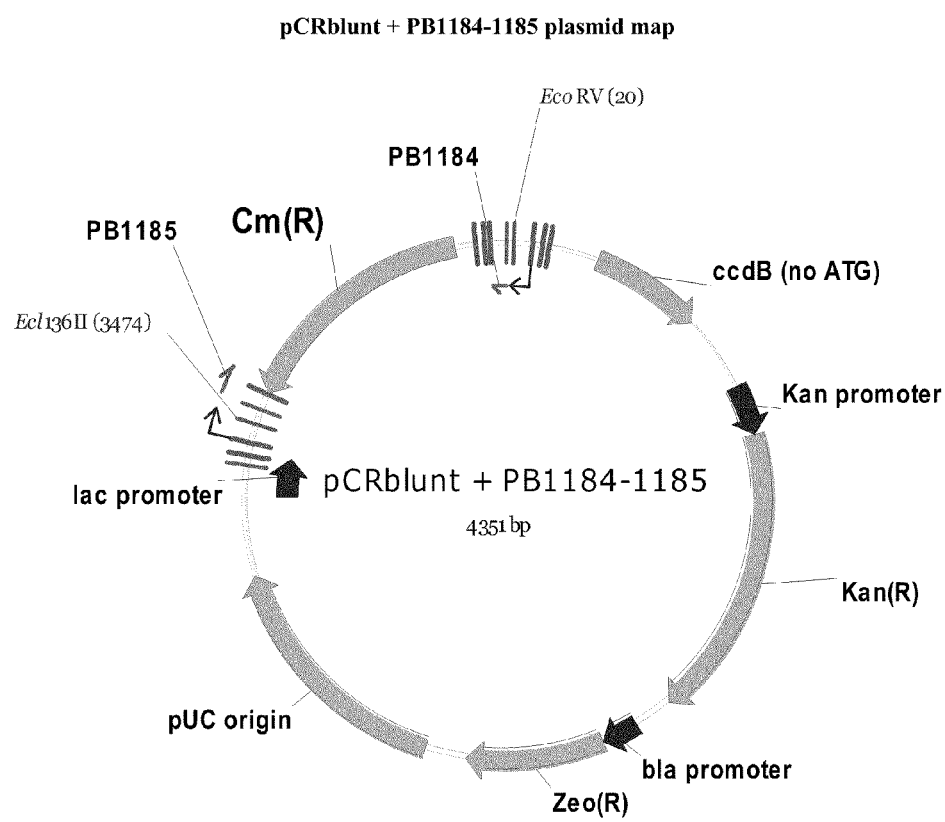
FIG. 16 shows the pCRblunt+PB1184-1185 plasmid map.
Figure 18:
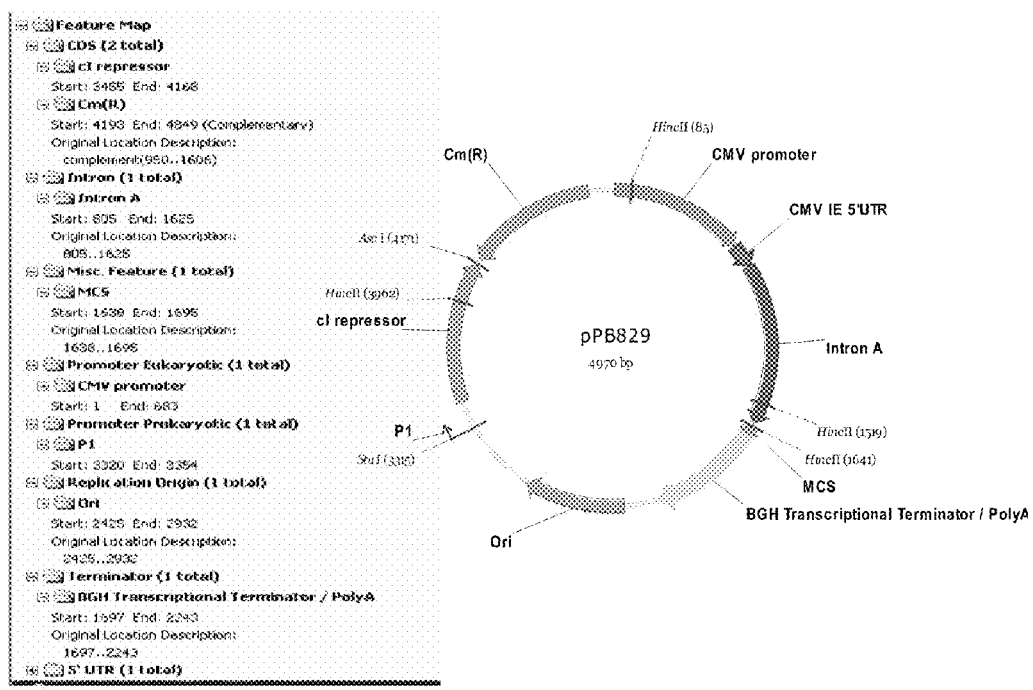
FIG. 18 shows the restriction map and characteristics of pPB829.

The pPB828-derived plasmids such as pPB829 was generated containing the cI ORF of λ phage, under the weak promoter of the kanamycin gene (P1) and the Cat gene that is excisable by a unique EcoRI digestion site. A pVR1012-based expression vector was generated containing the chloramphenicol acetyl transferase (cat) gene giving rise to the pPB828 plasmid. The cat gene from pPB627 (Merial proprietary material) was a derivative from pNB335 (Merial proprietary material) which is itself a derivative from initial plasmid pSW23T (cloning plasmid for GenBank Accession No. AY733066). The DNA fragment corresponding to the cat gene (798 bp) (SEQ ID NO:31 for DNA, SEQ ID NO:32 for protein)was obtained by PCR using the primers PB1184 (SEQ ID NO:33) (GAATTCCGG-TCCGGGCGAAAATGAGACGTTGATCGGC3) [Containing an EcorI site (underlined)] and PB1185 (SEQ ID NO:34) (CCTAGGCTGTGTTAATTAAGGCGCGCC GAATTCCGGTCCGTTACGCCCCGCCCTGCC ACT-CATCGC) [containing an EcoRI site (underlined)], using pNB350 as a template and Phusion™ High-Fidelity DNA polymerase (Finnzymes, 02150 Espoo, Finland). The resulting PCR product (832 bp) was ligated into the pCR blunt Topo vector (Invitrogen, CA, USA) to obtain plasmid pCRblunt/PB1184-1185 (4351 bp) (FIG. 16). The identity of pCRblunt/PB1184-1185 was confirmed by restriction analysis (PvuII digestion). The DNA fragment corresponding to the Cat gene was obtained by enzyme digestion of pCRblunt/PB1184-1185 plasmid with Ecl136II and EcoRV. The 897 by fragment was ligated into the pVR1012-based plasmid, previously digested with MscI and StuI (3303 pb) to generate plasmid pPB828 (FIG. 17). The identity of pPB828 was confirmed by restriction analysis (PvuII and NcoI digestion to determine the size of the insert and EcoRI to verify that the gene cat is well removed).

pPB829 Plasmid: (pPB828 plasmid+P1:: cI Gene) (FIG. 18)

Figure 9A:
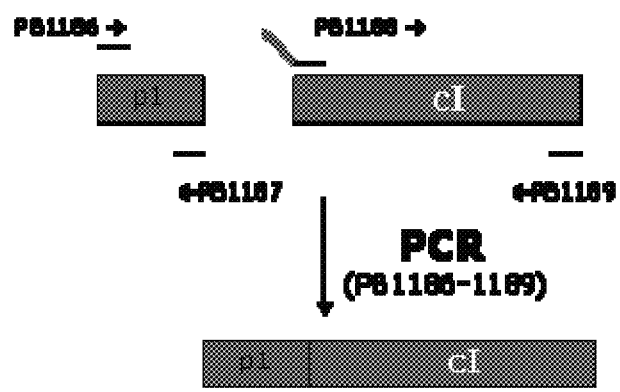
FIGS. 9A, 9B and 9C illustrate the use of PCR to demonstrate host strain engineering, namely the deletion of edA and purN in E. coli.

The construct containing the cI gene under P1 promoter (weak promoter of Kanamycin resistance gene) was obtained with a fusion PCR. The DNA fragment corresponding to the P1 weak promoter was obtained by PCR using primers PB1186 (SEQ ID NO:35) (TCATACCAGGCCTAGGT-GATACGCCTATTTTTATAGGTTAATG) and PB1187 (SEQ ID NO:36) (AACACCCCTTGTATTACTGTTTATG), using pLL14 (see Merial patent application US2005/0164946) as a template and Phusion DNA polymerase. The DNA fragment corresponding to the cI gene (SEQ ID NO:1) was obtained by PCR using primers PB1188 (SEQ ID NO:37) (AATACAAGGGGTGTTAT-GAGCACAAAAAAGAAACCATTAACAC) [containing a complementary region of P1sequence at 5' end (underlined)] and PB1189 (SEQ ID NO:38) (CCGGAATTCGGCGCGT-CAGCCAAACGTCTCTTCAGGCCACTG) using pLDR8 (ATCC # 77357) as a template and Phusion DNA polymerase. The two PCR products (respectively 151 and 729 bp) were purified and used as template in a second PCR step with the PB1186 and PB1189 primers and the Phusion DNA polymerase (Finnzymes, Finland) (see FIG. 24). The two PCR products (respectively 151 and 729 bp) were purified and ligated with plasmid pPB828 digested with AscI and AvrII to generate plasmid pPB829 (4970 bp) (FIG. 9A). The ligation was set up with the "In-Fusion PCR Cloning Kit" (cat. No. 740590.250) from Clontech (Takara Bio Europe, St-Germain-en-Laye, France). Clones pPB829 were selected following a HindIII digestion analysis. The integrity of the sequence of cI gene and P1 promoter was confirmed by sequencing the plasmid pPB829.

pPB896 Plasmid: (pPB829 Plasmid+P1::cI Gene+GFP) (FIG. 25)

The GFP marker gene was placed under the control of the eukaryotic CMV promoter (SEQ ID NO:43). The GFP gene was prepared from restriction digestion of the pCG105 plasmid (pPB828-derived plasmid having the GFP gene placed under the control of the eukaryotic CMV promoter, Merial proprietary material) with both NotI/BglII. This digested GFP gene was cloned into the pPB829 plasmid previously cut by NotI/BglII giving rise to the pPB896 plasmid.

B. Construction of the Intermediate Plasmid, pPB838, and Plasmids pPB844-pPB845, Containing the a Gene Under the P1 Promoter (Weak Promoter of Kanamycin Gene)

pPB837.1 Plasmid: (pMCS5 Plasmid+Cat Gene)

The DNA fragment corresponding to the Cat gene was obtained by PCR using the primers PB1182 (SEQ ID NO:39) (AGATCTGTTAA-CGGCGAAAATGAGACGTTGATCGGC) [containing a BglII site (underlined) at 5' end] and PB1183 (SEQ ID NO:40) (GTCGACGTTA-ACTTACGCCCCGCCCTGCCACTCATCGC) [contains a SalI site (underlined) at 5' end], using pPB791 [derivative of plasmid pNB350] as a template and Phusion DNA polymerase.

PCR primers were designed based on the cat sequence of pNB350. Three independent PCR products (779 bp) were pooled and ligated into the pCRII vector to obtain plasmid pCRII+PB1182-1183 (4734 bp). Clones of pCRII+PB1182-1183 were selected following a SalI/BglII digestion. The pMCS5 plasmid (MoBiTec, Germany) was digested with SalI and BglII in order to obtain the DNA fragment A (2950 bp). pCRII+PB1182-1183 was digested by SalI and BglII and fragment SalI-BglII was isolated from agarose gel (797 pb: fragment B). Fragments A and B were ligated to generate plasmids pPB837.1 (3747 bp).

pPB837.2: (pMCS5+Cat) without bla Promoter

Plasmid pPB837.2 was generated which does not contain bla promoter region. Plasmid pPB837.1 was digested with NaeI and XmnI and fragment NaeI-XmnI of 3300 by was isolated and purified from agarose gel (fragment A). The fragment A was ligated to obtain the pPB837.2 plasmid (3300 bp). Clone pPB837.2 was selected following a BgiI digestion.

pPB838 Plasmid (pMCS5+Cat without bla Promoter)+P1::cI (FIG. 22)

The construct containing the cI gene under P1 promoter (weak promoter of Kanamycin resistance gene) was obtained with a fusion PCR. The DNA fragment corresponding to the P1 weak promoter was obtained by PCR using primers PB1186 and PB1187, the pLL14 as a template and Phusion DNA polymerase. The DNA fragment corresponding to the cI gene was obtained by PCR using primers PB1188 and PB1189, the pLDR8 (ATCC # 77357) as a template and Phusion DNA polymerase (Finnzymes, Finland). The two PCR products (respectively 151 and 729 bp) were purified and used as templates in a second PCR step with the PB1186 and PB1189 primers and the Phusion DNA polymerase. Two independent PCR products (880 bp) were pooled and ligated into the pCRII blunt vector to obtain plasmid pCRblunt+PB1186-1189 (4400 bp). Clones of pCRII blunt+PB1186-1189 were selected following an EcoRV/SpeI digestion.

pCRII blunt+PB1186-1189 was digested with EcoRV and SpeI in order to obtain the EcoRV-SpeI fragment A (936 bp). pPB837.2 was digested with EcoRV and SpeI and fragment EcoRV-SpeI was isolated from agarose gel (3464 pb: fragment B). Fragments A and B were ligated to generate plasmids pPB838 (4216 bp). Clone pPB838 was selected following a HindIII digestion. The integrity of the sequence of cI gene and P1 promoter was confirmed by sequencing.

pPB885 Plasmid (pMCS5+Cat without bla Promoter)+P1::cI (FIG. 24)

This plasmid was deprived from pPB838 plasmid where the chloramphenicol acetyl transferase gene (cat) was removed by AvrII restriction digestion (FIG. 24). pPB885 plasmid contains the cI gene under the control of the weak promoter of kanamycin gene (P1). The pPB885 plasmid was isolated as described in the example 4 (see below) following transformation of the ΔpurN λPr::sacB Ωkan E. coli host strain by direct selection on LB agar plate supplemented with 10% sucrose.

Plasmids pPB844-pPB845 (FIGS. 23-24)

The DNA fragment corresponding to the cI gene under P1 promoter was obtained by PCR using primers PB1186 and PB1263 (SEQ ID NO:41) (TCAGCCAAACGTCTCT-TCAGGCCAC), the pPB838 plasmid as a template and Phusion DNA polymerase. Four independent PCR products PB1186-PB1263 (864 bp) were pooled and ligated into the pCRblunt vector to obtain plasmid pCRblunt+PB1186-1263 (4383 bp). Clones of pCRblunt+PB1186-1263 were selected following a HindIII digestion.

The pCRblunt+PB1186-1263 plasmid was digested with EcoRI and the extremities were filled with Klenow Polymerase to generate a blunt fragment (929 by: fragment A). The pPB828 plasmid was digested with XmnI and the resulting XmnI-XmnI fragment was purified (fragment B: 4135 bp). Fragments A and B were ligated to generate plasmids pPB844 or pPB845. Candidates were screened by a BamHI/HindIII digestion. In the pPB844 plasmid (see FIG. 20), the cI gene is in the same direction as the transgene of interest to be cloned into the MCS (multiple cloning site) of the vector under the control of the CMV promoter (SEQ ID NO:43). In the pPB845 plasmid (see FIG. 21) the cI is oriented in the opposite direction.

C. Obtaining the cI Gene with its Native Promoter Plasmids pPB846-pPB847

The DNA fragment corresponding to the cI gene under its own promoter (cI native promoter: SEQ ID NO:30) was obtained by PCR using primers PB1266 (SEQ ID NO:42) (GCTGACTCATACCAGGCACGCACGGTGT-TAGATATTTATCCC) and PB1263, using pLDR8 plasmid as a template and the Phusion DNA polymerase.

pPB846-pPB847 Plasmids

Four independent PCR products PB1266-PB1263 (777 bp) were pooled and ligated into the pCRblunt vector to obtain plasmid pCRblunt+PB1266-1263 (4296 bp). Clones of pCRblunt+PB1266-1263 were selected following a HindIII digestion.

The pCRblunt+PB1266-1263 plasmid was digested with EcoRI and the extremities were filled with Klenow Polymerase to generate a blunt fragment (842 by: fragment A). pPB828 plasmid was digested with XmnI and fragment XmnI-XmnI was purified (fragment B: 4135 bp). Fragments A and B were ligated to generate plasmids pPB846 (4999 bp) or pPB847. Candidates were screened by a BamHI/HindIII digestion. In the pPB846 plasmid (see FIG. 22), the cI gene is in the same direction as the gene of interest to be cloned into the MCS site of the vector under the control of the CMV promoter. In the pPB847 plasmid (see FIG. 23), the cI gene is oriented in the opposite direction.

D. Construct Results

Figure 7:
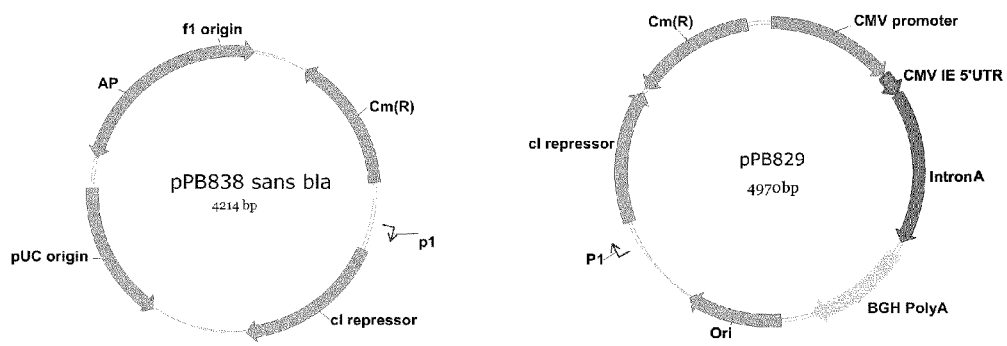
FIG. 7 describes both plasmids (pPB829 and pPB838) marked with the genes encoding chloramphenicol acetyl transferase (Cat$^R$) and containing the λcI gene. pB838 is a derivative of pMCS5 in which Chloramphenicol acetyl transferase gene (cat) replaces the ampicillin resistance gene. This plasmid contains the cI gene placed under the control of the weak promoter of Kanamycin gene (P1). pPB829 is a pVR1012 plasmid derivative containing the cat gene. The plasmids contain the cI gene which is placed under the control of the weak promoter (P1). When introduced in the ΔpurN (or ΔedA) parental *E. coli* strain, these plasmids will enable the cells to grow in the presence of sucrose. Chloramphenicol allows demonstration of the proof of concept.

FIG. 7 shows the constructs of pPB838 and pPB829 harboring the cI repressor that were used to prepare the drugless plasmid. Both plasmids were marked with the Chloramphenicol (Cat$^R$) gene. The Cat gene on these plasmids were required only for determining proof of concept but can be finally removed (see FIGS. 13-15 and Example 4).

Example 4

Transformation of the E. Coli Host Strain with the cI Plasmid(s) and Direct Selection on a Sucrose Agar Plate An experimental procedure that enables the screening of the transformed cells by the chloramphenicol (Cat) marked cI plasmid(s) without the use of antibiotic as selection pressure on agar plate(s) has been efficiently demonstrated (see FIG. 13-15). Competent cells of E. coli λPr::sacB$^+$ΔpurNΩKan were transformed with 1 μg of either pPB838 or pPB829 plasmid and incubated for 3 hours at 30° C. in LB liquid broth medium. 100 μl aliquot of diluted ($10^{-3}$ and $10^{-4}$) transformed cells (with pPB838 and pPB829 plasmids) were spread onto LB agar plate containing 10% sucrose. These dilutions ranging from $10^{-3}$ to $10^{-4}$ appear appropriate to select true transformant cells (e.g. having cI plasmid) since 98-100% of sucrose resistant cells growing on LB agar plate containing sucrose were Cat$^R$. This suggests that these transformed cells have the cI plasmid (pPB829 or pPB838).

Figure 13A:
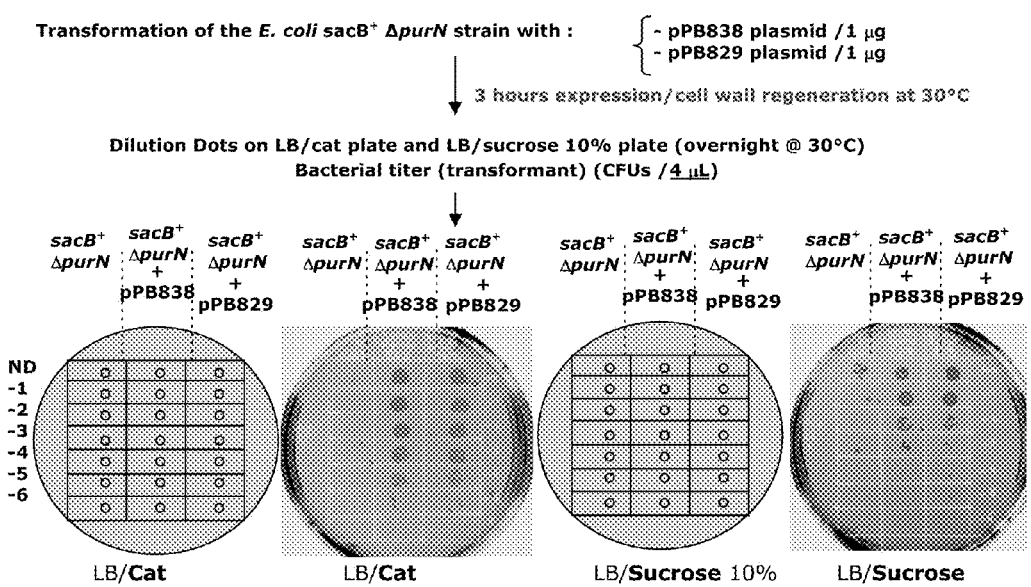

FIG. 13A shows that competent cells of E. coli λPr::sacB$^+$ ΔpurNΩKan were transformed with 1 μg of either pPB838 or pPB829 plasmid and incubated for 3 hours at 30° C. in LB liquid broth medium before dot-spotting (4 μl for each dot). The figure shows the Log dilutions (ranging from undiluted to 6 Log dilution) on LB agar plates containing either chloramphenicol (15 μg/ml) or sucrose (10%). The untransformed competent parental strain cells of E. coli λPr::sacB$^+$were used as standard cells grown under similar condition. As expected, the standard cells did not grow on selective plates such as cat and sucrose. Nevertheless, due to the long period of incubation (3 days), some spontaneous mutant resistant to sucrose appeared under this condition. This level of spontaneous mutant defines a baseline to be considered for the screening of true transformant cells. Two Log differences were observed with transformed cells growing on cat and sucrose under this experimental condition. Competent cell, per definition, presents a temporally of cell wall weakness. The post-electroporation incubation of transformed cells in LB liquid medium enables the regeneration of both the aforementioned cell wall weakness and the induced-pores of the cell wall and cell membrane following electroporation. Since the competent cells were genetically sensitive to sucrose due to the λPr:: sacB$^+$ΔpurNΩKan cassette insertion, the transformed cells recovery in the presence of sucrose was reduced by two Logs compared to the cells recovery on Cat. These observations were confirmed by spreading 100 ul of transformed cells on selective plates (see FIG. 13B).

FIG. 13B shows that 100 μl of transformed (with pPB838 and pPB829 plasmids) and untransformed standard cells were spread on selection LB agar plate containing either cat or sucrose using appropriate Log dilution to determine the rate of transformation efficacy on cat and sucrose and standard spread on sucrose to better define the baseline of spontaneous mutant rate to be considered for successful screening of true transformant cells capable of growth on LB sucrose agar plate. In agreement with the previous dot-spotting cells experiment (see FIG. 13A), spontaneous mutant resistant to sucrose were not detectable when the $10^{-3}$ dilution of transformant cells were spread on LB agar plate containing sucrose. As previously shown (see FIG. 13A), there was 2 Logs difference in the transformation efficacy between selection on cat and sucrose under this condition. The dilutions ranging from $10^{-3}$ to $10^{-4}$ when spread on LB agar containing sucrose appeared appropriate to select true transformant cells (e.g. having cI plasmid).

Figure 14A:
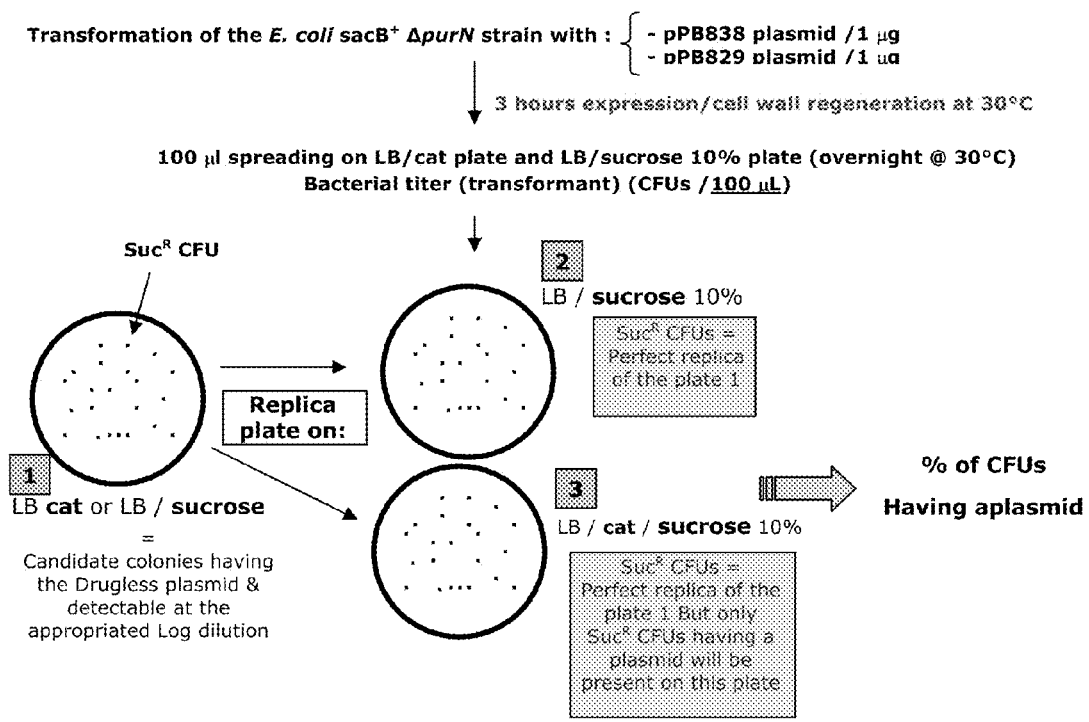
Figure 14B:
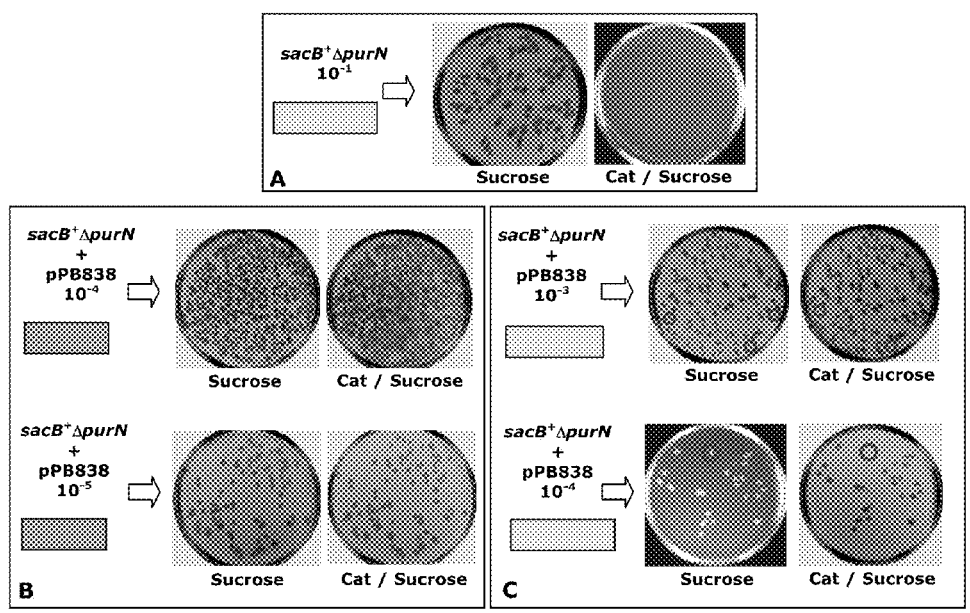

FIGS. 14A-C illustrate the efficacy of the experimental procedure to select transformed cells with the cI plasmid only (pPB829 and pPB838) without the use of antibiotic as selection pressure.

FIG. 14A shows the experimental overview using replica plate assay to validate the screening of true transformant cells having the cI plasmid. Similar to what is shown in FIG. 13B, parental competent cells λPr::sacB⁺ΔpurNΩKan were transformed with the cI plasmid (pPB829 and pPB838) and appropriate Log dilutions were spread onto selective (Cat or Sucrose) LB agar plates before incubation for 3 days at 30° C. Afterwards, the plates showing CFUs (colony forming units) titers ranging from 20 to 150 were replicated on new fresh LB agar plates containing either Cat or sucrose or a combination of both before incubation for 3 more days at 30° C. In theory, Cat resistant colonies should correspond to cells propagating the cI plasmid(s).

FIG. 14B shows that experimental results confirmed that the Cat$^R$ CFUs were identical between the number obtained on sucrose LB agar plates and on Cat/sucrose LB agar plates after replica plate assay. As demonstrated in FIG. 14B (panel B), the CatR CFUs are i) all sucrose resistant and ii) all resistant to the combination of Cat and Sucrose, signifying that all parental cells following transformation harbor the cI plasmids. Panel C shows that the $10^{-3}$ and $10^{-4}$ dilutions of transformant cells selected directly on sucrose were also resistant to sucrose and to the combination of both sucrose and Cat, also signifying that these sucrose resistant CFUs correspond to true transformed cells containing the cI plasmid. Indeed, when non transformed parental cells were spread onto LB agar plate containing sucrose, the sucrose resistant CFUs when replicated on a combination of sucrose and Cat did not grow as expected because the chloramphenicol resistance is a phenotypical trait brought by either the pPB829 or pPB838 plasmid.

FIG. 14C represents the statistical data obtained from the replica plate assay (see FIG. 14B) and more particularly the percentage of the colonies having the cI plasmid that were selected without the use of antibiotic. Under this experimental condition, the percentage of colonies having the cI plasmid ranges from 98% to 100%.

Example 5

Different Culture Conditions with and without Sucrose Showing that the cI Plasmid can be Maintained E. coli cells expressing sacB, ΔpurN λPr::sacB⁺ΩKan were grown in the presence or absence of sucrose in order to check the functionality of the ΔPr::sacB⁺cassette inserted into the chromosome of E. coli.

Figure 4:
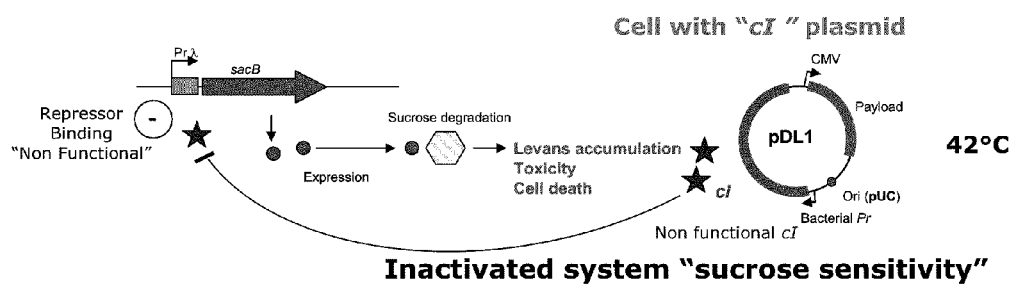
FIG. 4 describes the "sucrose sensitivity" of the inactivated system wherein a switch to 42° C. in temperature inhibits the binding activity of cI repressor to the λPr promoter and renders the host cells sensitive to sucrose.
Figure 5:
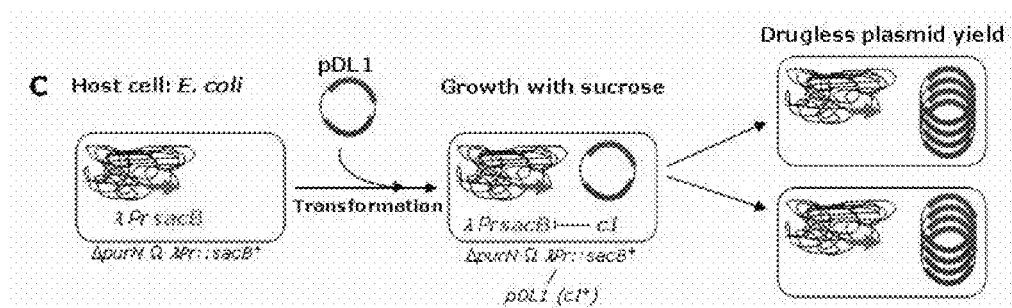
FIG. 5 illustrates the combination of the host strain with the antibiotic-free pDL1 plasmid, resulting from the transformation with pDL1, and growth in medium containing sucrose leading to drugless plasmid yield.

FIG. 4 describes the "sucrose sensitivity" of the inactivated system wherein a switch to 42° C. in temperature inhibits the binding activity of cI repressor to the λPr promoter and renders the host cells sensitive to sucrose. The cI repressor protein, expressed from the plasmid, inhibits the transcription of the toxic sacB gene product placed under the λPr promoter that is located on the host cell chromosome. The host E. coli cells' viability in the presence of sucrose is ensured by a sufficient expression level from the plasmid of the λcI repressor protein. FIG. 5 describes the combination of the host strain with the antibiotic-free pDL1 plasmid in the presence of sucrose to yield drugless plasmid (pDL: DrugLess Plasmid). The experimental plan for the proof of concept is further illustrated in FIGS. 6A, 6B, and 6C.

The physiological characteristics of host cells expressing sacB, ΔpurNΩλPr::sacB⁺Ωkan when grown in the presence or absence of sucrose are described in Table 1.

TABLE 1

The physiological characteristics of sacB⁺ host cells, ΔpurN Ω λPr::sacB⁺, when grown with sucrose and without sucrose

|  | Sucrose | Viability/Growth |
| --- | --- | --- |
| Wild type | − | + |
| purN⁺ (sacB⁻) | + | + |
| Host strain | − | + |
| ΔpurN Ω λPr::sacB⁺Ωkan | + | − |

The physiological characteristics of host cells expressing sacB (λPr::sacB⁺), with and without pDL1 plasmid when grown in the presence or absence of sucrose, are described in Table 2.

TABLE 2

The physiological characteristics of (λPr::sacB⁺ host cells with and without pDL1 plasmid when growing with sucrose and without sucrose.

| Sucrose | SacB | pDL1 plasmid | Viability/Growth |
| --- | --- | --- | --- |
| − | + | − | YES |
| − | + | + | YES |
| + | + | − | NO |
| + | + | + | YES |

Figure 11:
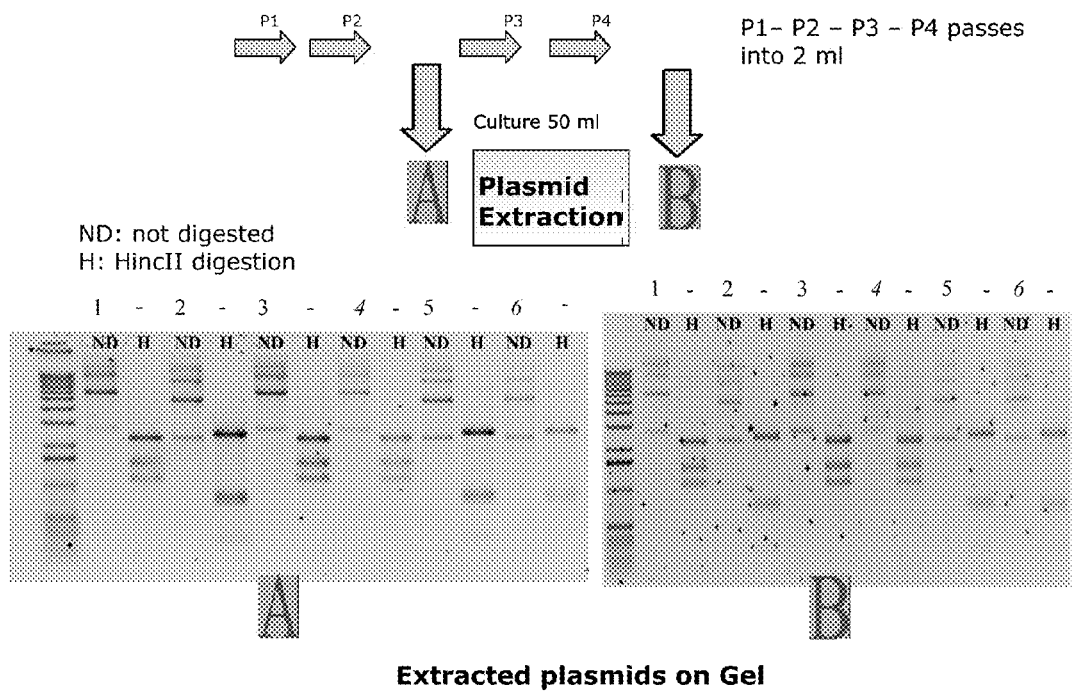
FIG. 11 illustrates the stability of the pPB829 and pPB838 plasmids in growing cells.

FIGS. 10-11 provide results confirming that the genetically engineered host strains were highly resistant to sucrose at 30-37° C., while no growth was observed at 42° C. FIG. 10 shows that second passage with the E. coli host strains, ΔpurN λPr::sacB⁺Ωkan, harboring either the pPB829 plasmid or pPB838 plasmid grew well in the presence of sucrose at 32° C. The sacB gene expression was perfectly repressed by the cI gene product synthesized from both cI plasmids. The plasmid maintenance was 100% efficient (versus control on Cat$^R$) and cells were able to survive in the presence of sucrose. At 42° C., the cI gene product was inactivated. The plasmid could not be maintained and the cells died in the presence of sucrose. This demonstrates that the cells viability in the presence of sucrose was due to the presence of a functional cI plasmid.

Example 6

Culture Conditions Showing that the cI Plasmids are Stable Over 5 Passages, without Antibiotic Selection Pressure, and Lack of Spontaneous Mutants for Sucrose Resistance Once the drugless plasmids were produced, they were tested for stability and their robustness over several passages in fresh broth medium containing either sucrose or Cat.

FIG. 11 illustrates the stability of the pPB829 and pPB838 plasmids in growing cells, including lack of obvious genetic rearrangement during selection on either chlorampenicol or sucrose. Comparable plasmid yields and maintenance in cultures growing in the presence of sucrose and chloramphenicol were observed even after five successive passages. The antibiotic and non antibiotic systems were at least equivalent in terms of plasmid maintenance and selection from growing cells.

Figure 12A:
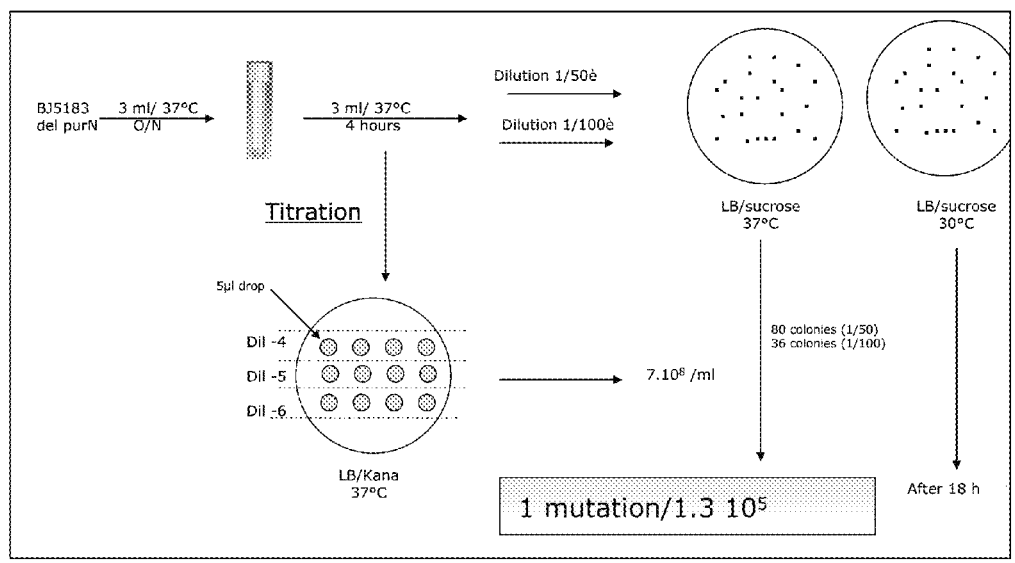
FIG. 12A shows a lack of spontaneous mutation in the λPr::sacB one sacB cassette at 30° C.

FIG. 12 illustrates the lack of spontaneous mutations in the λPr:: sacB cassette inserted in the parental E. coli strain when cells were growing at 30° C. This observation clearly demonstrates the cI plasmid stability in such E. coli genetic background when cells were growing in presence of sucrose (see FIG. 10). This mutation rate experiment was performed with the parental strain (purN deleted expressing the sacB gene). It was shown that no mutation occurred at 30° C. after 18 h incubation. Clonal cultures of parental cells harboring the sacB cassette in their chromosome were grown in LB containing sucrose. Cells were harvested at an OD of 1.0 and aliquots of 100 μL were spread onto LB agar plates containing sucrose. Since the presence of the sacB gene causes the cells death, the spontaneous mutation rate was evaluated by scoring the sucrose resistant colonies after overnight incubation at 30° C. Standard cells harboring the sacB cassette but transformed with the cI plasmid (pPB829 or pPB838) became resistant to sucrose and culture of DO 1.0 needed to be diluted by 5 Log before being spread (100 uL) onto LB agar plates supplemented with sucrose for scoring. Following the overnight culture (18 hours incubation), no sucrose resistant colony was detected with the parental cell cultures (ΔpurN-λPr::sacBΩkan) while the 5 Log diluted cultures of ΔpurN-λPr::sacBΩkan transformed with the pPB829 or pPB838 plasmid(s) grew. Thirty-six hours were required to detect some sucrose resistant colonies (ΔpurNλPr::sacBΩkan) when the cells were incubated at 37° C.

Spontaneous mutation occurred at a rate of 1 mutation/1.3× $10^5$ cells after 36 hours when incubated at 37° C. The cI plasmid maintenance in the cells growing in the presence of sucrose was effective after overnight incubation at 30° C. while no growth of the mother strain was detected.

Example 7

Improvement of the Parental E. Coli Host Strain to Reduce the Rate of the Spontneaous Mutation to Sucrose by Adding a Second sacB Cassette (ΔedAλPr::BΩcat) into the Aforementioned one sacB Cassette E. Coli Host Strain (ΔpurN λPr::sacBΩkan).

Figure 9D:
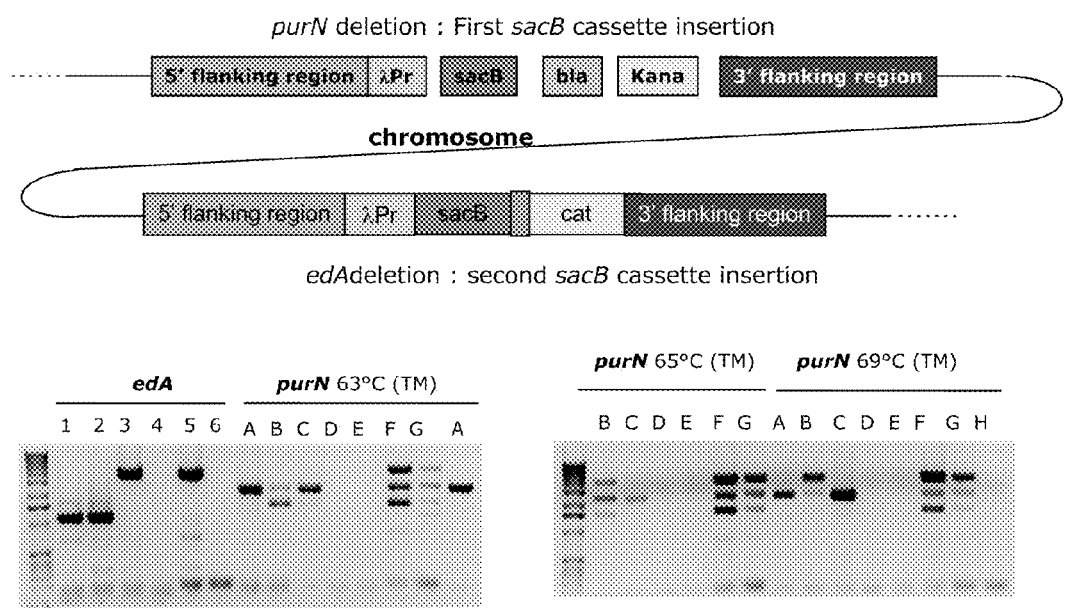
FIG. 9D illustrates the use of PCR to demonstrate the dual sacB cassette host strain engineering, namely the deletions of both edA and purN in E. coli by allelic replacement. The PCR check shows that both λPr::sacB$^+$ΩKan and λPr::sacB$^+$ΩCat cassettes are correctly introduced at the specific loci into the chromosome of E. coli, as confirmed by sequencing.

Both FIG. 8C and FIG. 9D illustrate how the new parental host strain of E. coli harboring two sacB cassettes (ΔpurN λPr::sacBΩkan ΔedA λPr::sacBΩcat) were engineered.

FIG. 10B-C demonstrate that the dual sacB cassettes E. coli strain (ΔpurN λPr::sacB$^+$Ωkan ΔedA λPr::sacB$^+$ΩCat) was highly sensitive (no growth) in the presence of sucrose when incubated at 30° C. and 42° C. while some spontaneous mutants appears with the one sacB cassette E. coli strain plated on even 10% sucrose (ΔpurN λPr::sacBΩkan).

FIG. 10C also illustrates that the lowest sucrose concentration required (2% final) for the dual sacB cassettes E. coli strain compared to the one sacB cassette E. coli strain (10% final). Moreover, it appears that the two sacB cassettes E. coli strain was much more sensitive to sucrose, as shown at low sucrose % and at the highest temperature such as 42° C. This suggests that temperature at about 37° C. and sucrose concentration at about 2% (or slightly below) may correspond to the optimal condition for maintaining the plasmid(s) harboring the cI gene repressor in growing cells.

Figure 12C:
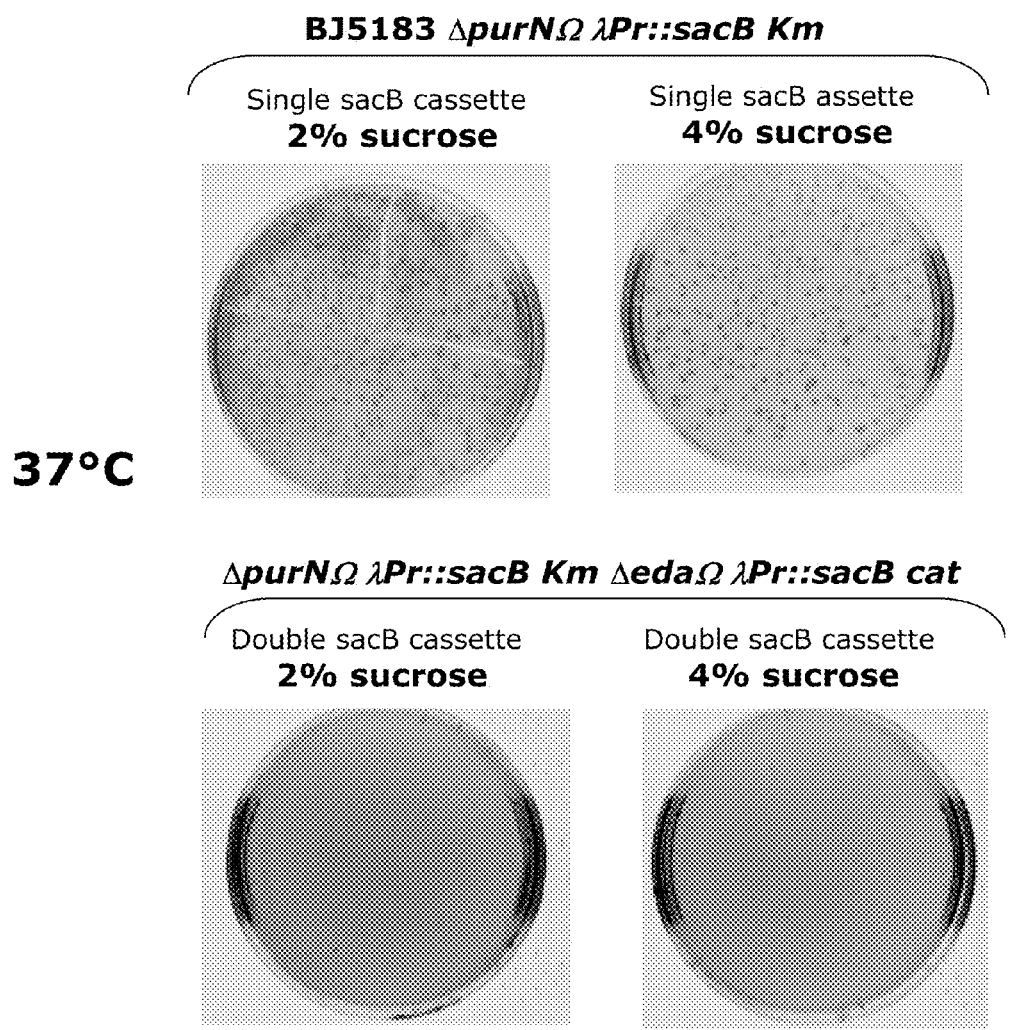

FIG. 12B-C demonstrate that the presence of two sacB cassettes (rather than one) confers a better robustness to sucrose sensitivity (still optimal at 2% sucrose) at temperatures ranging from 30° C. to 37° C. The E. coli cells transformed with plasmids containing two sacB cassettes BJ5183 ΔpurNΩPr:: sacB Km ΔedaΩλPr:: sacB Cat clone #1 and BJ5183 ΔpurNΩλPr:: sacB Km ΔedaΩλPr:: sacB Cat clone #2, and E. coli cells transformed with plasmids containing one sacB cassette BJ5183 ΔpurNΩλPr:: sacB Km clone #16 and BJ5183 ΔedAΩλPr:: sacB Km clone #11 were grown to OD600 about 1.0. About 100 ul of each culture was spread onto LB/agar plates containing 0%, 2% and 4% sucrose (dilution 1e) for CFU scoring. The plates were incubated at 30° C. to 37° C. Incubation at 37° C. was used to evaluate the robustness of the parental strain expressing the dual sacB cassettes in the presence of 2% and 4% sucrose. FIG. 12B-C and Tables 3-7 below show that the presence of one sacB cassette in the E. coli chromosome was less robust at sucrose concentration ranging from 2 to 4% at similar temperatures such as 30° C. and 37° C. As confirmed in this plating assay, the mutation rate to sucrose with the two sacB cassettes E. coli strain was undetectable at the lowest sucrose concentration (2%) when incubated at 37° C. while the mutation rate with the one sacB cassette E. coli strain was ranging from $3.8\ 10^{-6}$ to $5\ 10^{-5}$. An independent set of experiment showed that the mutation rate in the two sacB cassettes E. coli strain was nearly $5.10^{10}$ when incubated at 37° C. in presence of 2% sucrose.

TABLE 3

| | Number of colonies ($10^{-5}$ dilution) LB/agar 0% sucrose | |
|---|---|---|
| | 37° C. | cell titer/ml |
| 1* | 200 | $2.10^8$ |
| 2* | 180 | $1.8.10^8$ |
| 3* | 520 | $5.2.10^8$ |
| 4* | 160 | $1.6.10^8$ |

TABLE 4

| | Number of colonies LB/agar 2% sucrose | |
|---|---|---|
| | 30° C. | Mutation rate |
| 1* | 0 | 0 |
| 2* | 0 | 0 |
| 3* | 400 | $7.7\ 10^{-6}$ |
| 4* | >800 | $>5\ 10^{-5}$ |

TABLE 5

| | Number of colonies LB/agar 2% sucrose | |
|---|---|---|
| | 37° C. | Mutation rate |
| 1* | 0 | 0 |
| 2* | 0 | 0 |
| 3* | 400 | $7.7\ 10^{-6}$ |
| 4* | >800 | $>5\ 10^{-5}$ |

TABLE 6

| | Number of colonies LB/agar 4% sucrose 30° C. | Mutation rate |
|---|---|---|
| 1* | 0 | 0 |
| 2* | 0 | 0 |
| 3* | 200 | $3.8\ 10^{-6}$ |
| 4* | 800 | $5\ 10^{-5}$ |

TABLE 7

| | Number of colonies LB/agar 4% sucrose 37° C. | Mutation rate |
|---|---|---|
| 1* | 0 | 0 |
| 2* | 0 | 0 |
| 3* | 250 | $4.8\ 10^{-6}$ |
| 4* | ~800 | $5\ 10^{-5}$ |

1*: BJ5183 ΔpurNΩ λPr::sacB Km ΔedaΩ λPr::sacB Cat clone #1
2*: BJ5183 ΔpurNΩ λPr::sacB Km ΔedaΩ λPr::sacB Cat clone #2
3*: BJ5183 ΔpurNΩ λPr::sacB Km clone #16
4*: BJ5183 ΔedAΩ λPr::sacB Km Clone #11

Example 8

Plasmid Maintenance and Yields Obtained in the Absence of Antibiotic Selection Pressure (the cI Plasmid is Maintained at a High Copy Number in the Host Strain)

E. coli host cells expressing sacB and harboring the cI plasmid (pPB829 or pPB838) were grown in the absence of antibiotic selection pressure (e.g. in presence of sucrose) or in the presence of Cat as control.

In FIG. 11, the plasmid yield was determined at passages 2 and 5. Plasmids were extracted from cultures maintained at 30° C. and subjected to gel electrophoresis. The HindIII restriction digestion indicates that no obvious genetic rearrangement occurred in either pPB829 or pPB838 during propagation and selection with either Cat or Sucrose. Moreover, similar cI plasmids maintenance was observed during the selection of the cI plasmids under either Cat or Sucrose selection pressure.

Figure 15A:
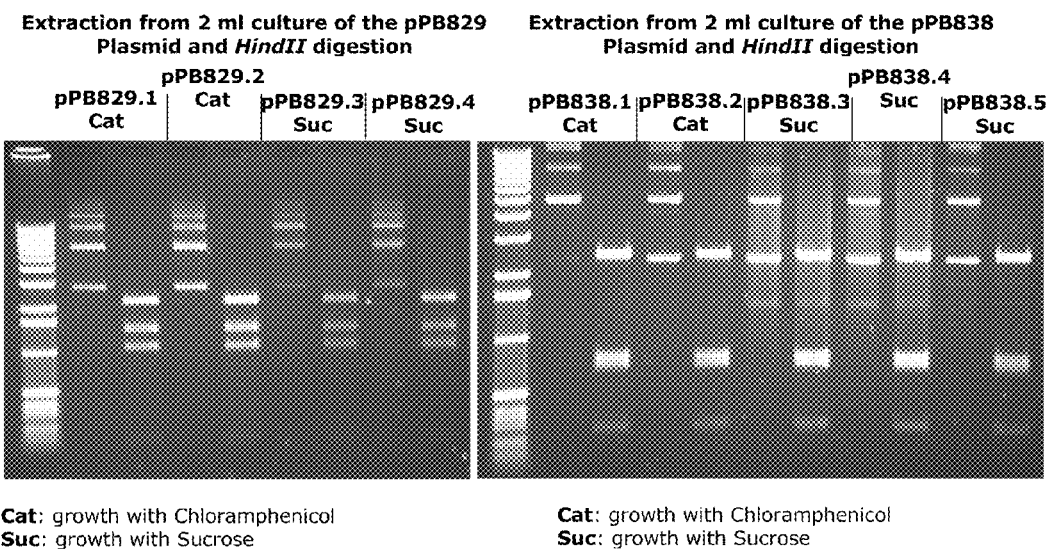
FIGS. 15A-B illustrate the stability and yield of the pPB829 and pPB838 plasmids in the growing E. coli cells which contain one copy of the sacB cassette.
Figure 15B:
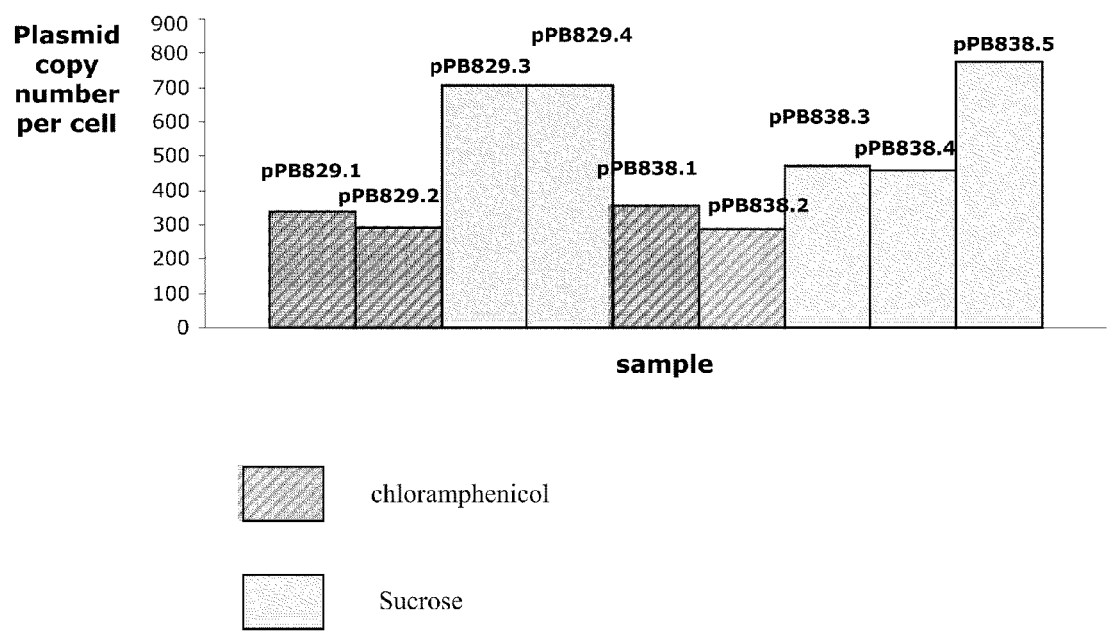

FIGS. 15A-B illustrate the stability and efficacy of the cI plasmids (pPB829 and pPB838, containing one copy of the sacB cassette) maintenance in cultures, including lack of genetic rearrangement after selection on either chlorampenicol or sucrose. Efficient plasmid maintenance and the stability of cI plasmids grown in the presence of either sucrose or chloramphenicol were observed. Moreover the plasmid yield (copy number) was much higher (approximately 700 per cell) when parental host strain transformed with either the pPB838 or pPB829 were grown at 30° C. in the presence of sucrose as selection pressure than cultivated in the presence of Cat as the selection pressure. The plasmid maintenance and yield were highly efficient and the copy number was twice higher compared to cells cultivated in the presence of Cat. This better cI plasmid yield when host cells were cultivated in the presence of sucrose was due to the weak promoter (P1) that controls the cI expression. Indeed, the expression of the cI repressor under the control of the weak promoter of Kanamycin gene (P1) had a positive effect on the plasmid yield to better counteract the toxicity of the sacB gene placed under the control of the λPr promoter.

As earlier demonstrated (see FIG. 11A), the antibiotic and non antibiotic systems are equivalent in terms of plasmid maintenance and selection of growing cells harboring the cI plasmid. FIG. 15B demonstrates that the plasmid yield (copy number) was much higher (approximately 700 per cell) when parental host strain transformed with either the pPB838 or pPB829 were grown in the presence of sucrose as selection pressure rather than cultivated in the presence of Cat as the selection pressure. The plasmid maintenance and yield were highly efficient and copy number was twice higher compared to cells cultivated in the presence of an antibiotic selection, such as Cat.

Example 9

Figure 15C:
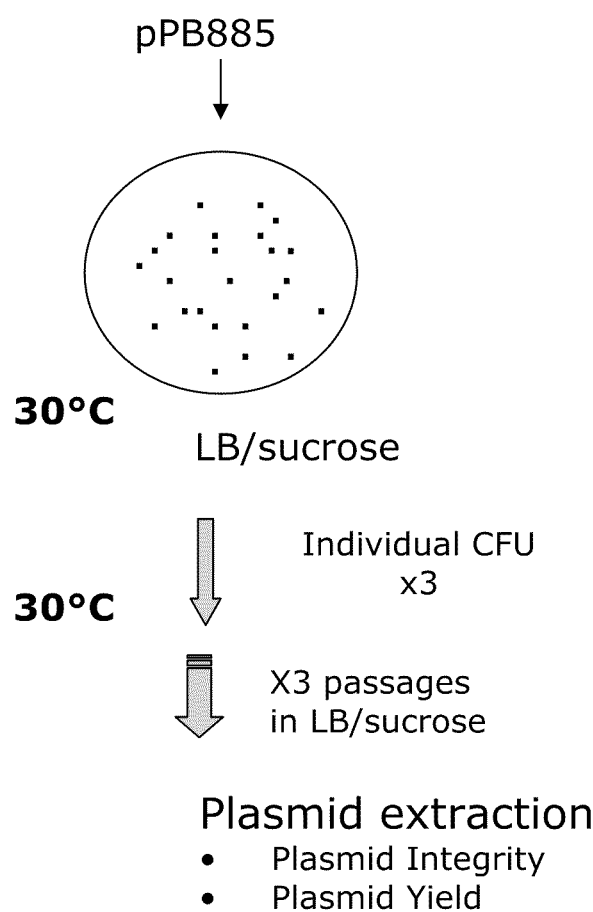
FIGS. 15C-E illustrate the stability and yield of cat-free pPB885 plasmid in both one and two sacB cassettes E. coli strain (ΔpurN λPr::sacB$^+$Ωkan and ΔpurN λPr::sacB$^+$Ωkan ΔedA λPr::sacB$^+$Ωcat, respectively).
Figure 15D:
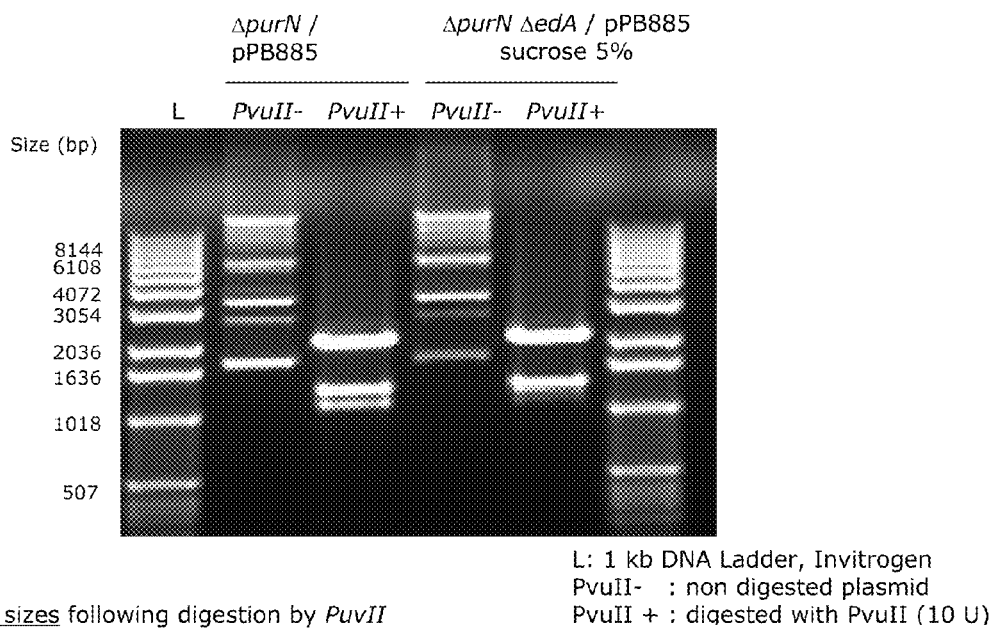
Figure 15E:
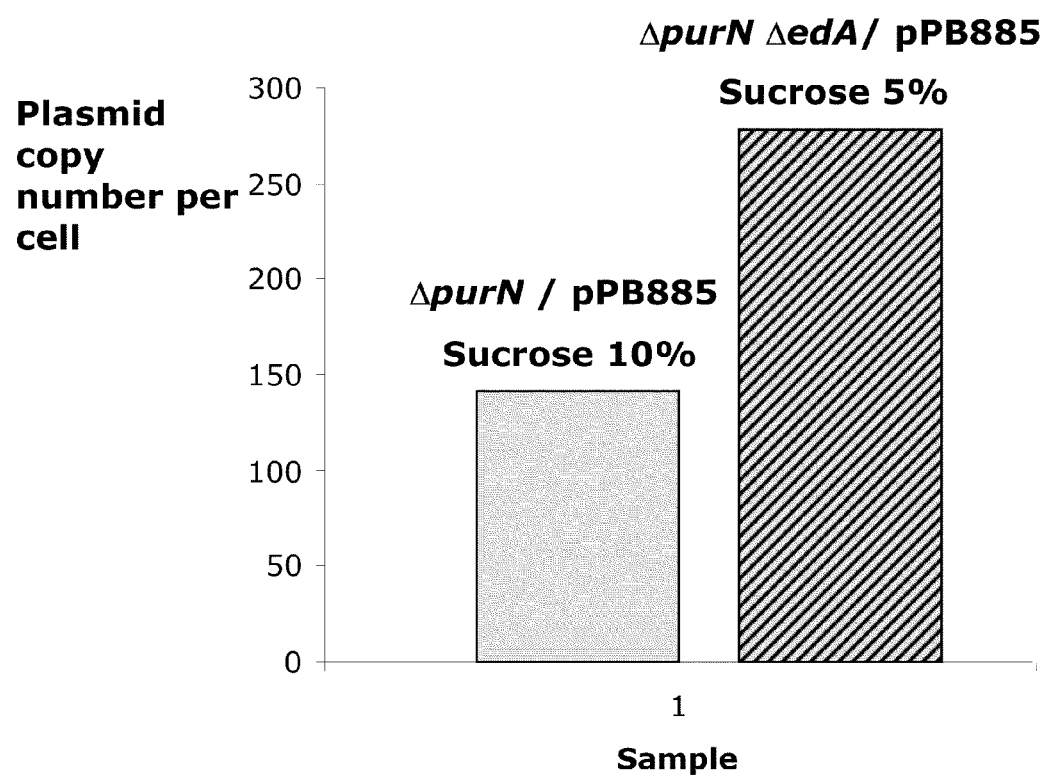

Plasmid Maintenance and Yields in the Absence of Antibiotic Gene in the a Plasmid: Comparative Analysis Between Both One and Two sacb Cassettes E. Coli Strains FIGS. 15C-E illustrate the stability and yield of cat-free pPB885 plasmid in both one and two sacB cassettes E. coli strains (ΔpurN λPr::sacB$^+$Ωkan and ΔpurN λPr::sacB$^+$Ωkan ΔedA λPr::sacB$^+$Ωcat, respectively). Both ΔpurNΩλPr::sacB km (one sacB cassette) and ΔpurNΩλPr::sacB km ΔedaΩλPr::sacB cat (two sacB cassettes) parental strains were transformed with the cI cat-free pPB885 plasmids and incubated for 3 hours in LB prior to plating on sucrose plate and subsequent cultivation (3 passages) in LB liquid growth medium supplemented with sucrose. The plasmid yield was determined at passages 3 in LB supplemented with 5% and 10% sucrose for the two and one sacB cassettes E. coli strains, respectively. The pPB885 plasmids were extracted from cultures maintained at 37° C. and subjected to gel electrophoresis. The PvuII restriction digestion indicates that no obvious genetic rearrangement occurred in either pPB885 during propagation and selection with Sucrose (see FIG. 15D). As demonstrated in this gel, no obvious genetic rearrangement occurred after selection with sucrose at either 10% and 5% in both E. coli host strains, one and two sacB cassette, respectively.

FIG. 15E illustrates the yield of the cat-free pPB885 plasmid in both one and two sacB cassettes E. coli strains (ΔpurN λPr::sacB$^+$Ωkan and ΔpurN ΔPr::sacB$^+$Ωkan ΔedA λPr::sacB$^+$Ωcat, respectively). Interestingly, the plasmid yield (copy number) was much higher (approximately 278 per cell) in the two sacB cassettes compared to the plasmid yield (approximately 142 per cell) obtained from the one sacB cassette E. coli strain. The plasmid yield obtained in this experiment appears lower than the plasmid yield obtained in the previous comparative study (see FIG. 15B). This is mainly due to the fact that i) more clones need to be evaluated following transformation with the pPB885 to identify the one being the best and ii) moreover, the growth condition of the two sacB cassettes E. coli strain transformed with the cat-free pPB885 plasmid was not optimally cultivated. Indeed, we had demonstrated that the optimal growth condition for this latest strain was at about 37° C. and about 2% sucrose (or slightly below). However, this result suggests that under optimal robustness condition, the plasmid yield could be better in a two sacB cassettes E. coli strain compared to the E. coli strain having one sacB cassette.

Example 10

Antibiotic-Free cI Plasmid Transfection in CHO Cells

FIG. 15F and Table 8 below illustrates the plasmid transfection efficacy (GFP expression) in CHO cells of the antibiotic-free plasmid (pPB896/Sucrose as selection pressure) and antibiotic plasmid (pCG105/Cat as selection pressure). No obvious difference is observed in terms of expressed GFP protein between these two selection pressures (Sucrose versus Cat as antibiotic). The pCG105 plasmid (pPB828-derived plasmid having the GFP gene placed under the control of the CMV promoter [Merial property]) and the pPB896 (pPB829 plasmid+P1::cI gene+GFP) plasmids were used in CHO cells' transfection to evaluate the functionality of the antibiotic-free plasmid concept versus current antibiotic plasmid. This experiment was performed using the plasmids isolated from culture of E. coli host strain having one sacB cassette. The pCG105 was propagated in E. coli using Kanamycin as selection pressure while the pPB896 was propagated in E. coli using 10% sucrose as selection pressure. DNA plasmids were extracted and dosed at the same concentration.

FIG. 15F illustrates the in vitro expression of the GFP protein encoded by pCG105 and pPB896 after transient transfection of CHO-K1 cells, using Lipofectamine 2000. CHO-K1 cells at 90% confluency in 6 cm diameter plates were transfected with 5 μg plasmid and 10 uL Lipofectamine each, according to manufacturer's instruction. After the transfection, cells were cultivated in MEM-glutamax medium containing 1% SVF for 24 hours. Culture were harvested and analyzed using fluorescence microscopy (FIG. 15G) and Flow Cytometry (FACS Calibur [Becton Dickinson]) (Table 8).

FIG. 15F shows that similar GFP epifluorescence was visualized in both transfected CHO-K1 cells. The pCG105 and pPB96 plasmids under the selection pressure of chloramphenicol and sucrose were able to transfect the CHO-K1 cells with comparable efficiency.

Table 8 shows the efficacy of CHO transfection with the pCG105 and pPB896 plasmids. As indicated in this table, a comparable % of CHO cells expressing the GFP protein was determined when CHO was transfected with pCG105 (59% GFP expressed) and pPB896 (48% GFP expressed). These results validated the use of the sucrose-based antibiotic-free plasmid system for application in CHO transfection and DNA vaccine purposes, ultimately.

TABLE 8

CHO transfection with GFP plasmids

|  | % dead cells | % cells with GFP expression | % viable cells with GFP expression |
| --- | --- | --- | --- |
| pVR1012 (control) | 45 | — | — |
| pCG105 | 33 | 59 | 89 |
| pPB896 | 49 | 48 | 93 |

These Examples demonstrate that the control of a toxic gene located on the chromosome can be achieved with a repressor located on a plasmid. The system is fully functional in the absence of antibiotic selection pressure. The system is stable over five (5) passages of the host cells. The system allows host cells to achieve a high plasmid copy number per cell. The system is fully compatible with the use of a minimum synthetic culture medium.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

---

What is claimed is:

1. A drugless plasmid comprising a polynucleotide encoding a cI repressor protein comprising the sequence of SEQ ID NO:2, wherein the expression of the cI repressor protein regulates the expression of a heterologous toxic gene product in a bacterial host.

2. The drugless plasmid of claim 1, wherein the polynucleotide is operably linked to a promoter.

3. The drugless plasmid of claim 2, wherein the promoter is a P1 promoter or a native cI promoter.

4. The drugless plasmid of claim 3, wherein the P1 promoter comprises the sequence of SEQ ID NO: 29 or SEQ ID NO:83.

5. The drugless plasmid of claim 3, wherein the native cI promoter comprises the sequence of SEQ ID NO:30.

6. The drugless plasmid of claim 1, wherein the polynucleotide comprises the sequence of SEQ ID NO:1.

7. The drugless plasmid of claim 6, wherein the polynucleotide is operably linked to a promoter.

8. The drugless plasmid of claim 7, wherein the promoter is a P1 promoter or a native cI promoter.

9. The drugless plasmid of claim 8, wherein the P1 promoter comprises the sequence of SEQ ID NO: 29 or SEQ ID NO:83.

10. The drugless plasmid of claim 8, wherein the native cI promoter comprises the sequence of SEQ ID NO:30.

11. The drugless plasmid of claim 1 further comprising a heterologous polynucleotide encoding an immunogen or a protein.

12. The drugless plasmid of claim 11, wherein the heterologous polynucleotide is operably linked to a promoter functional in eukaryotic or prokaryotic cells.

13. The drugless plasmid of claim 12, wherein the promoter is a CMV promoter or a promoter isolated from a gram-negative bacterium.

14. An engineered gram-negative bacterium host strain comprising the drugless plasmid of claim 1, wherein the bacterium further comprises one or more heterologous polynucleotides in a nonessential region of the bacterial chromosome, and wherein comprises one or more heterologous polynucleotides encodes a product that is toxic to the bacterium host.

15. The bacterium strain of claim 14, wherein the one or more heterologous polynucleotides encoding a product that is toxic to the bacterium host comprises a sacB gene.

16. The bacterium strain of claim 14, wherein the one or more heterologous polynucleotides encoding a product that is toxic to the bacterium host is operably linked to a promoter.

17. The bacterium strain of claim 16, wherein the promoter is a promoter from λ phage.

18. The bacterium strain of claim 14, wherein the nonessential region comprises a deA gene or a purN gene.

19. The engineered gram-negative bacterium of claim 14, wherein the gram-negative bacterium is selected from the group consisting of *Avibacterium, Brucella, Escherichia coli, Haemophilus, Salmonella, Shigella, Pasteurella*, and *Rimeirella*.

20. The engineered gram-negative bacterium of claim 14, wherein the polynucleotide encoding the cI repressor protein is operably linked to a P1 promoter comprising the sequence of SEQ ID NO:29 or SEQ ID NO:83.

21. The engineered gram-negative bacterium of claim 14, wherein the polynucleotide encoding the cI repressor protein is operably linked to a native cI promoter comprising the sequence of SEQ ID NO:30.

22. A composition comprising the drugless plasmid of claim 1.

23. The composition of claim 22 further comprising a pharmaceutically acceptable carrier.

* * * * *

SEQUENCE LISTING

```
<160> NUMBER OF SEQ ID NOS: 83

<210> SEQ ID NO 1
<211> LENGTH: 711
<212> TYPE: DNA
<213> ORGANISM: artificial sequence
<220> FEATURE:
<223> OTHER INFORMATION: cI857 repressor gene

<400> SEQUENCE: 1
atgagcacaa aaagaaacc attaacacaa gagcagcttg aggacgcacg tcgccttaaa      60
gcaatttatg aaaaaagaa aaatgaactt ggcttatccc aggaatctgt cgcagacaag     120
atggggatgg ggcagtcagg cgttggtgct ttatttaatg gcatcaatgc attaaatgct     180
tataacgccg cattgcttac aaaaattctc aaagttagcg ttgaagaatt tagcccttca     240
atcgccagag aaatctacga gatgtatgaa gcggttagta tgcagccgtc acttagaagt     300
gagtatgagt accctgtttt ttctcatgtt caggcaggga tgttctcacc taagcttaga     360
accttaccca aaggtgatgc ggagagatgg gtaagcacaa ccaaaaaagc cagtgattct     420
gcattctggc ttgaggttga aggtaattcc atgaccgcac caacaggctc caagccaagc     480
tttcctgacg gaatgttaat tctcgttgac cctgagcagg ctgttgagcc aggtgatttc     540
```
tgcatagcca gacttggggg tgatgagttt accttcaaga aactgatcag ggatagcggt    600
caggtgtttt tacaaccact aaacccacag tacccaatga tcccatgcaa tgagagttgt    660
tccgttgtgg ggaaagttat cgctagtcag tggcctgaag agacgtttgg c             711

<210> SEQ ID NO 2
<211> LENGTH: 237
<212> TYPE: PRT
<213> ORGANISM: artificial sequence
<220> FEATURE:
<223> OTHER INFORMATION: cI repressor protein

<400> SEQUENCE: 2

Met Ser Thr Lys Lys Pro Leu Thr Gln Glu Gln Leu Glu Asp Ala
1               5                   10                  15

Arg Arg Leu Lys Ala Ile Tyr Glu Lys Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Thr Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Lys Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235

<210> SEQ ID NO 3
<211> LENGTH: 1422
<212> TYPE: DNA
<213> ORGANISM: artificial sequence
<220> FEATURE:
<223> OTHER INFORMATION: sacB gene

<400> SEQUENCE: 3
atgaacatca aaaagtttgc aaaacaagca acagtattaa cctttactac cgcactgctg    60
gcaggaggcg caactcaagc gtttgcgaaa gaaacgaacc aaaagccata taaggaaaca    120
tacggcattt cccatattac acgccatgat atgctgcaaa tccctgaaca gcaaaaaaat    180
gaaaaatatc aagttcctga attcgattcg tccacaatta aaaatatctc ttctgcaaaa    240

```
ggcctggacg tttgggacag ctggccatta caaaacgctg acggcactgt cgcaaactat    300
cacggctacc acatcgtctt tgcattagcc ggagatccta aaaatgcgga tgacacatcg    360
atttacatgt tctatcaaaa agtcggcgaa acttctattg acagctggaa aaacgctggc    420
cgcgtcttta aagacagcga caaattcgat gcaaatgatt ctatcctaaa agaccaaaca    480
caagaatggt caggttcagc cacatttaca tctgacggaa aaatccgttt attctacact    540
gatttctccg gtaaacatta cggcaaacaa acactgacaa ctgcacaagt taacgtatca    600
gcatcagaca gctcttga catcaacggt gtagaggatt ataaatcaat ctttgacggt    660
```

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470

<210> SEQ ID NO 5
<211> LENGTH: 30
<212> TYPE: DNA
<213> ORGANISM: artificial sequence
<220> FEATURE:
<223> OTHER INFORMATION: lambda right promoter driving sacB gene

<400> SEQUENCE: 5
ttgactattt tacctctggc ggtgataatg                                  30

<210> SEQ ID NO 6
<211> LENGTH: 50
<212> TYPE: DNA
<213> ORGANISM: artificial sequence
<220> FEATURE:

<223> OTHER INFORMATION: LB1232 primer

<400> SEQUENCE: 6
ccgaacaacg cgtggttatc gacaccgcaa gggataaata tctaacaccg         50

<210> SEQ ID NO 7
<211> LENGTH: 50
<212> TYPE: DNA
<213> ORGANISM: artificial sequence
<220> FEATURE:
<223> OTHER INFORMATION: PB1233 primer

<400> SEQUENCE: 7 caaactttttt gatgttcata tccatctgat cctcttcaaa aggccacctg         50

<210> SEQ ID NO 8
<211> LENGTH: 55
<212> TYPE: DNA
<213> ORGANISM: artificial sequence
<220> FEATURE:
<223> OTHER INFORMATION: PB1234 primer

<400> SEQUENCE: 8
gacgacaaat tgtaatcag gcgagagcac cgcaagggat aaatatctaa caccg     55

<210> SEQ ID NO 9
<211> LENGTH: 26
<212> TYPE: DNA
<213> ORGANISM: artificial sequence
<220> FEATURE:
<223> OTHER INFORMATION: PB1192 primer

<400> SEQUENCE: 9
atggatatga acatcaaaaa gtttgc                                    26

<210> SEQ ID NO 10
<211> LENGTH: 52
<212> TYPE: DNA
<213> ORGANISM: artificial sequence
<220> FEATURE:
<223> OTHER INFORMATION: PB1193 primer

<400> SEQUENCE: 10
aaacaaatag gggttccgcg cacatttatt tgttaactgt taattgtcct tg       52

<210> SEQ ID NO 11
<211> LENGTH: 22
<212> TYPE: DNA
<213> ORGANISM: artificial sequence
<220> FEATURE:
<223> OTHER INFORMATION: PB1194 primer

<400> SEQUENCE: 11
atgtgcgcgg aaccctatt tg                                         22

<210> SEQ ID NO 12
<211> LENGTH: 54
<212> TYPE: DNA
<213> ORGANISM: artificial sequence
<220> FEATURE:
<223> OTHER INFORMATION: PB1195 primer

<400> SEQUENCE: 12
gacgtttccc gttgaatatg gctcatactc ttccttttc aatattattg aagc      54

```
<210> SEQ ID NO 13
<211> LENGTH: 24
<212> TYPE: DNA
<213> ORGANISM: artificial sequence
<220> FEATURE:
<223> OTHER INFORMATION: PB1196 primer

<400> SEQUENCE: 13
atgagccata ttcaacggga aacg                                         24

<210> SEQ ID NO 14
<211> LENGTH: 54
<212> TYPE: DNA
<213> ORGANISM: artificial sequence
<220> FEATURE:
<223> OTHER INFORMATION: PB1197 primer

<400> SEQUENCE: 14
gaaaaacgcc agcggcagag ctggcgctta gaaaaactca tcgagcatca aatg        54

<210> SEQ ID NO 15
<211> LENGTH: 41
<212> TYPE: DNA
<213> ORGANISM: artificial sequence
<220> FEATURE:
<223> OTHER INFORMATION: PB1237 sequence

<400> SEQUENCE: 15
tttgcggccg ctggtggtgg tcgccatgtg cgttaatgac c                      41

<210> SEQ ID NO 16
<211> LENGTH: 25
<212> TYPE: DNA
<213> ORGANISM: artificial sequence
<220> FEATURE:
<223> OTHER INFORMATION: PB1199 primer

<400> SEQUENCE: 16
tattcgataa ccacgcgttg ttcgg                                        25

<210> SEQ ID NO 17
<211> LENGTH: 27
<212> TYPE: DNA
<213> ORGANISM: artificial sequence
<220> FEATURE:
<223> OTHER INFORMATION: PB1200 primer

<400> SEQUENCE: 17
gcgccagctc tgccgctggc gttttc                                       27

<210> SEQ ID NO 18
<211> LENGTH: 44
<212> TYPE: DNA
<213> ORGANISM: artificial sequence
<220> FEATURE:
<223> OTHER INFORMATION: PB1238 primer

<400> SEQUENCE: 18
tttggatccg ctggtggata tcatcaaggc agtaacgcag aatg                   44

<210> SEQ ID NO 19
<211> LENGTH: 42
<212> TYPE: DNA
<213> ORGANISM: artificial sequence
<220> FEATURE:
<223> OTHER INFORMATION: PB1235 primer
```

<400> SEQUENCE: 19
tttgcggccg ctggtggttg agaaccaggt gattgaagcg cc        42

<210> SEQ ID NO 20
<211> LENGTH: 27
<212> TYPE: DNA
<213> ORGANISM: artificial sequence
<220> FEATURE:
<223> OTHER INFORMATION: PB1209 primer

<400> SEQUENCE: 20
ctctcgcctg attacaaatt tgtcgtc        27

<210> SEQ ID NO 21
<211> LENGTH: 23
<212> TYPE: DNA
<213> ORGANISM: artificial sequence
<220> FEATURE:
<223> OTHER INFORMATION: PB1210 primer

<400> SEQUENCE: 21
aggatcgggc atttttgtag cgt        23

<210> SEQ ID NO 22
<211> LENGTH: 40
<212> TYPE: DNA
<213> ORGANISM: artificial sequence
<220> FEATURE:
<223> OTHER INFORMATION: PB1236 primer

<400> SEQUENCE: 22
tttctagagc tggtggcgac taccgtgaat cctggcaacc        40

<210> SEQ ID NO 23
<211> LENGTH: 23
<212> TYPE: DNA
<213> ORGANISM: artificial sequence
<220> FEATURE:
<223> OTHER INFORMATION: PB1204 primer

<400> SEQUENCE: 23
gtggtgctta tttccggcaa cgg        23

<210> SEQ ID NO 24
<211> LENGTH: 23
<212> TYPE: DNA
<213> ORGANISM: artificial sequence
<220> FEATURE:
<223> OTHER INFORMATION: PB1205 primer

<400> SEQUENCE: 24
ccagccacgc ggcgttttcg tgc        23

<210> SEQ ID NO 25
<211> LENGTH: 23
<212> TYPE: DNA
<213> ORGANISM: artificial sequence
<220> FEATURE:
<223> OTHER INFORMATION: PB1214 primer

<400> SEQUENCE: 25
gaccaccggc ccggttgtac cgg        23

<210> SEQ ID NO 26
<211> LENGTH: 22

```
<212> TYPE: DNA
<213> ORGANISM: artificial sequence
<220> FEATURE:
<223> OTHER INFORMATION: PB1215 primer

<400> SEQUENCE: 26
cggacccgcg atcgcctgca gg                                            22

<210> SEQ ID NO 27
<211> LENGTH: 24
<212> TYPE: DNA
<213> ORGANISM: artificial sequence
<220> FEATURE:
<223> OTHER INFORMATION: PB1213 primer

<400> SEQUENCE: 27
ggtggatggc gtccatttct gtgc                                          24

<210> SEQ ID NO 28
<211> LENGTH: 23
<212> TYPE: DNA
<213> ORGANISM: artificial sequence
<220> FEATURE:
<223> OTHER INFORMATION: PB1212 primer

<400> SEQUENCE: 28
caaaagtgtt aagcggtaac ctg                                           23

<210> SEQ ID NO 29
<211> LENGTH: 35
<212> TYPE: DNA
<213> ORGANISM: artificial sequence
<220> FEATURE:
<223> OTHER INFORMATION: weak promoter of Kan gene (P1 promoter)

<400> SEQUENCE: 29
gtgatacgcc tatttttata ggttaatgtc atgat                              35

<210> SEQ ID NO 30
<211> LENGTH: 40
<212> TYPE: DNA
<213> ORGANISM: artificial sequence
<220> FEATURE:
<223> OTHER INFORMATION: native cI gene promoter

<400> SEQUENCE: 30
ggtgttagat atttatccct tgcggtgata gatttaacgt                         40

<210> SEQ ID NO 31
<211> LENGTH: 660
<212> TYPE: DNA
<213> ORGANISM: artificial sequence
<220> FEATURE:
<223> OTHER INFORMATION: Cat Gene

<400> SEQUENCE: 31
atggagaaaa aaatcactgg atataccacc gttgatatat cccaatggca tcgtaaagaa   60
cattttgagg catttcagtc agttgctcaa tgtacctata accagaccgt tcagctggat  120
attacggcct ttttaaagac cgtaaagaaa aataagcaca gtttatcc ggcctttatt   180 cacattcttg cccgcctgat gaatgctcat ccggaatttc gtatggcaat gaaagacggt  240
gagctggtga tatgggatag tgttcaccct tgttacaccg ttttccatga gcaaactgaa  300
acgttttcat cgctctggag tgaataccac gacgatttcc ggcagtttct acacatatat  360
```

```
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttcatcatg ccgtttgtga tggcttccat    600
gtcggcagaa tgcttaatga attacaacag tactgcgatg agtggcaggg cggggcgtaa    660
```

<210> SEQ ID NO 32
<211> LENGTH: 219
<212> TYPE: PRT
<213> ORGANISM: artificial sequence
<220> FEATURE:
<223> OTHER INFORMATION: Cat protein

<400> SEQUENCE: 32

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 33
<211> LENGTH: 37
<212> TYPE: DNA
<213> ORGANISM: artificial sequence
<220> FEATURE:
<223> OTHER INFORMATION: PB1184 primer

<400> SEQUENCE: 33
gaattccggt ccgggcgaaa atgagacgtt gatcggc                              37

<210> SEQ ID NO 34
<211> LENGTH: 66
<212> TYPE: DNA
<213> ORGANISM: artificial sequence

```
<220> FEATURE:
<223> OTHER INFORMATION: PB1185 primer

<400> SEQUENCE: 34
cctaggctgt gttaattaag gcgcgccgaa ttccggtccg ttacgccccg ccctgccact      60
catcgc                                                                 66

<210> SEQ ID NO 35
<211> LENGTH: 43
<212> TYPE: DNA
<213> ORGANISM: artificial sequence
<220> FEATURE:
<223> OTHER INFORMATION: PB1186 primer

<400> SEQUENCE: 35
tcataccagg cctaggtgat acgcctattt ttataggtta atg                        43

<210> SEQ ID NO 36
<211> LENGTH: 25
<212> TYPE: DNA
<213> ORGANISM: artificial sequence
<220> FEATURE:
<223> OTHER INFORMATION: PB1187 primer

<400> SEQUENCE: 36 aacaccccctt gtattactgt ttatg                                           25

<210> SEQ ID NO 37
<211> LENGTH: 43
<212> TYPE: DNA
<213> ORGANISM: artificial sequence
<220> FEATURE:
<223> OTHER INFORMATION: PB1188 primer

<400> SEQUENCE: 37
aatacaaggg gtgttatgag cacaaaaaag aaaccattaa cac                        43

<210> SEQ ID NO 38
<211> LENGTH: 42
<212> TYPE: DNA
<213> ORGANISM: artificial sequence
<220> FEATURE:
<223> OTHER INFORMATION: PB1189 primer

<400> SEQUENCE: 38
ccggaattcg gcgcgtcagc caaacgtctc ttcaggccac tg                         42

<210> SEQ ID NO 39
<211> LENGTH: 36
<212> TYPE: DNA
<213> ORGANISM: artificial sequence
<220> FEATURE:
<223> OTHER INFORMATION: PB1182 primer

<400> SEQUENCE: 39
agatctgtta acggcgaaaa tgagacgttg atcggc                                36

<210> SEQ ID NO 40
<211> LENGTH: 38
<212> TYPE: DNA
<213> ORGANISM: artificial sequence
<220> FEATURE:
<223> OTHER INFORMATION: PB1183 primer

<400> SEQUENCE: 40
```

```
gtcgacgtta acttacgccc cgccctgcca ctcatcgc                                38
```

<210> SEQ ID NO 41
<211> LENGTH: 25
<212> TYPE: DNA
<213> ORGANISM: artificial sequence
<220> FEATURE:
<223> OTHER INFORMATION: PB1263 primer

<400> SEQUENCE: 41

```
tcagccaaac gtctcttcag gccac                                              25
```

<210> SEQ ID NO 42
<211> LENGTH: 42
<212> TYPE: DNA
<213> ORGANISM: artificial sequence
<220> FEATURE:
<223> OTHER INFORMATION: PB1266 primer

<400> SEQUENCE: 42

```
gctgactcat accaggcacg cacggtgtta gatatttatc cc                           42
```

<210> SEQ ID NO 43
<211> LENGTH: 683
<212> TYPE: DNA
<213> ORGANISM: artificial sequence
<220> FEATURE:
<223> OTHER INFORMATION: CMV promoter

<400> SEQUENCE: 43

```
ttggctattg gccattgcat acgttgtatc catatcataa tatgtacatt tatattggct        60
catgtccaac attaccgcca tgttgacatt gattattgac tagttattaa tagtaatcaa       120
ttacggggtc attagttcat agcccatata tggagttccg cgttacataa cttacggtaa       180
atggcccgcc tggctgaccg cccaacgacc cccgcccatt gacgtcaata atgacgtatg       240
ttcccatagt aacgccaata gggactttcc attgacgtca atgggtggag tatttacggt       300
aaactgccca cttggcagta catcaagtgt atcatatgcc aagtacgccc cctattgacg       360
tcaatgacgg taaatggccc gcctggcatt atgcccagta catgacctta tgggactttc       420
ctacttggca gtacatctac gtattagtca tcgctattac catggtgatg cggttttggc       480
agtacatcaa tgggcgtgga tagcggtttg actcacgggg atttccaagt ctccacccca       540
ttgacgtcaa tgggagtttg ttttggcacc aaaatcaacg ggactttcca aaatgtcgta       600
acaactccgc cccattgacg caaatgggcg gtaggcgtgt acggtgggag gtctatataa       660
gcagagctcg tttagtgaac cgt                                               683
```

<210> SEQ ID NO 44
<211> LENGTH: 237
<212> TYPE: PRT
<213> ORGANISM: artificial sequence
<220> FEATURE:
<223> OTHER INFORMATION: ABO40666 cI repressor protein

<400> SEQUENCE: 44

```
Met Ser Thr Lys Lys Leu Leu Thr Gln Glu Gln Leu Glu Asp Ala
1               5                   10                  15

Arg Arg Leu Lys Ala Ile Tyr Glu Lys Lys Lys Asn Glu Leu Gly Leu
                20                  25                  30

Ser Gln Glu Ser Val Ala Asp Lys Met Gly Met Gly Gln Ser Gly Val
            35                  40                  45
```

Gly Ala Leu Phe Asn Gly Ile Asn Ala Leu Asn Ala Tyr Asn Ala Ala
             50                  55                  60

Leu Leu Ala Lys Ile Leu Lys Val Ser Val Glu Glu Phe Ser Pro Ser
 65                  70                  75                  80

Ile Ala Arg Glu Ile Tyr Glu Met Tyr Glu Ala Val Ser Met Gln Pro
                     85                  90                  95

Ser Leu Arg Ser Glu Tyr Glu Tyr Pro Val Phe Ser His Val Gln Ala
                100                 105                 110

Gly Met Phe Ser Pro Glu Leu Arg Thr Phe Thr Lys Gly Asp Ala Glu
            115                 120                 125

Arg Trp Val Ser Thr Thr Lys Lys Ala Ser Asp Ser Ala Phe Trp Leu
130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
            195                 200                 205

Pro Gln Tyr Pro Met Ile Pro Cys Asn Glu Ser Cys Ser Val Val Gly
210                 215                 220

Lys Val Ile Ala Ser Gln Trp Pro Glu Glu Thr Phe Gly
225                 230                 235

<210> SEQ ID NO 45
<211> LENGTH: 714
<212> TYPE: DNA
<213> ORGANISM: artificial sequence
<220> FEATURE:
<223> OTHER INFORMATION: EF120455 cI encoding gene

<400> SEQUENCE: 45
atgagcacaa aaagaaaact attaacacaa gagcagcttg aggacgcacg tcgccttaaa      60
gcaatttatg aaaaaaagaa aaatgaactt ggcttatccc aggaatctgt cgcagacaag     120
atggggatgg ggcagtcagg cgttggtgct ttatttaatg gcatcaatgc attaaatgct     180
tataacgccg cattgcttgc aaaaattctc aaagttagcg ttgaagaatt tagcccttca     240
atcgccagag aaatctacga gatgtatgaa gcggttagta tgcagccgtc acttagaagt     300
gagtatgagt accctgtttt ttctcatgtt caggcaggga tgttctcacc tgagcttaga     360
acctttacca aggtgatgc ggagagatgg gtaagcacaa ccaaaaaagc cagtgattct     420
gcattctggc ttgaggttga aggtaattcc atgaccgcac caacaggctc aagccaagc     480 tttcctgacg gaatgttaat tctcgttgac cctgagcagg ctgttgagcc aggtgatttt     540
tgcatagcca gacttggagg tgatgagttt accttcaaga aactgatcag ggatagcggt     600
caggtgtttt tacaaccact aaacccgcaa tatccaatga tcccatgcaa tgagagttgt     660
tccgttgtgg ggaaagttat cgccagccag tggccagaag agacgtttgg ctga          714

<210> SEQ ID NO 46
<211> LENGTH: 237
<212> TYPE: PRT
<213> ORGANISM: artificial sequence
<220> FEATURE:
<223> OTHER INFORMATION: ABO40673 cI repressor protein

<400> SEQUENCE: 46

```
Met Ser Ala Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
            20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
50                  55                  60

Leu Leu Ala Lys Ile Leu Asn Val Ser Val Glu Phe Ser Pro Ser
65              70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Ser Asp Ala Glu
            115                 120                 125

Lys Trp Val Ser Thr Thr Lys Lys Ala Ser Gly Ser Ala Phe Trp Leu
        130                 135                 140

Glu Val Glu Gly Asn Ser Met Thr Ala Pro Thr Gly Tyr Lys Pro Ser
145                 150                 155                 160

Phe Pro Asp Gly Met Leu Ile Leu Val Asp Pro Glu Gln Thr Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235
```

<210> SEQ ID NO 47
<211> LENGTH: 714
<212> TYPE: DNA
<213> ORGANISM: artificial sequence
<220> FEATURE:
<223> OTHER INFORMATION: EF120456 cI encoding gene

<400> SEQUENCE: 47

| | | | | |
|---|---|---|---|---|
| atgagcgcaa | aaagaaaacc | gttaacacaa | gagcagcttg | aggacgcacg | tcgccttaaa | 60 |
| gctatttatg | aaaaaaagaa | aaatgaactt | ggcttatctc | aggaatctgt | cgcagacaag | 120 |
| atggggatgg | ggcagtcagg | cgttggtgct | ttatttaatg | gtatcaatgc | attaaatgct | 180 |
| tataacgccg | cattgcttgc | aaaaattctc | aacgttagcg | ttgaagaatt | tagcccttca | 240 |
| atcgccagag | aaatctacga | gatgtatgaa | gcggttagta | tgcagccgtc | acttagaagt | 300 |
| gagtatgagt | accctgtttt | ttctcatgtt | caggccggga | tgttctcgcc | tgagcttaga | 360 |
| acctttacca | aagtgatgc | ggagaaatgg | gtaagcacaa | ctaaaaaagc | cagtggctct | 420 |
| gcattctggc | ttgaggttga | aggtaattcc | atgaccgcac | caacaggcta | caagccaagc | 480 |
| tttcctgacg | ggatgttaat | tcttgttgac | cctgagcaga | ctgttgagcc | tggtgatttc | 540 |
| tgcatagcca | gacttggtgg | tgacgagttt | accttcaaga | aactgatcag | ggatagcggt | 600 |
| caggtgttcc | tacaaccact | aaacccgcaa | tatccaatga | tcccatgcaa | tgagagttgc | 660 |
| tccgttgtgg | ggaaagttat | cgctagtcag | tggcctgaag | agacgtttgg | ttaa | 714 |

<210> SEQ ID NO 48
<211> LENGTH: 237
<212> TYPE: PRT
<213> ORGANISM: artificial sequence
<220> FEATURE:
<223> OTHER INFORMATION: ABO40681 cI repressor protein

<400> SEQUENCE: 48

```
Met Ser Ala Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235
```

<210> SEQ ID NO 49
<211> LENGTH: 714
<212> TYPE: DNA
<213> ORGANISM: artificial sequence
<220> FEATURE:
<223> OTHER INFORMATION: EF120457 cI encoding gene

<400> SEQUENCE: 49

```
atgagcgcaa aaagaaaacc attaacacaa gagcagcttg aggacgcacg tcgccttaaa      60
gcaatttatg aaaaaaagaa aaatgaactt ggcttatccc aggaatctgt cgcagacaag     120
atggggatgg ggcagtcagg cgttggtgct ttatttaatg gcatcaatgc attaaatgct     180
tataacgccg cattgcttgc aaaaattctc aaagttagcg ttgaagaatt tagcccttca     240
atcgccagag aaatctacga gatgtatgaa gcggttagta tgcagccgtc acttagaagt     300
gagtatgagt accctgtttt ttctcatgtt caggcaggga tgttctcacc tgagcttaga     360
acctttacca aggtgatgc ggagagatgg gtaagcacaa ccaaaaaagc cagtgattct     420
```

```
gcattctggc ttgaggttga aggtaattcc atgaccgcac caacaggctc caagccaagc      480
tttcctgacg gaatgttaat tctcgttgac cctgagcagg ctgttgagcc aggtgatttc      540
tgcatagcca gacttggggg tgatgaattt accttcaaga aactgatcag ggatagcggt      600
caggtgtttc tacagccact aaacccacaa tacccaatga tcccatgcaa tgagagttgt      660
tccgttgtgg ggaaagttat cgctagtcag tggcctgaag agacgtttgg gtga            714
```

<210> SEQ ID NO 50
<211> LENGTH: 237
<212> TYPE: PRT
<213> ORGANISM: artificial sequence
<220> FEATURE:
<223> OTHER INFORMATION: ABO40689 cI repressor protein

<400> SEQUENCE: 50

```
Met Ser Ala Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
                20                  25                  30

Pro Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235
```

<210> SEQ ID NO 51
<211> LENGTH: 714
<212> TYPE: DNA
<213> ORGANISM: artificial sequence
<220> FEATURE:
<223> OTHER INFORMATION: EF120458 cI encoding gene

<400> SEQUENCE: 51

```
atgagcgcaa aaagaaaacc attaacacaa gagcagcttg aggacgcacg tcgccttaaa      60
gcaatttatg aaaaaaagaa aaatgaactt ggcttacccc aggaatctgt cgcagacaag     120
```

```
atggggatgg ggcagtcagg cgttggtgct ttatttaatg gcatcaatgc attaaatgct    180
tataacgccg cattgcttgc aaaaattctc aaagttagcg ttgaagaatt tagcccttca    240
atcgccagag aaatctacga gatgtatgaa gcggttagta tgcagccgtc acttagaagt    300
gagtatgagt accctgtttt ttctcatgtt caggcaggga tgttctcacc tgagcttaga    360
acctttacca aaggtgatgc ggagagatgg gtaagcacaa ccaaaaaagc cagtgattct    420
gcattctggc ttgaggttga aggtaattcc atgaccgcac caacaggctc caagccaagc    480
tttcctgacg gaatgttaat tctcgttgac cctgagcagg ctgttgagcc aggtgatttc    540
tgcatagcca gacttggggg tgatgaattt accttcaaga aactgatcag ggatagcggt    600
caggtgtttc tacagccact aaacccacaa tacccaatga tcccatgcaa tgagagttgt    660
tccgttgtgg ggaaagttat cgctagtcag tggcctgaag agacgtttgg gtga          714
```

<210> SEQ ID NO 52
<211> LENGTH: 237
<212> TYPE: PRT
<213> ORGANISM: artificial sequence
<220> FEATURE:
<223> OTHER INFORMATION: BAE79430 cI repressor protein

<400> SEQUENCE: 52

```
Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
                20                  25                  30

Ser Gln Glu Ser Val Ala Asp Lys Met Gly Met Gly Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Lys Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235
```

<210> SEQ ID NO 53
<211> LENGTH: 714

```
<212> TYPE: DNA
<213> ORGANISM: artificial sequence
<220> FEATURE:
<223> OTHER INFORMATION: AB248918 cI encoding gene

<400> SEQUENCE: 53
atgagcacaa aaagaaaacc attaacacaa gagcagcttg aggacgcacg tcgccttaaa      60
gcaatttatg aaaaaaagaa aaatgaactt ggcttatccc aggaatctgt cgcagacaag     120
atggggatgg ggcagtcagg cgttggtgct ttatttaatg gcatcaatgc attaaatgct     180
tataacgccg cattgcttgc aaaaattctc aaagttagcg ttgaagaatt tagcccttca     240
atcgccagag aaatctacga gatgtatgaa gcggttagta tgcagccgtc acttagaagt     300
gagtatgagt accctgtttt ttctcatgtt caggcaggga tgttctcacc taagcttaga     360
acctttacca aaggtgatgc ggagagatgg gtaagcacaa ccaaaaaagc cagtgattct     420
gcattctggc ttgaggttga aggtaattcc atgaccgcac caacaggctc aagccaagc     480 tttcctgacg gaatgttaat tctcgttgac cctgagcagg ctgttgagcc aggtgatttc     540
tgcatagcca gacttggggg tgatgagttt accttcaaga aactgatcag ggatagcggt     600
caggtgtttt tacaaccact aaacccacag tacccaatga tcccatgcaa tgagagttgt     660
tccgttgtgg ggaaagttat cgctagtcag tggcctgaag agacgtttgg ctga           714

<210> SEQ ID NO 54
<211> LENGTH: 237
<212> TYPE: PRT
<213> ORGANISM: artificial sequence
<220> FEATURE:
<223> OTHER INFORMATION: NP_040628 cI repressor protein

<400> SEQUENCE: 54

Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
                20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205
```

Pro Gln Tyr Pro Met Ile Pro Cys Asn Glu Ser Cys Ser Val Val Gly
        210                 215                 220

Lys Val Ile Ala Ser Gln Trp Pro Glu Glu Thr Phe Gly
225                 230                 235

<210> SEQ ID NO 55
<211> LENGTH: 714
<212> TYPE: DNA
<213> ORGANISM: artificial sequence
<220> FEATURE:
<223> OTHER INFORMATION: NC_001416 cI gene

<400> SEQUENCE: 55
atgagcacaa aaagaaacc attaacacaa gagcagcttg aggacgcacg tcgccttaaa      60
gcaatttatg aaaaaagaa aaatgaactt ggcttatccc aggaatctgt cgcagacaag     120
atggggatgg ggcagtcagg cgttggtgct ttatttaatg gcatcaatgc attaaatgct   180
tataacgccg cattgcttgc aaaaattctc aaagttagcg ttgaagaatt tagcccttca   240
atcgccagag aaatctacga tgtatgaa gcggttagta tgcagccgtc acttagaagt     300
gagtatgagt accctgtttt ttctcatgtt caggcaggga tgttctcacc tgagcttaga   360
acctttacca aggtgatgc ggagagatgg gtaagcacaa ccaaaaaagc cagtgattct    420
gcattctggc ttgaggttga aggtaattcc atgaccgcac caacaggctc aagccaagc    480 tttcctgacg aatgttaat tctcgttgac cctgagcagg ctgttgagcc aggtgatttc   540
tgcatagcca gacttggggg tgatgagttt accttcaaga aactgatcag ggatagcggt   600
caggtgtttt tacaaccact aaacccacag tacccaatga tcccatgcaa tgagagttgt   660
tccgttgtgg ggaaagttat cgctagtcag tggcctgaag agacgtttgg ctga          714

<210> SEQ ID NO 56
<211> LENGTH: 237
<212> TYPE: PRT
<213> ORGANISM: artificial sequence
<220> FEATURE:
<223> OTHER INFORMATION: NP_285953 cI repressor protein

<400> SEQUENCE: 56

Met Ser Ala Lys Lys Pro Leu Thr Gln Glu Gln Leu Glu Asp Ala
1               5                  10                  15

Arg Arg Leu Lys Ala Ile Tyr Glu Lys Lys Asn Glu Leu Gly Leu
                20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Asn Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Lys Trp Val Ser Thr Thr Lys Lys Ala Ser Gly Ser Ala Phe Trp Leu
    130                 135                 140

Glu Val Glu Gly Asn Ser Met Thr Ala Pro Thr Gly Ser Lys Pro Ser

```
                145                 150                 155                 160
Phe Pro Asp Gly Met Leu Ile Leu Val Asp Pro Glu Gln Ala Val Glu
                    165                 170                 175
Pro Gly Asp Phe Cys Ile Ala Arg Leu Gly Gly Asp Glu Phe Thr Phe
                180                 185                 190
Lys Lys Leu Ile Arg Asp Ser Gly Gln Val Phe Leu Gln Pro Leu Asn
                195                 200                 205
Pro Gln Tyr Pro Met Ile Pro Cys Asn Glu Ser Cys Ser Val Val Gly
            210                 215                 220
Lys Val Ile Ala Ser Gln Trp Pro Glu Glu Thr Phe Gly
225                 230                 235

<210> SEQ ID NO 57
<211> LENGTH: 714
<212> TYPE: DNA
<213> ORGANISM: artificial sequence
<220> FEATURE:
<223> OTHER INFORMATION: NC_002655 cI encoding gene

<400> SEQUENCE: 57
atgagcgcaa aaagaaaacc attaacacaa gagcagcttg aggacgcacg tcgccttaaa      60
gctatttatg aaaaaagaa aatgaacttt ggcttatccc aggaatctgt cgcagacaag     120
atggggatgg ggcagtcagg cgttggtgct ttatttaatg gcatcaatgc attaaatgct     180
tataacgccg cattgcttgc aaaaattctc aacgttagcg ttgaagaatt tagcccttca     240
atcgccagag aaatctacga gatgtatgaa gcggttagta tgcagccgtc acttagaagt     300
gagtatgagt accctgtttt ttctcatgtt caggccggga tgttctcgcc tgagcttaga     360
accttcacca aaggcgatgc ggagaaatgg gtaagcacaa ccaaaaaagc cagtggctct     420
gcattctggc ttgaggttga aggtaattcc atgaccgcac aacaggatc caagcccagc     480
tttcctgacg ggatgttaat tctggttgac cctgagcagg ctgttgagcc aggcgatttc     540
tgtatagcca gacttggtgg tgatgagttt accttcaaga aactgatcag ggatagcggt     600
caggtgtttc tacagccact aaacccacaa tacccaatga tcccatgcaa tgagagttgt     660
tccgttgtgg ggaaagttat cgctagtcag tggcctgaag agacgtttgg gtga           714

<210> SEQ ID NO 58
<211> LENGTH: 237
<212> TYPE: PRT
<213> ORGANISM: artificial sequence
<220> FEATURE:
<223> OTHER INFORMATION: ZP_04798993 cI repressor protein

<400> SEQUENCE: 58

Met Ser Thr Lys Lys Pro Leu Thr Gln Glu Gln Leu Glu Asp Ala
1               5                   10                  15
Arg Arg Leu Lys Ala Ile Tyr Glu Lys Arg Lys Asn Glu Leu Gly Leu
                20                  25                  30
Ser Gln Glu Ser Val Ala Asp Lys Met Gly Met Gly Gln Ser Gly Val
            35                  40                  45
Gly Ala Leu Phe Asn Gly Ile Asn Ala Leu Asn Ala Tyr Asn Ala Ala
        50                  55                  60
Leu Leu Thr Lys Ile Leu Lys Val Ser Val Glu Glu Phe Ser Pro Ser
65                  70                  75                  80
Ile Ala Arg Glu Ile Tyr Glu Met Tyr Glu Ala Val Ser Met Gln Pro
                85                  90                  95
```

Ser Leu Arg Ser Glu Tyr Glu Tyr Pro Val Phe Ser His Val Gln Ala
            100                 105                 110

Gly Met Phe Ser Pro Lys Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235

<210> SEQ ID NO 59
<211> LENGTH: 714
<212> TYPE: DNA
<213> ORGANISM: artificial sequence
<220> FEATURE:
<223> OTHER INFORMATION: NZ_ACJP01000210 cI encoding gene

<400> SEQUENCE: 59
atgagcacaa aaagaaaacc attaacacaa gagcagcttg aggacgcacg tcgcctttaaa      60 gcaatttatg aaaaaaggaa aaatgaactt ggcttatccc aggaatctgt cgcagacaag     120
atggggatgg ggcagtcagg cgttggtgct ttatttaatg gcatcaatgc attaaatgct     180
tataacgccg cattgcttac aaaaattctc aaagttagcg ttgaagaatt tagcccttca     240
atcgccagag aaatctacga gatgtatgaa gcggttagta tgcagccgtc acttagaagt     300
gagtatgagt accctgtttt ttctcatgtt caggcaggga tgttctcacc taagcttaga     360
acctttacca aggtgatgc ggagagatgg gtaagcacaa ccaaaaaagc cagtgattct     420
gcattctggc ttgaggttga aggtaattcc atgaccgcac caacaggctc aagccaagc     480 tttcctgacg gaatgttaat tctcgttgac cctgagcagg ctgttgagcc aggtgatttc     540
tgcatagcca gacttggggg tgatgagttt accttcaaga aactgatcag ggatagcggt     600
caggtgtttt tacaaccact aaacccacag taccccaatga tcccatgcaa tgagagttgt     660
tccgttgtgg ggaaagttat cgctagtcag tggcctgaag agacgtttgg ctga           714

<210> SEQ ID NO 60
<211> LENGTH: 473
<212> TYPE: PRT
<213> ORGANISM: artificial sequence
<220> FEATURE:
<223> OTHER INFORMATION: AAA72302 sacB protein

<400> SEQUENCE: 60

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

-continued

```
His Asp Met Leu Gln Ile Pro Glu Gln Gln Lys Asn Glu Lys Tyr Gln
     50                  55                  60

Val Pro Glu Phe Asp Ser Ser Thr Ile Lys Asn Ile Ser Ser Ala Lys
 65                  70                  75                  80

Gly Leu Glu Val Trp Asp Ser Trp Pro Leu Gln Asn Ala Asp Gly Thr
                     85                  90                  95

Val Ala Asn Tyr His Gly Tyr His Ile Val Phe Ala Leu Ala Gly Asp
                100                 105                 110

Pro Lys Asn Ala Asp Asp Thr Ser Ile Tyr Met Phe Tyr Gln Lys Val
                115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
                180                 185                 190

Thr Thr Ala Gln Val Asn Val Ser Ala Ser Asp Ser Ser Leu Asn Ile
                195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
                260                 265                 270

Gly Glu Glu Ser Leu Phe Asn Lys Ala Tyr Tyr Gly Lys Ser Thr Ser
                275                 280                 285

Phe Phe Arg Gln Glu Ser Gln Lys Leu Leu Gln Ser Asp Lys Lys Arg
                290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
                340                 345                 350

Trp Tyr Leu Phe Thr Asp Ser Arg Gly Ser Lys Met Thr Ile Asp Gly
                355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
                420                 425                 430

Arg Gly Phe Tyr Ala Asp Lys Gln Ser Thr Phe Ala Pro Ser Phe Leu
                435                 440                 445

Leu Asn Ile Lys Gly Lys Lys Thr Ser Val Val Lys Asp Ser Ile Leu
    450                 455                 460
```

Glu Gln Gly Gln Leu Thr Val Asn Lys
465                 470

<210> SEQ ID NO 61
<211> LENGTH: 1422
<212> TYPE: DNA
<213> ORGANISM: artificial sequence
<220> FEATURE:
<223> OTHER INFORMATION: L05081 sacB encoding gene

<400> SEQUENCE: 61

| | | | | | | |
|---|---|---|---|---|---|---|
| atgaacatca | aaaagtttgc | aaaacaagca | acagtattaa | cctttactac | cgcactgctg | 60 |
| gcaggaggcg | caactcaagc | gtttgcgaaa | gaaacgaacc | aaaagccata | taaggaaaca | 120 |
| tacggcattt | cccatattac | acgccatgat | atgctgcaaa | tccctgaaca | gcaaaaaaat | 180 |
| gaaaaatatc | aagttcctga | attcgattcg | tccacaatta | aaaatatctc | ttctgcaaaa | 240 |
| ggcctggagg | tttgggacag | ctggccatta | caaaacgctg | acggcactgt | cgcaaactat | 300 |
| cacggctacc | acatcgtctt | tgcattagcc | ggagatccta | aaaatgcgga | tgacacatcg | 360 |
| atttacatgt | tctatcaaaa | agtcggcgaa | acttctattg | acagctggaa | aaacgctggc | 420 |
| cgcgtcttta | aagacagcga | caaattcgat | gcaaatgatt | ctatcctaaa | agaccaaaca | 480 |
| caagaatggt | caggttcagc | cacatttaca | tctgacggaa | aaatccgttt | attctacact | 540 |
| gatttctccg | gtaaacatta | cggcaaacaa | acactgacaa | ctgcacaagt | taacgtatca | 600 |
| gcatcagaca | gctctttgaa | catcaacggt | gtagaggatt | ataaatcaat | ctttgacggt | 660 |
| gacggaaaaa | cgtatcaaaa | tgtacagcag | ttcatcgatg | aaggcaacta | cagctcaggc | 720 |
| gacaaccata | cgctgagaga | tcctcactac | gtagaagata | aaggccacaa | atacttagta | 780 |
| tttgaagcaa | acactggaac | tgaagatggc | taccaaggcg | aagaatcttt | atttaacaaa | 840 |
| gcatactatg | gcaaaagcac | atcattcttc | cgtcaagaaa | gtcaaaaact | tctgcaaagc | 900 |
| gataaaaaac | gcacggctga | gttagcaaac | ggcgctctcg | gtatgattga | gctaaacgat | 960 |
| gattacacac | tgaaaaaagt | gatgaaaccg | ctgattgcat | ctaacacagt | aacagatgaa | 1020 |
| attgaacgcg | cgaacgtctt | taaaatgaac | ggcaaatggt | acctgttcac | tgactcccgc | 1080 |
| ggatcaaaaa | tgacgattga | cggcattacg | tctaacgata | tttacatgct | ggttatgtt | 1140 |
| tctaattctt | taactggccc | atacaagccc | tgaacaaaa | ctggccttgt | gttaaaaatg | 1200 |
| gatcttgatc | ctaacgatgt | aacctttact | tactcacact | tcgctgtacc | tcaagcgaaa | 1260 |
| ggaaacaatg | tcgtgattac | aagctatatg | acaaacagag | gattctacgc | agacaaacaa | 1320 |
| tcaacgtttg | cgccaagctt | cctgctgaac | atcaaaggca | gaaaacatc | tgttgtcaaa | 1380 |
| gacagcatcc | ttgaacaagg | acaattaaca | gttaacaaat | aa | | 1422 |

<210> SEQ ID NO 62
<211> LENGTH: 473
<212> TYPE: PRT
<213> ORGANISM: artificial sequence
<220> FEATURE:
<223> OTHER INFORMATION: AAN75494 sacB protein

<400> SEQUENCE: 62

Met Asn Ile Lys Lys Phe Ala Lys Gln Ala Thr Val Leu Thr Phe Thr
1               5                   10                  15

Thr Ala Pro Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

```
His Asp Met Leu Gln Ile Pro Glu Gln Gln Lys Asn Glu Lys Tyr Gln
    50                  55                  60
Val Pro Glu Phe Asp Ser Ser Thr Ile Lys Asn Ile Ser Ser Ala Lys
65                  70                  75                  80
Gly Leu Asp Val Trp Asp Ser Trp Pro Leu Gln Asn Ala Asp Gly Thr
                    85                  90                  95
Val Ala Asn Tyr His Gly Tyr His Ile Val Phe Ala Leu Ala Gly Asp
                100                 105                 110
Pro Lys Asn Ala Asp Asp Thr Ser Ile Tyr Met Phe Tyr Gln Lys Val
                115                 120                 125
Gly Glu Thr Ser Ile Asp Ser Trp Lys Asn Ala Gly Arg Val Phe Lys
            130                 135                 140
Asp Ser Asp Lys Phe Asp Ala Asn Asp Ser Ile Leu Lys Asp Gln Thr
145                 150                 155                 160
Gln Glu Trp Ser Gly Ser Ala Thr Phe Thr Ser Asp Gly Lys Ile Arg
                165                 170                 175
Leu Phe Tyr Thr Asp Phe Ser Gly Lys His Tyr Gly Lys Gln Thr Leu
                180                 185                 190
Thr Thr Ala Gln Val Asn Val Ser Thr Ser Asp Ser Ser Leu Asn Ile
            195                 200                 205
Asn Gly Val Glu Asp His Lys Ser Ile Phe Asp Gly Asp Gly Lys Thr
            210                 215                 220
Tyr Gln Asn Val Gln Gln Phe Ile Asp Glu Gly Asn Tyr Ser Ser Gly
225                 230                 235                 240
Asp Asn His Thr Leu Arg Asp Pro His Tyr Val Glu Asp Lys Gly His
                245                 250                 255
Lys Tyr Leu Val Phe Glu Ala Asn Thr Gly Thr Glu Asp Gly Tyr Gln
                260                 265                 270
Gly Glu Glu Ser Leu Phe Asn Lys Ala Tyr Tyr Gly Lys Ser Thr Ser
            275                 280                 285
Phe Phe Arg Gln Glu Ser Gln Lys Leu Leu Gln Ser Asp Lys Lys Arg
            290                 295                 300
Thr Ala Glu Leu Ala Asn Gly Ala Leu Gly Met Ile Glu Leu Asn Asp
305                 310                 315                 320
Asp Tyr Thr Leu Lys Lys Val Met Lys Pro Leu Ile Thr Ser Asn Thr
                325                 330                 335
Val Thr Asp Glu Ile Glu Arg Ala Asn Val Phe Lys Met Asn Gly Lys
                340                 345                 350
Trp Tyr Leu Phe Thr Asp Ser Arg Gly Ser Lys Met Thr Ile Asp Gly
            355                 360                 365
Ile Thr Ser Asn Asp Ile Tyr Met Leu Gly Tyr Val Ser Asn Ser Leu
            370                 375                 380
Thr Gly Pro Tyr Lys Pro Leu Asn Lys Thr Gly Leu Val Leu Lys Met
385                 390                 395                 400
Asp Leu Asp Pro Asn Asp Val Thr Phe Thr Tyr Ser His Phe Ala Val
                405                 410                 415
Pro Gln Ala Lys Gly Asn Asn Val Val Ile Thr Ser Tyr Met Thr Asn
                420                 425                 430
Arg Gly Phe Tyr Ala Asp Lys Gln Ser Thr Phe Ala Pro Ser Phe Leu
            435                 440                 445
Leu Asn Ile Lys Gly Lys Lys Thr Ser Val Val Lys Asp Ser Ile Leu
            450                 455                 460
```

Glu Gln Gly Gln Leu Thr Val Asn Gln
465                 470

<210> SEQ ID NO 63
<211> LENGTH: 1422
<212> TYPE: DNA
<213> ORGANISM: artificial sequence
<220> FEATURE:
<223> OTHER INFORMATION: AY150365 sacB gene

<400> SEQUENCE: 63

```
atgaacatca aaagtttgc aaaacaagca acagtattaa cctttactac cgcaccgctg      60
gcaggaggcg caactcaagc gtttgcgaaa gaaacgaacc aaaagccata taaggaaaca    120
tacggcattt cccatattac acgccatgat atgctgcaaa tccctgaaca gcaaaaaaat    180
gaaaaatatc aagttcctga attcgattcg tccacaatta aaaatatctc ttctgcaaaa    240
ggcctggacg tttgggacag ctggccatta caaaacgctg acggcactgt cgcaaactat    300
cacggctacc acatcgtctt tgcattagcc ggagatccta aaaatgcgga tgacacatcg    360
atttacatgt tctatcaaaa agtcggcgaa acttctattg acagctggaa aaacgctggc    420
cgcgtcttta agacagcga caaattcgat gcaaatgatt ctatcctaaa agaccaaacg    480
caagaatggt caggttcagc tacatttaca tctgacggaa aaatccgttt attctacact    540
gatttctccg gtaaacatta cggcaaacaa cactgacaa ctgcacaagt taacgtatca    600
acatcagaca gctctttgaa catcaacggt gtagaggatc ataaatcaat ctttgacggc    660
gacggcaaaa cgtatcaaaa tgtacagcag ttcatcgatg aaggcaacta cagctcaggc    720
gataaccata cgctgagaga tcctcactac gtagaagata aaggccacaa atacttagta    780
tttgaagcaa acactggaac tgaagatggc taccaaggcg aagaatcttt atttaacaaa    840
gcatactatg gcaaaagcac atcattcttc cgtcaagaaa gtcaaaaact tctgcaaagc    900
gataaaaaac gcacggctga gttagcaaac ggcgctctcg gtatgattga gctaaacgat    960
gattacacac tgaaaaaagt gatgaaaccg ctgattacat ctaacacagt aacagatgaa   1020
attgaacgtg cgaatgtctt taaaatgaac ggcaaatggt acctgttcac tgactcccgc   1080
gggtcaaaaa tgacgattga cggcatcacg tctaacgata tttacatgct ggctatgtt   1140
tctaattctt taactggccc atacaagccg ctgaacaaaa ctggccttgt gttaaaaatg   1200
gatcttgatc ctaacgatgt aacctttact tactcacact cgctgtacc tcaagcgaaa   1260
ggaaacaatg tcgtgattac aagctatatg acaaacagag gattctacgc agacaaacaa   1320
tcaacgtttg caccaagctt cctgctgaac atcaaaggca gaaaacatc tgttgtcaaa   1380
gacagcatcc ttgaacaagg acaattaaca gttaaccaat aa                     1422
```

<210> SEQ ID NO 64
<211> LENGTH: 473
<212> TYPE: PRT
<213> ORGANISM: artificial sequence
<220> FEATURE:
<223> OTHER INFORMATION: ACD39394 sacB protein

<400> SEQUENCE: 64

Met Asn Ile Lys Lys Phe Ala Lys Arg Ala Thr Val Leu Thr Phe Thr
1               5                   10                  15

Thr Ala Leu Leu Ala Gly Gly Ala Thr Gln Ala Phe Ala Lys Glu Asn
            20                  25                  30

Thr Gln Lys Pro Tyr Lys Glu Thr Tyr Gly Val Ser His Ile Thr Arg
        35                  40                  45

```
His Asp Met Leu Gln Ile Pro Lys Gln Gln Ser Glu Lys Tyr Gln
    50                  55                  60

Val Pro Gln Phe Asp Pro Ser Thr Ile Lys Asn Ile Glu Ser Ala Lys
65                  70                  75                  80

Gly Leu Asp Val Trp Asp Ser Trp Pro Leu Gln Asn Ala Asp Gly Thr
                    85                  90                  95

Val Ala Glu Tyr Asn Gly Tyr His Val Val Phe Ala Leu Ala Gly Ser
                100                 105                 110

Pro Lys Asp Ala Asp Asp Thr Ser Ile Tyr Met Phe Tyr Gln Lys Val
                115                 120                 125

Gly Asp Asn Ser Ile Asp Ser Trp Lys Asn Ala Gly Arg Val Phe Lys
                130                 135                 140

Asp Ser Asp Lys Phe Asp Ala Asn Asp Glu Ile Leu Lys Glu Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Ser Leu
                180                 185                 190

Thr Thr Ala Gln Val Asn Val Ser Lys Ser Asp Asp Thr Leu Lys Ile
                195                 200                 205

Asn Gly Val Glu Asp His Lys Thr Ile Phe Asp Gly Asp Gly Lys Thr
                210                 215                 220

Tyr Gln Asn Val Gln Gln Phe Ile Asp Glu Gly Asn Tyr Thr Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asn Gly Tyr Gln
                260                 265                 270

Gly Glu Glu Ser Leu Phe Asn Lys Ala Tyr Tyr Gly Gly Ser Thr Asn
                275                 280                 285

Phe Phe Arg Lys Glu Ser Gln Lys Leu Gln Gln Ser Ala Lys Lys Arg
                290                 295                 300

Asp Ala Glu Leu Ala Asn Gly Ala Leu Gly Met Val Glu Leu Asn Asp
305                 310                 315                 320

Asp Tyr Thr Leu Lys Lys Val Met Lys Pro Leu Ile Thr Ser Asn Thr
                325                 330                 335

Val Thr Asp Glu Ile Glu Arg Ala Asn Val Phe Lys Met Asn Gly Lys
                340                 345                 350

Trp Tyr Leu Phe Thr Asp Ser Arg Gly Ser Lys Met Thr Ile Asp Gly
                355                 360                 365

Ile Asn Ser Asn Asp Ile Tyr Met Leu Gly Tyr Val Ser Asn Ser Leu
                370                 375                 380

Thr Gly Pro Tyr Lys Pro Leu Asn Lys Thr Gly Leu Val Leu Gln Met
385                 390                 395                 400

Gly Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
                420                 425                 430

Arg Gly Phe Phe Glu Asp Lys Lys Ala Thr Phe Ala Pro Ser Phe Leu
                435                 440                 445

Met Asn Ile Lys Gly Lys Lys Thr Ser Val Val Lys Asn Ser Ile Leu
    450                 455                 460
```

Glu Gln Gly Gln Leu Thr Val Asn Asn
465                 470

<210> SEQ ID NO 65
<211> LENGTH: 1419
<212> TYPE: DNA
<213> ORGANISM: artificial sequence
<220> FEATURE:
<223> OTHER INFORMATION: EU668142 sacB encoding gene

<400> SEQUENCE: 65

| | | | | | |
|---|---|---|---|---|---|
| atgaacatca | aaaaatttgc | aaaacgagcc | acagttctaa | cttttacgac | tgcacttctg | 60 |
| gcagggggag | cgactcaagc | cttcgcgaaa | gaaaataccc | aaaaacctta | caaagaaacg | 120 |
| tacggcgtct | ctcatatcac | acgccatgat | atgctgcaga | tccctaaaca | gcagcaaagt | 180 |
| gaaaaatacc | aagtgcctca | attcgaccca | tcaacaatta | aaaatatcga | gtccgcgaaa | 240 |
| ggactggatg | tgtgggacag | ctggccgctc | caaaacgctg | acggaacagt | agctgaatac | 300 |
| aacggctatc | acgtcgtgtt | tgctcttgcc | ggaagcccga | agacgctga | tgacacatcc | 360 |
| atctacatgt | tttatcaaaa | agtcggcgac | aactcgatcg | acagctggaa | aaacgcgggc | 420 |
| cgtgtcttta | aagacagcga | taagttcgac | gccaacgatg | aaatcctgaa | agaacagaca | 480 |
| caagaatggt | ccggttctgc | aacctttaca | tctgacggaa | aaatccgttt | attctacact | 540 |
| gacttttccg | gtaaacatta | cggcaaacaa | agcctgacaa | cggcgcaggt | aaatgtgtca | 600 |
| aaatctgatg | acacgctcaa | gatcaacgga | gtggaagatc | ataaaacgat | ttttgacggc | 660 |
| gacggaaaaa | catatcaaaa | cgttcagcag | tttatcgatg | aagggaacta | tacatccggc | 720 |
| gacaaccata | cgctgagaga | ccctcactac | gttgaagaca | aggacataa | ataccttgta | 780 |
| ttcgaagcca | acacgggaac | agaaaacgga | taccaaggcg | aagaatcttt | atttaacaaa | 840 |
| gcgtactacg | gcggcagcac | aaacttcttc | cgtaaagaaa | gtcagaagct | tcagcaaagc | 900 |
| gctaaaaaac | gcgatgctga | attagcgaac | ggcgccctcg | gtatggtaga | gttaaacgat | 960 |
| gattacacat | tgaaaaaagt | catgaagccg | ctgatcactt | caaacacggt | aactgatgaa | 1020 |
| atcgagcgcg | cgaatgtttt | caaaatgaac | ggcaaatggt | acctgttcac | tgattcacgc | 1080 |
| ggttcaaaaa | tgacgatcga | cggtattaac | tcaaacgata | tttacatgct | tggttatgta | 1140 |
| tcaaactctt | taacaggtcc | ttacaagccg | ctgaacaaaa | ctggtcttgt | cctgcaaatg | 1200 |
| ggtcttgatc | ctaacgatgt | aacgttcact | tactctcact | cgcagtgcc | gcaagccaaa | 1260 |
| ggcaacaatg | tcgtgatcac | aagctacatg | acaaacagag | gcttctttga | ggataaaaag | 1320 |
| gcgacatttg | cgccaagctt | cttaatgaac | atcaaaggca | gaaaacatc | cgttgttaaa | 1380 |
| aacagcatcc | ttgaacaagg | acagcttacg | gttaacaac | | | 1419 |

<210> SEQ ID NO 66
<211> LENGTH: 473
<212> TYPE: PRT
<213> ORGANISM: artificial sequence
<220> FEATURE:
<223> OTHER INFORMATION: AAZ04375 sacB protein

<400> SEQUENCE: 66

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
                20                  25                  30

Asn Gln Lys Pro Tyr Lys Glu Thr Tyr Gly Ile Ser His Ile Thr Arg
            35                  40                  45

-continued

His Asp Met Leu Gln Ile Pro Glu Gln Gln Lys Asn Glu Lys Tyr Arg
        50                  55                  60

Val Pro Glu Phe Asp Ser Ser Thr Ile Lys Asn Ile Ser Ser Ala Lys
 65                  70                  75                  80

Gly Leu Asp Val Trp Asp Ser Trp Pro Leu Gln Asn Ala Asp Gly Thr
                     85                  90                  95

Val Ala Asn Tyr His Gly Tyr His Ile Val Phe Ala Leu Ala Gly Asp
                100                 105                 110

Pro Lys Asn Ala Asp Asp Thr Ser Ile Tyr Met Phe Tyr Gln Lys Val
                115                 120                 125

Gly Glu Thr Ser Ile Asp Ser Trp Lys Asn Ala Gly Arg Val Phe Lys
            130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
                180                 185                 190

Thr Thr Ala Gln Val Asn Val Ser Ala Ser Asp Ser Ser Leu Asn Ile
            195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
                260                 265                 270

Gly Glu Glu Ser Leu Phe Asn Lys Ala Tyr Tyr Gly Lys Ser Thr Ser
            275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
                340                 345                 350

Trp Tyr Leu Phe Thr Asp Ser Arg Gly Ser Lys Met Thr Ile Asp Gly
            355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
                420                 425                 430

Arg Gly Phe Tyr Ala Asp Lys Gln Ser Thr Phe Ala Pro Ser Phe Leu
            435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470

<210> SEQ ID NO 67
<211> LENGTH: 1422
<212> TYPE: DNA
<213> ORGANISM: artificial sequence
<220> FEATURE:
<223> OTHER INFORMATION: DQ095874 sacB encoding gene

<400> SEQUENCE: 67

| | | | | | |
|---|---|---|---|---|---|
| atgaacatca | aaaagtttgc | aaaacaagca | acagtattaa | cctttactac | cgcactgctg | 60 |
| gcaggaggcg | caactcaagc | gtttgcgaaa | gaaacgaacc | aaaagccata | taaggaaaca | 120 |
| tacggcattt | cccatattac | acgccatgat | atgctgcaaa | tccctgaaca | gcaaaaaaat | 180 |
| gaaaaatatc | gagttcctga | attcgattcg | tccacaatta | aaaatatctc | ttctgcaaaa | 240 |
| ggcctggacg | tttgggacag | ctggccatta | caaaacgctg | acggcactgt | cgcaaactat | 300 |
| cacggctacc | acatcgtctt | tgcattagcc | ggagatccta | aaaatgcgga | tgacacatcg | 360 |
| atttacatgt | tctatcaaaa | agtcggcgaa | acttctattg | acagctggaa | aaacgctggc | 420 |
| cgcgtcttta | aagacagcga | caaattcgat | gcaaatgatt | ctatcctaaa | agaccaaaca | 480 |
| caagaatggt | caggttcagc | cacatttaca | tctgacggaa | aaatccgttt | attctacact | 540 |
| gatttctccg | gtaaacatta | cggcaaacaa | cactgacaa | ctgcacaagt | taacgtatca | 600 |
| gcatcagaca | gctctttgaa | catcaacggt | gtagaggatt | ataaatcaat | ctttgacggt | 660 |
| gacggaaaaa | cgtatcaaaa | tgtacagcag | ttcatcgatg | aaggcaacta | cagctcaggc | 720 |
| gacaaccata | cgctgagaga | tcctcactac | gtagaagata | aaggccacaa | atacttagta | 780 |
| tttgaagcaa | acactggaac | tgaagatggc | taccaaggcg | aagaatcttt | atttaacaaa | 840 |
| gcatactatg | gcaaaagcac | atcattcttc | cgtcaagaaa | gtcaaaaact | tctgcaaagc | 900 |
| gataaaaaac | gcacggctga | gttagcaaac | ggcgctctcg | gtatgattga | gctaaacgat | 960 |
| gattacacac | tgaaaaaagt | gatgaaaccg | ctgattgcat | ctaacacagt | aacagatgaa | 1020 |
| attgaacgcg | cgaacgtctt | taaaatgaac | ggcaaatggt | acctgttcac | tgactcccgc | 1080 |
| ggatcaaaaa | tgacgattga | cggcattacg | tctaacgata | tttacatgct | tggttatgtt | 1140 |
| tctaattctt | taactggccc | atacaagccg | ctgaacaaaa | ctggccttgt | gttaaaaatg | 1200 |
| gatcttgatc | ctaacgatgt | aacctttact | tactcacact | cgctgtacc | tcaagcgaaa | 1260 |
| ggaaacaatg | tcgtgattac | aagctatatg | acaaacagag | gattctacgc | agacaaacaa | 1320 |
| tcaacgtttg | cgccaagctt | cctgctgaac | atcaaaggca | gaaaacatc | tgttgtcaaa | 1380 |
| gacagcatcc | ttgaacaagg | acaattaaca | gttaacaaat | aa | | 1422 |

<210> SEQ ID NO 68
<211> LENGTH: 473
<212> TYPE: PRT
<213> ORGANISM: artificial sequence
<220> FEATURE:
<223> OTHER INFORMATION: ABM88723 sacB protein

<400> SEQUENCE: 68

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

```
His Asp Met Leu Gln Ile Pro Glu Gln Gln Lys Asn Glu Lys Tyr Lys
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Thr Asp Gly Thr
                    85                  90                  95

Val Ala Asn Tyr His Gly Tyr His Ile Val Phe Ala Leu Ala Gly Asp
                100                 105                 110

Pro Lys Asn Ala Asp Asp Thr Ser Ile Tyr Met Phe Tyr Gln Lys Val
                115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
                180                 185                 190

Thr Thr Ala Gln Val Asn Val Ser Ala Ser Asp Ser Ser Leu Asn Ile
    195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
                260                 265                 270

Gly Glu Glu Ser Leu Phe Asn Lys Ala Tyr Tyr Gly Lys Ser Thr Ser
    275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
                340                 345                 350

Trp Tyr Leu Phe Thr Asp Ser Arg Gly Ser Lys Met Thr Ile Asp Gly
                355                 360                 365

Ile Thr Ser Asn Asp Ile Tyr Met Leu Gly Tyr Val Ser Asn Ser Leu
                370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
                420                 425                 430

Arg Gly Phe Tyr Ala Asp Lys Gln Ser Thr Phe Ala Pro Ser Phe Leu
                435                 440                 445

Leu Asn Ile Lys Gly Lys Lys Thr Ser Val Val Lys Asp Ser Ile Leu
                450                 455                 460
```

Glu Gln Gly Gln Leu Thr Val Asn Lys
465                 470

<210> SEQ ID NO 69
<211> LENGTH: 1422
<212> TYPE: DNA
<213> ORGANISM: artificial sequence
<220> FEATURE:
<223> OTHER INFORMATION: EF198106 sacB encoding gene

<400> SEQUENCE: 69

```
atgaacatca aaagtttgc aaaacaagca acagtattaa cctttactac cgcactgctg     60
gcaggaggcg caactcaagc gtttgcgaaa gaaacgaacc aaaagccata aaggaaaca   120
tacggcattt cccatattac acgccatgat atgctgcaaa tccctgaaca gcaaaaaaat   180
gaaaaatata aagttcctga gttcgattcg tccacaatta aaaatatctc ttctgcaaaa   240
ggcctggacg tttgggacag ctggccatta caaaacactg acggcactgt cgcaaactat   300
cacggctacc acatcgtctt tgcattagcc ggagatccta aaaatgcgga tgacacatcg   360
atttacatgt tctatcaaaa agtcggcgaa acttctattg acagctggaa aaacgctggc   420
cgcgtcttta aagacagcga caaattcgat gcaaatgatt ctatcctaaa agaccaaaca   480
caagaatggt caggttcagc cacatttaca tctgacggaa aaatccgttt attctacact   540
gatttctccg gtaaacatta cggcaaacaa acactgacaa ctgcacaagt taacgtatca   600
gcatcagaca gctctttgaa catcaacggt gtagaggatt ataaatcaat ctttgacggt   660
gacggaaaaa cgtatcaaaa tgtacagcag ttcatcgatg aaggcaacta cagctcaggc   720
gacaaccata cgctgagaga tcctcactac gtagaagata aaggccacaa atacttagta   780
tttgaagcaa acactggaac tgaagatggc taccaaggcg aagaatcttt atttaacaaa   840
gcatactatg gcaaaagcac atcattcttc cgtcaagaaa gtcaaaaact tctgcaaagc   900
gataaaaaac gcacggctga gttagcaaac ggcgctctcg gtatgattga gctaaacgat   960
gattacacac tgaaaaaagt gatgaaaccg ctgattgcat ctaacacagt aacagatgaa  1020
attgaacgcg cgaacgtctt taaaatgaac ggcaaatggt acctgttcac tgactcccgc  1080
ggatcaaaaa tgacgattga cggcattacg tctaacgata tttacatgct ggttatgtt   1140
tctaattctt taactggccc atacaagccc ctgaacaaaa ctggccttgt gttaaaaatg  1200
gatcttgatc ctaacgatgt aacctttact tactcacact cgctgtacc tcaagcgaaa  1260
ggaaacaatg tcgtgattac aagctatatg acaaacagag gattctacgc agacaaacaa  1320
tcaacgtttg cgcctagctt cctgctgaac atcaaaggca gaaaacatc tgttgtcaaa  1380
gacagcatcc ttgaacaagg acaattaaca gttaacaaat aa                     1422
```

<210> SEQ ID NO 70
<211> LENGTH: 473
<212> TYPE: PRT
<213> ORGANISM: artificial sequence
<220> FEATURE:
<223> OTHER INFORMATION: ACJ66845 sacB protein

<400> SEQUENCE: 70

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

```
His Asp Met Leu Gln Ile Pro Glu Gln Gln Lys Asn Glu Lys Tyr Gln
        50                  55                  60
Val Ser Glu Phe Asp Ser Ser Thr Ile Lys Asn Ile Ser Ala Lys
 65                  70                  75                  80
Gly Leu Asp Val Trp Asp Ser Trp Pro Leu Gln Asn Ala Asp Gly Thr
                        85                  90                  95
Val Ala Asn Tyr His Gly Tyr His Ile Val Phe Ala Leu Ala Gly Asp
                100                 105                 110
Pro Lys Asn Ala Asp Asp Thr Ser Ile Tyr Met Phe Tyr Gln Lys Val
                115                 120                 125
Gly Glu Thr Ser Ile Asp Ser Trp Lys Asn Ala Gly Arg Val Phe Lys
    130                 135                 140
Asp Ser Asp Lys Phe Asp Ala Asn Asp Ser Ile Leu Lys Asp Gln Thr
145                 150                 155                 160
Gln Glu Trp Ser Gly Ser Ala Thr Phe Thr Ser Asp Gly Lys Ile Arg
                165                 170                 175
Leu Phe Tyr Thr Asp Phe Ser Gly Lys His Tyr Gly Lys Gln Thr Leu
                180                 185                 190
Thr Thr Ala Gln Val Asn Val Ser Ala Ser Asp Ser Ser Leu Asn Ile
        195                 200                 205
Asn Gly Val Glu Asp Tyr Lys Ser Ile Phe Asp Gly Asp Gly Lys Thr
    210                 215                 220
Tyr Gln Asn Val Gln Gln Phe Ile Asp Glu Gly Asn Tyr Ser Ser Gly
225                 230                 235                 240
Asp Asn His Thr Leu Arg Asp Pro His Tyr Val Glu Asp Lys Gly His
                245                 250                 255
Lys Tyr Leu Val Phe Glu Ala Asn Thr Gly Thr Glu Asp Gly Tyr Gln
                260                 265                 270
Gly Glu Glu Ser Leu Phe Asn Lys Ala Tyr Tyr Gly Lys Ser Thr Ser
                275                 280                 285
Phe Phe Arg Gln Glu Ser Gln Lys Leu Leu Gln Ser Asp Lys Lys Arg
            290                 295                 300
Thr Ala Glu Leu Ala Asn Gly Ala Leu Gly Met Ile Glu Leu Asn Asp
305                 310                 315                 320
Asp Tyr Thr Leu Lys Lys Val Met Lys Pro Leu Ile Ala Ser Asn Thr
                325                 330                 335
Val Thr Asp Glu Ile Glu Arg Ala Asn Val Phe Lys Met Asn Gly Lys
                340                 345                 350
Trp Tyr Leu Phe Thr Asp Ser Arg Gly Ser Lys Met Thr Ile Asp Gly
            355                 360                 365
Ile Thr Ser Asn Asp Ile Tyr Met Leu Gly Tyr Val Ser Asn Ser Leu
        370                 375                 380
Thr Gly Pro Tyr Lys Pro Leu Asn Lys Thr Gly Leu Val Leu Lys Met
385                 390                 395                 400
Asp Leu Asp Pro Asn Asp Val Thr Phe Thr Tyr Ser His Phe Ala Val
                405                 410                 415
Pro Gln Ala Lys Gly Asn Asn Val Val Ile Thr Ser Tyr Met Thr Asn
                420                 425                 430
Arg Gly Phe Tyr Ala Asp Lys Gln Ser Thr Phe Ala Pro Ser Phe Leu
            435                 440                 445
Leu Asn Ile Lys Gly Lys Lys Thr Ser Val Val Lys Asp Ser Ile Leu
        450                 455                 460
```

Glu Gln Gly Gln Leu Thr Val Asn Lys
465                 470

<210> SEQ ID NO 71
<211> LENGTH: 1422
<212> TYPE: PRT
<213> ORGANISM: artificial sequence
<220> FEATURE:
<223> OTHER INFORMATION: FJ437239 sacB protein

<400> SEQUENCE: 71

Ala Thr Gly Ala Ala Cys Ala Thr Cys Ala Ala Ala Ala Gly Thr
1               5                   10                  15

Thr Thr Gly Cys Ala Ala Ala Ala Cys Ala Ala Gly Cys Ala Cys
                20                  25                  30

Ala Gly Thr Ala Thr Ala Ala Cys Thr Thr Thr Ala Cys Thr
                35                  40                  45

Ala Cys Cys Gly Cys Ala Cys Thr Gly Cys Thr Gly Gly Cys Ala Gly
            50                  55                  60

Gly Ala Gly Gly Cys Gly Cys Ala Ala Cys Thr Cys Ala Ala Gly Cys
65                  70                  75                  80

Gly Thr Thr Thr Gly Cys Gly Ala Ala Gly Ala Ala Cys Gly
                85                  90                  95

Ala Ala Cys Cys Ala Ala Ala Gly Cys Cys Ala Thr Ala Thr Ala
                100                 105                 110

Ala Gly Gly Ala Ala Cys Ala Thr Ala Cys Gly Gly Cys Ala Thr
                115                 120                 125

Thr Thr Cys Cys Cys Ala Thr Ala Thr Ala Cys Ala Cys Gly Cys
                130                 135                 140

Cys Ala Thr Gly Ala Thr Ala Thr Gly Cys Gly Cys Ala Ala Ala
145                 150                 155                 160

Thr Cys Cys Cys Thr Gly Ala Ala Cys Gly Cys Ala Ala Ala Ala
                165                 170                 175

Ala Ala Ala Thr Gly Ala Ala Ala Ala Thr Ala Thr Cys Ala Ala
                180                 185                 190

Gly Thr Thr Thr Cys Thr Gly Ala Ala Thr Thr Thr Gly Ala Thr Thr
                195                 200                 205

Cys Gly Thr Cys Thr Ala Cys Ala Ala Thr Thr Ala Ala Ala Ala
                210                 215                 220

Thr Ala Thr Cys Thr Cys Thr Thr Cys Thr Gly Cys Ala Ala Ala
225                 230                 235                 240

Gly Gly Cys Cys Thr Gly Gly Ala Cys Gly Thr Thr Gly Gly Gly
                245                 250                 255

Ala Cys Ala Gly Cys Thr Gly Gly Cys Cys Ala Thr Ala Cys Ala
                260                 265                 270

Ala Ala Cys Gly Cys Thr Gly Ala Cys Gly Gly Cys Ala Cys Thr
                275                 280                 285

Gly Thr Cys Gly Cys Ala Ala Ala Cys Thr Ala Thr Cys Ala Cys Gly
                290                 295                 300

Gly Cys Thr Ala Cys Cys Ala Cys Ala Thr Cys Gly Thr Cys Thr Thr
305                 310                 315                 320

Thr Gly Cys Ala Thr Thr Ala Gly Cys Cys Gly Gly Ala Gly Ala Thr
                325                 330                 335

Cys Cys Thr Ala Ala Ala Ala Thr Gly Cys Gly Gly Ala Thr Gly
                340                 345                 350

-continued

```
Ala Cys Ala Cys Ala Thr Cys Gly Ala Thr Thr Thr Ala Cys Ala Thr
        355                 360                 365

Gly Thr Thr Cys Thr Ala Thr Cys Ala Ala Ala Ala Ala Gly Thr Cys
    370                 375                 380

Gly Gly Cys Gly Ala Ala Ala Cys Thr Thr Cys Thr Ala Thr Thr Gly
385                 390                 395                 400

Ala Cys Ala Gly Cys Thr Gly Gly Ala Ala Ala Ala Ala Cys Gly Cys
                405                 410                 415

Thr Gly Gly Cys Cys Gly Cys Gly Thr Cys Thr Thr Thr Ala Ala Ala
            420                 425                 430

Gly Ala Cys Ala Gly Cys Gly Ala Cys Ala Ala Ala Thr Thr Cys Gly
        435                 440                 445

Ala Thr Gly Cys Ala Ala Ala Thr Gly Ala Thr Thr Cys Thr Ala Thr
    450                 455                 460

Cys Cys Thr Ala Ala Ala Ala Gly Ala Cys Cys Ala Ala Ala Cys Ala
465                 470                 475                 480
Cys Ala Ala Gly Ala Ala Thr Gly Gly Thr Cys Ala Gly Gly Thr Thr
                485                 490                 495

Cys Ala Gly Cys Cys Ala Cys Ala Thr Thr Thr Ala Cys Ala Thr Cys
            500                 505                 510

Thr Gly Ala Cys Gly Gly Ala Ala Ala Ala Ala Thr Cys Cys Gly Thr
        515                 520                 525

Thr Thr Ala Thr Thr Cys Thr Ala Cys Ala Cys Thr Gly Ala Thr Thr
    530                 535                 540

Thr Cys Thr Cys Cys Gly Gly Thr Ala Ala Ala Cys Ala Thr Thr Ala
545                 550                 555                 560

Cys Gly Gly Cys Ala Ala Ala Cys Ala Ala Ala Cys Ala Cys Thr Gly
                565                 570                 575
Ala Cys Ala Ala Cys Thr Gly Cys Ala Cys Ala Ala Gly Thr Thr Ala
            580                 585                 590

Ala Cys Gly Thr Ala Thr Cys Ala Gly Cys Ala Thr Cys Ala Gly Ala
        595                 600                 605

Cys Ala Gly Cys Thr Cys Thr Thr Thr Gly Ala Ala Cys Ala Thr Cys
    610                 615                 620

Ala Ala Cys Gly Gly Thr Gly Thr Ala Gly Ala Gly Gly Ala Thr Thr
625                 630                 635                 640

Ala Thr Ala Ala Ala Thr Cys Ala Ala Thr Cys Thr Thr Thr Gly Ala
                645                 650                 655

Cys Gly Gly Thr Gly Ala Cys Gly Gly Ala Ala Ala Ala Ala Cys Gly
            660                 665                 670

Thr Ala Thr Cys Ala Ala Ala Ala Thr Gly Thr Ala Cys Ala Gly Cys
        675                 680                 685

Ala Gly Thr Thr Cys Ala Thr Cys Gly Ala Thr Gly Ala Ala Gly Gly
    690                 695                 700

Cys Ala Ala Cys Thr Ala Cys Ala Gly Cys Thr Cys Ala Gly Gly Cys
705                 710                 715                 720

Gly Ala Cys Ala Ala Cys Cys Ala Thr Ala Cys Gly Cys Thr Gly Ala
                725                 730                 735

Gly Ala Gly Ala Thr Cys Cys Thr Cys Ala Cys Thr Ala Cys Gly Thr
            740                 745                 750

Ala Gly Ala Ala Gly Ala Thr Ala Ala Ala Gly Gly Cys Cys Ala Cys
        755                 760                 765

Ala Ala Ala Thr Ala Cys Thr Thr Ala Gly Thr Ala Thr Thr Thr Gly
```

-continued

```
    770                 775                 780

Ala Ala Gly Cys Ala Ala Ala Cys Ala Cys Thr Gly Gly Ala Ala Cys
785                 790                 795                 800

Thr Gly Ala Ala Gly Ala Thr Gly Gly Cys Thr Ala Cys Cys Ala Ala
                805                 810                 815

Gly Gly Cys Gly Ala Ala Gly Ala Ala Thr Cys Thr Thr Thr Ala Thr
            820                 825                 830

Thr Thr Ala Ala Cys Ala Ala Ala Gly Cys Ala Thr Ala Cys Thr Ala
        835                 840                 845

Thr Gly Gly Cys Ala Ala Ala Ala Gly Cys Ala Cys Ala Thr Cys Ala
    850                 855                 860

Thr Thr Cys Thr Thr Cys Cys Gly Thr Cys Ala Ala Gly Ala Ala Ala
865                 870                 875                 880

Gly Thr Cys Ala Ala Ala Ala Ala Cys Thr Thr Cys Thr Gly Cys Ala
                885                 890                 895

Ala Ala Gly Cys Gly Ala Thr Ala Ala Ala Ala Ala Ala Cys Gly Cys
            900                 905                 910

Ala Cys Gly Gly Cys Thr Gly Ala Gly Thr Thr Ala Gly Cys Ala Ala
        915                 920                 925

Ala Cys Gly Gly Cys Gly Cys Thr Cys Thr Cys Gly Gly Thr Ala Thr
    930                 935                 940

Gly Ala Thr Thr Gly Ala Gly Cys Thr Ala Ala Ala Cys Gly Ala Thr
945                 950                 955                 960

Gly Ala Thr Thr Ala Cys Ala Cys Ala Cys Thr Gly Ala Ala Ala Ala
                965                 970                 975

Ala Ala Gly Thr Gly Ala Thr Gly Ala Ala Ala Cys Cys Gly Cys Thr
            980                 985                 990

Gly Ala Thr Thr Gly Cys Ala Thr  Cys Thr Ala Ala Cys  Ala Cys Ala
        995                 1000                1005

Gly Thr  Ala Ala Cys Ala Gly  Ala Thr Gly Ala Ala  Ala Thr Thr
    1010                1015                1020

Gly Ala  Ala Cys Gly Cys Gly  Cys Gly Ala Ala Cys  Gly Thr Cys
    1025                1030                1035

Thr Thr  Thr Ala Ala Ala Ala  Thr Gly Ala Ala Cys  Gly Gly Cys
    1040                1045                1050

Ala Ala  Ala Thr Gly Gly Thr  Ala Cys Cys Thr Gly  Thr Thr Cys
    1055                1060                1065

Ala Cys  Thr Gly Ala Cys Thr  Cys Cys Cys Gly Cys  Gly Gly Ala
    1070                1075                1080

Thr Cys  Ala Ala Ala Ala Ala  Thr Gly Ala Cys Gly  Ala Thr Thr
    1085                1090                1095

Gly Ala  Cys Gly Gly Cys Ala  Thr Thr Ala Cys Gly  Thr Cys Thr
    1100                1105                1110

Ala Ala  Cys Gly Ala Thr Ala  Thr Thr Thr Ala Cys  Ala Thr Gly
    1115                1120                1125

Cys Thr  Thr Gly Gly Thr Thr  Ala Thr Gly Thr Thr  Thr Cys Thr
    1130                1135                1140

Ala Ala  Thr Thr Cys Thr Thr  Thr Ala Ala Cys Thr  Gly Gly Cys
    1145                1150                1155

Cys Cys  Ala Thr Ala Cys Ala  Ala Gly Cys Cys Gly  Cys Thr Gly
    1160                1165                1170

Ala Ala  Cys Ala Ala Ala Ala  Cys Thr Gly Gly Cys  Cys Thr Thr
    1175                1180                1185
```

Gly Thr Gly Thr Thr Ala Ala Ala Ala Thr Gly Gly Ala Thr
        1190                1195                1200

Cys Thr Thr Gly Ala Thr Cys Cys Thr Ala Ala Cys Gly Ala Thr
        1205                1210                1215

Gly Thr Ala Ala Cys Cys Thr Thr Thr Ala Cys Thr Thr Ala Cys
        1220                1225                1230

Thr Cys Ala Cys Ala Cys Thr Thr Cys Gly Cys Thr Gly Thr Ala
        1235                1240                1245

Cys Cys Thr Cys Ala Ala Gly Cys Gly Ala Ala Gly Gly Ala
        1250                1255                1260

Ala Ala Cys Ala Ala Thr Gly Thr Cys Gly Thr Gly Ala Thr Thr
        1265                1270                1275

Ala Cys Ala Ala Gly Cys Thr Ala Thr Ala Thr Gly Ala Cys Ala
        1280                1285                1290

Ala Ala Cys Ala Gly Ala Gly Gly Ala Thr Thr Cys Thr Ala Cys
        1295                1300                1305

Gly Cys Ala Gly Ala Cys Ala Ala Ala Cys Ala Ala Thr Cys Ala
        1310                1315                1320

Ala Cys Gly Thr Thr Thr Gly Cys Gly Cys Cys Gly Ala Gly Cys
        1325                1330                1335

Thr Thr Cys Cys Thr Gly Cys Thr Gly Ala Ala Cys Ala Thr Cys
        1340                1345                1350

Ala Ala Ala Gly Gly Cys Ala Ala Gly Ala Ala Ala Ala Cys Ala
        1355                1360                1365

Thr Cys Thr Gly Thr Thr Gly Thr Cys Ala Ala Ala Gly Ala Cys
        1370                1375                1380

Ala Gly Cys Ala Thr Cys Cys Thr Thr Gly Ala Ala Cys Ala Ala
        1385                1390                1395

Gly Gly Ala Cys Ala Ala Thr Thr Ala Ala Cys Ala Gly Thr Thr
        1400                1405                1410

Ala Ala Cys Ala Ala Ala Thr Ala Ala
        1415                1420

<210> SEQ ID NO 72
<211> LENGTH: 473
<212> TYPE: PRT
<213> ORGANISM: artificial sequence
<220> FEATURE:
<223> OTHER INFORMATION: NP_391325 sacB protein

<400> SEQUENCE: 72

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
            115                 120                 125

Gly Glu Thr Ser Ile Asp Ser Trp Lys Asn Ala Gly Arg Val Phe Lys
        130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470

<210> SEQ ID NO 73
<211> LENGTH: 1422
<212> TYPE: DNA
<213> ORGANISM: artificial sequence
<220> FEATURE:
<223> OTHER INFORMATION: NC_000964 sacB gene

<400> SEQUENCE: 73

```
atgaacatca aaaagtttgc aaaacaagca acagtattaa cctttactac cgcactgctg      60
gcaggaggcg caactcaagc gtttgcgaaa gaaacgaacc aaaagccata taaggaaaca     120
tacggcattt cccatattac acgccatgat atgctgcaaa tccctgaaca gcaaaaaaat     180 gaaaatatc aagttcctga attcgattcg tccacaatta aaaatatctc ttctgcaaaa     240
ggcctggacg tttgggacag ctggccatta caaaacgctg acggactgt cgcaaactat     300 cacggctacc acatcgtctt tgcattagcc ggagatccta aaaatgcgga tgacacatcg     360
atttacatgt tctatcaaaa agtcggcgaa acttctattg acagctggaa aaacgctggc     420
cgcgtcttta agacagcga caaattcgat gcaaatgatt ctatcctaaa agaccaaaca     480
caagaatggt caggttcagc cacatttaca tctgacggaa aaatccgttt attctacact     540
gatttctccg gtaaacatta cggcaaacaa acactgacaa ctgcacaagt taacgtatca     600
gcatcagaca gctctttgaa catcaacggt gtagaggatt ataaatcaat ctttgacggt     660
gacggaaaaa cgtatcaaaa tgtacagcag ttcatcgatg aaggcaacta cagctcaggc     720
gacaaccata cgctgagaga tcctcactac gtagaagata aaggccacaa atacttagta     780
tttgaagcaa acactggaac tgaagatggc taccaaggcg aagaatcttt atttaacaaa     840
gcatactatg gcaaaagcac atcattcttc cgtcaagaaa gtcaaaaact tctgcaaagc     900
gataaaaaac gcacggctga gttagcaaac ggcgctctcg gtatgattga gctaaacgat     960
gattacacac tgaaaaaagt gatgaaaccg ctgattgcat ctaacacagt aacagatgaa    1020
attgaacgcg cgaacgtctt taaaatgaac ggcaaatggt acctgttcac tgactcccgc    1080
ggatcaaaaa tgacgattga cggcattacg tctaacgata tttacatgct tggttatgtt    1140
tctaattctt taactggccc atacaagccg ctgaacaaaa ctggccttgt gttaaaaatg    1200
gatcttgatc ctaacgatgt aaccttact tactcacact cgctgtacc tcaagcgaaa    1260 ggaaacaatg tcgtgattac aagctatatg acaaacagag gattctacgc agacaaacaa    1320
tcaacgtttg cgccaagctt cctgctgaac atcaaaggca agaaaacatc tgttgtcaaa    1380
gacagcatcc ttgaacaagg acaattaaca gttaacaaat aa                      1422
```

<210> SEQ ID NO 74
<211> LENGTH: 473
<212> TYPE: PRT
<213> ORGANISM: artificial sequence
<220> FEATURE:
<223> OTHER INFORMATION: P94468 sacB protein

<400> SEQUENCE: 74

```
Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
            85                  90                  95

Val Ala Asn Tyr His Gly Tyr His Ile Val Phe Ala Leu Ala Gly Asp
            100                 105                 110
```

Pro Lys Asn Ala Asp Asp Thr Ser Ile Tyr Met Phe Tyr Gln Lys Val
        115                 120                 125

Gly Glu Thr Ser Ile Asp Ser Trp Lys Thr Pro Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Ser Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Asn Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Ser Thr Asp Ser Arg Gly Ser Gln Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Thr Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Gln Gly Lys Lys Thr Ser Val Val Lys Ala Ser Ile Leu
    450                 455                 460

Asp Gln Gly Gln Leu Thr Val Asn Gln
465                 470

<210> SEQ ID NO 75
<211> LENGTH: 1591
<212> TYPE: DNA
<213> ORGANISM: artificial sequence
<220> FEATURE:
<223> OTHER INFORMATION: lambda right promoter + sacB gene

<400> SEQUENCE: 75

```
ttgactattt tacctctggc ggtgataatg gttgcatgta ctaaggaggt tgtatggaac    60
aacgcataac cctgaaagat tatgcaatgc gctttgggca aaccaagaca gctaaagatc   120
acttaaatcg accagtaaca ggtggccttt tgaagaggat cagatggata tgaacatcaa   180
aaagtttgca aaacaagcaa cagtattaac ctttactacc gcactgctgg caggaggcgc   240
aactcaagcg tttgcgaaag aaacgaacca aaagccatat aaggaaacat acggcatttc   300
ccatattaca cgccatgata tgctgcaaat ccctgaacag caaaaaaatg aaaaatatca   360
agttcctgaa ttcgattcgt ccacaattaa aaatatctct tctgcaaaag gcctggacgt   420 tgggacagc tggccattac aaaacgctga cggcactgtc gcaaactatc acggctacca   480
catcgtcttt gcattagccg agatcctaa aaatgcggat gacacatcga tttacatgtt   540
ctatcaaaaa gtcggcgaaa cttctattga cagctggaaa aacgctggcc gcgtctttaa   600
agacagcgac aaattcgatg caaatgattc tatcctaaaa gaccaaacac aagaatggtc   660
aggttcagcc acatttacat ctgacggaaa aatccgttta ttctacactg atttctccgg   720
taaacattac ggcaaacaaa cactgacaac tgcacaagtt aacgtatcag catcagacag   780
ctctttgaac atcaacggtg tagaggatta taaatcaatc tttgacggtg acggaaaaac   840
gtatcaaaat gtacagcagt tcatcgatga aggcaactac agctcaggcg acaaccatac   900
gctgagagat cctcactacg tagaagataa aggccacaaa tacttagtat ttgaagcaaa   960
cactggaact gaagatggct accaaggcga agaatcttta tttaacaaag catactatgg  1020
caaaagcaca tcattcttcc gtcaagaaag tcaaaaactt ctgcaaagcg ataaaaaacg  1080
cacggctgag ttagcaaacg gcgctctcgg tatgattgag ctaaacgatg attacacact  1140
gaaaaaagtg atgaaccgc tgattgcatc taacacagta acagatgaaa ttgaacgcgc  1200
gaacgtcttt aaaatgaacg gcaaatggta cctgttcact gactcccgcg atcaaaaat  1260 gacgattgac ggcattacgt ctaacgatat ttacatgctt ggttatgttt ctaattcttt  1320
aactggccca tacaagccgc tgaacaaaac tggccttgtg ttaaaaatgg atcttgatcc  1380
taacgatgta acctttactt actcacactt cgctgtacct caagcgaaag gaaacaatgt  1440
cgtgattaca agctatatga caaacagagg attctacgca gacaaacaat caacgtttgc  1500
gccaagcttc ctgctgaaca tcaaaggcaa gaaaacatct gttgtcaaag acagcatcct  1560
tgaacaagga caattaacag ttaacaaata a                                 1591
```

<210> SEQ ID NO 76
<211> LENGTH: 849
<212> TYPE: DNA
<213> ORGANISM: artificial sequence
<220> FEATURE:
<223> OTHER INFORMATION: P1 promoter + cI gene in pPB829

<400> SEQUENCE: 76

```
gtgatacgcc tatttttata ggttaatgtc atgataataa tggtttctta gacgtcaggt    60 ggcactttc ggggaaatgt gcgcggaacc ccatttaaat tgtctgctta cataaacagt   120
aatacaaggg gtgttatgag cacaaaaaag aaaccattaa cacaagagca gcttgaggac   180
gcacgtcgcc ttaaagcaat ttatgaaaaa agaaaaatg aacttggctt atcccaggaa   240
tctgtcgcag acaagatggg gatgggcag tcaggcgttg gtgctttatt taatggcatc   300
aatgcattaa atgcttataa cgccgcattg cttacaaaaa ttctcaaagt tagcgttgaa   360
gaatttagcc cttcaatcgc cagagaaatc tacgagatgt atgaagcggt tagtatgcag  420
```

```
ccgtcactta aagtgagta tgagtaccct gttttttctc atgttcaggc agggatgttc      480
tcacctaagc ttagaacctt taccaaaggt gatgcggaga gatgggtaag cacaaccaaa      540
aaagccagtg attctgcatt ctggcttgag gttgaaggta attccatgac cgcaccaaca      600
ggctccaagc caagctttcc tgacggaatg ttaattctcg ttgaccctga gcaggctgtt      660
gagccaggtg atttctgcat agccagactt gggggtgatg agtttacctt caagaaactg      720
atcagggata gcggtcaggt gttttacaa ccactaaacc cacagtaccc aatgatccca      780
tgcaatgaga gttgttccgt tgtggggaaa gttatcgcta gtcagtggcc tgaagagacg      840
tttggctga                                                              849

<210> SEQ ID NO 77
<211> LENGTH: 751
<212> TYPE: DNA
<213> ORGANISM: artificial sequence
<220> FEATURE:
<223> OTHER INFORMATION: cI native promoter + cI gene in pPB846 and
      pPB847

<400> SEQUENCE: 77
ggtgttagat atttatccct tgcggtgata gatttaacgt atgagcacaa aaaagaaacc       60
attaacacaa gagcagcttg aggacgcacg tcgccttaaa gcaatttatg aaaaaaagaa      120
aaatgaactt ggcttatccc aggaatctgt cgcagacaag atggggatgg ggcagtcagg      180
cgttggtgct ttatttaatg gcatcaatgc attaaatgct tataacgccg cattgcttac      240
aaaaattctc aaagttagcg ttgaagaatt tagcccttca atcgccagag aaatctacga      300
gatgtatgaa gcggttagta tgcagccgtc acttagaagt gagtatgagt accctgtttt      360
ttctcatgtt caggcaggga tgttctcacc taagcttaga acctttacca aaggtgatgc      420
ggagagatgg gtaagcacaa ccaaaaaagc cagtgattct gcattctggc ttgaggttga      480
aggtaattcc atgaccgcac caacaggctc caagccaagc tttcctgacg gaatgttaat      540
tctcgttgac cctgagcagg ctgttgagcc aggtgatttc tgcatagcca gacttggggg      600
tgatgagttt accttcaaga aactgatcag ggatagcggt caggtgtttt tacaaccact      660
aaacccacag tacccaatga tcccatgcaa tgagagttgt tccgttgtgg ggaaagttat      720
cgctagtcag tggcctgaag agacgtttgg c                                    751

<210> SEQ ID NO 78
<211> LENGTH: 4216
<212> TYPE: DNA
<213> ORGANISM: artificial sequence
<220> FEATURE:
<223> OTHER INFORMATION: pPB828 plasmid sequence

<400> SEQUENCE: 78
cccattcgcc attcaggctg cgcaactgtt gggaagggcg atcggtgcgg gcctcttcgc       60
tattacgcca gctggcgaaa gggggatgtg ctgcaaggcg attaagttgg gtaacgccag      120
ggttttccca gtcacgacgt tgtaaaacga cggccagtgc caagctaatt accctgttat      180
ccctaggcgg accgaagctt gcatgcctgc aggtcgacgt taacttacgc ccgccctgc      240 cactcatcgc agtactgttg taattcatta agcattctgc cgacatggaa gccatcacaa      300
acggcatgat gaacctgaat cgccagcggc atcagcacct gtcgccttg cgtataatat      360 ttgcccatgg tgaaacgggg gcgaagaag ttgtccatat tggccacgtt taaatcaaaa      420
ctggtgaaac tcacccaggg attggctgag acgaaaaaca tattctcaat aaacccttta      480
```

```
gggaaatagg ccaggttttc accgtaacac gccacatctt gcgaatatat gtgtagaaac    540
tgccggaaat cgtcgtggta ttcactccag agcgatgaaa acgtttcagt ttgctcatgg    600
aaaacggtgt aacaagggtg aacactatcc catatcacca gctcaccgtc tttcattgcc    660
atacgaaatt ccggatgagc attcatcagg cgggcaagaa tgtgaataaa ggccggataa    720
aacttgtgct tattttcctt tacggtcttt aaaaaggccg taatatccag ctgaacggtc    780
tggttatagg tacattgagc aactgactga atgcctcaa atgttctttt acgatgccat     840
tgggatatat caacggtggt atatccagtg attttttct ccattttagc ttccttagct     900
cctgaaaatc tcgataactc aaaaaatacg cccggtagtg atcttatttc attatggtga    960
aagttggaac ctcttacgtg ccgatcaacg tctcattttc gccgttaaca gatctgctag   1020
cactagtaac ggccgccagt gtgctggaat tcgcccttc ataccaggcc taggcgtgat    1080
acgcctattt ttataggtta atgtcatgat aataatggtt tcttagacgt caggtggcac   1140
ttttcgggga atgtgcgcg gaaccccatt taaattgtct gcttacataa acagtaatac     1200
aaggggtgtt atgagcacaa aaaagaaacc attaacacaa gagcagcttg aggacgcacg   1260
tcgccttaaa gcaatttatg aaaaaagaa aaatgaactt ggcttatccc aggaatctgt    1320
cgcagacaag atggggatgg gcagtcagg cgttggtgct ttatttaatg gcatcaatgc    1380
attaaatgct tataacgccg cattgcttac aaaaattctc aaagttagcg ttgaagaatt   1440
tagcccttca atcgccagag aaatctacga gatgtatgaa gcggttagta tgcagccgtc   1500
acttagaagt gagtatgagt accctgtttt ttctcatgtt caggcaggga tgttctcacc   1560
taagcttaga acctttacca aaggtgatgc ggagagatgg gtaagcacaa ccaaaaaagc   1620
cagtgattct gcattctggc ttgaggttga aggtaattcc atgaccgcac caacaggctc   1680
caagccaagc tttcctgacg gaatgttaat tctcgttgac cctgagcagg ctgttgagcc   1740
aggtgatttc tgcatagcca gacttggggg tgatgagttt accttcaaga aactgatcag   1800
ggatagcggt caggtgtttt tacaaccact aaacccacag tacccaatga tcccatgcaa   1860
tgagagttgt tccgttgtgg ggaaagttat cgctagtcag tggcctgaag agacgtttgg   1920
ctgacgcgcc gaattccgga agggcgaatt ctgcagatat catgcatgtt aacatcgatc   1980
catgggcgcg ccttaattaa atttaaattc cctatagtga gtcgtattaa attcgtaatc   2040
atggtcatag ctgtttcctg tgtgaaattg ttatccgctc acaattccac acaacatacg   2100
agccggaagc ataaagtgta aagcctgggg tgcctaatga gtgagctaac tcacattaat   2160
tgcgttgcgc tcactgcccg ctttccagtc gggaaacctg tcgtgccagc tgcattaatg   2220
aatcggccaa cgcgcgggga gaggcggttt gcgtattggg cgctcttccg cttcctcgct   2280
cactgactcg ctgcgctcgg tcgttcggct gcggcgagcg gtatcagctc actcaaaggc   2340
ggtaatacgg ttatccacag aatcagggga taacgcagga agaacatgt gagcaaaagg    2400 ccagcaaaag gccaggaacc gtaaaaaggc cgcgttgctg gcgttttcc ataggctccg     2460 cccccctgac gagcatcaca aaaatcgacg ctcaagtcag aggtggcgaa acccgacagg   2520
actataaaga taccaggcgt ttccccctgg aagctccctc gtgcgctctc ctgttccgac   2580
cctgccgctt accggatacc tgtccgcctt tctcccttcg ggaagcgtgg cgctttctca   2640
tagctcacgc tgtaggtatc tcagttcggt gtaggtcgtt cgctccaagc tgggctgtgt   2700
gcacgaaccc cccgttcagc ccgaccgctg cgccttatcc ggtaactatc gtcttgagtc   2760
caacccggta agacacgact tatcgccact ggcagcagcc actggtaaca ggattagcag   2820
agcgaggtat gtaggcggtg ctacagagtt cttgaagtgg tggcctaact acggctacac   2880
```

```
tagaaggaca gtatttggta tctgcgctct gctgaagcca gttaccttcg gaaaagagt      2940 tggtagctct tgatccggca aacaaaccac cgctggtagc ggtggttttt ttgtttgcaa     3000
gcagcagatt acgcgcagaa aaaaaggatc tcaagaagat cctttgatct tttctacggg    3060
gtctgacgct cagtggaacg aaaactcacg ttaagggatt ttggtcatga gattatcaaa    3120
aaggatcttc acctagatcc ttttaaatta aaaatgaagt tttaaatcaa tctaaagtat    3180
atatgagtaa acttggtctg acagttacca atgcttaatc agtgaggcac ctatctcagc    3240
gatctgtcta tttcgttcat ccatagttgc ctgactcccc gtcgtgtaga taactacgat    3300
acgggagggc ttaccatctg gccccagtgc tgcaatgata ccgcgagacc cacgctcacc    3360
ggctccagat ttatcagcaa taaaccagcc agccggaagg gccgagcgca gaagtggtcc    3420
tgcaacttta tccgcctcca tccagtctat taattgttgc cgggaagcta gagtaagtag    3480
ttcgccagtt aatagtttgc gcaacgttgt tgccattgct acaggcatcg tggtgtcacg    3540
ctcgtcgttt ggtatggctt cattcagctc cggttcccaa cgatcaaggc gagttacatg    3600
atcccccatg ttgtgcaaaa aagcggttag ctccttcggt cctccgatcg ttgtcagaag    3660
taagttggcc gcagtgttat cactcatggt tatggcagca ctgcataatt ctcttactgt    3720
catgccatcc gtaagatgct tttctgtgac tggtgagtac tcaaccaagt cattctgaga    3780
atagtgtatg cggcgaccga gttgctcttg cccggcgtca atacgggata ataccgcgcc    3840
acatagcaga actttaaaag tgctcatcat tggaaaaggc tttccccgtc aagctctaaa    3900
tcggggcatc cctttagggt tccgatttag tgctttacgg cacctcgacc ccaaaaaact    3960
tgattagggt gatggttcac gtagtgggcc atcgccctga tagacggttt ttcgcccttt    4020
gacgttggag tccacgttct ttaatagtgg actcttgttc caaactggaa caacactcaa    4080
ccctatctcg gtctattctt ttgatttata agggattttg ccgatttcgg cctattggtt    4140
aaaaaatgag ctgatttaac aaaaatttaa cgcgaatttt aacaaaatat taacaaaata    4200
ttaacgttta caattt                                                    4216
```

<210> SEQ ID NO 79
<211> LENGTH: 4970
<212> TYPE: DNA
<213> ORGANISM: artificial sequence
<220> FEATURE:
<223> OTHER INFORMATION: pPB829 plasmid sequence

<400> SEQUENCE: 79

```
gaccggaatt cccattgcat acgttgtatc catatcataa tatgtacatt tatattggct      60
catgtccaac attaccgcca tgttgacatt gattattgac tagttattaa tagtaatcaa     120
ttacggggtc attagttcat agcccatata tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc    420
ctacttggca gtacatctac gtattagtca tcgctattac catggtgatg cggttttggc    480
agtacatcaa tgggcgtgga tagcggtttg actcacgggg atttccaagt ctccacccca    540
ttgacgtcaa tgggagtttg ttttggcacc aaaatcaacg ggactttcca aaatgtcgta    600
acaactccgc cccattgacg caaatgggcg gtaggcgtgt acggtgggag gtctatataa    660
```

| | |
|---|---|
| gcagagctcg tttagtgaac cgtcagatcg cctggagacg ccatccacgc tgttttgacc | 720 |
| tccatagaag acaccgggac cgatccagcc tccgcggccg ggaacggtgc attggaacgc | 780 |
| ggattccccg tgccaagagt gacgtaagta ccgcctatag actctatagg cacacccctt | 840 |
| tggctcttat gcatgctata ctgttttttgg cttggggcct atacaccccc gcttccttat | 900 |
| gctataggtg atggtatagc ttagcctata ggtgtgggtt attgaccatt attgaccact | 960 |
| cccctattgg tgacgatact ttccattact aatccataac atggctcttt gccacaacta | 1020 |
| tctctattgg ctatatgcca atactctgtc cttcagagac tgacacggac tctgtatttt | 1080 |
| tacaggatgg ggtcccattt attatttaca aattcacata acaacaacg ccgtcccccg | 1140 |
| tgcccgcagt ttttattaaa catagcgtgg gatctccacg cgaatctcgg gtacgtgttc | 1200 |
| cggacatggg ctcttctccg gtagcggcg agcttccaca tccgagccct ggtcccatgc | 1260 |
| ctccagcggc tcatggtcgc tcggcagctc cttgctccta acagtggagg ccagacttag | 1320 |
| gcacagcaca atgcccacca ccaccagtgt gccgcacaag gccgtggcgg tagggtatgt | 1380 |
| gtctgaaaat gagcgtggag attgggctcg cacggctgac gcagatggaa gacttaaggc | 1440 |
| agcggcagaa gaagatgcag gcagctgagt tgttgtattc tgataagagt cagaggtaac | 1500 |
| tcccgttgcg gtgctgttaa cggtggaggg cagtgtagtc tgagcagtac tcgttgctgc | 1560 |
| cgcgcgcgcc accagacata atagctgaca gactaacaga ctgttccttt ccatgggtct | 1620 |
| tttctgcagt caccgtcgtc gacacgtgtg atcagatatc gcggccgctc tagaccaggc | 1680 |
| cctggatcca gatctgctgt gccttctagt tgccagccat ctgttgtttg cccctccccc | 1740 |
| gtgccttcct tgaccctgga aggtgccact cccactgtcc tttcctaata aaatgaggaa | 1800 |
| attgcatcgc attgtctgag taggtgtcat tctattctgg ggggtggggt ggggcaggac | 1860 |
| agcaagggg aggattggga agacaatagc aggcatgctg gggatgcggt gggctctatg | 1920 |
| ggtacccagg tgctgaagaa ttgacccggt tcctcctggg ccagaaagaa gcaggcacat | 1980 |
| ccccttctct gtgacacacc ctgtccacgc ccctggttct tagttccagc cccactcata | 2040 |
| ggacactcat agctcaggag ggctccgcct tcaatcccac ccgctaaagt acttggagcg | 2100 |
| gtctctccct ccctcatcag cccaccaaac caaacctagc ctccaagagt gggaagaaat | 2160 |
| taaagcaaga taggctatta agtgcagagg gagagaaaat gcctccaaca tgtgaggaag | 2220 |
| taatgagaga aatcatagaa tttcttccgc ttcctcgctc actgactcgc tgcgctcggt | 2280 |
| cgttcggctg cggcgagcgg tatcagctca ctcaaaggcg gtaatacggt tatccacaga | 2340 |
| atcagggat aacgcaggaa agaacatgtg agcaaaaggc cagcaaaagg ccaggaaccg | 2400 |
| taaaaaggcc gcgttgctgg cgttttttcca taggctccgc cccctgacg agcatcacaa | 2460 |
| aaatcgacgc tcaagtcaga ggtggcgaaa cccgacagga ctataaagat accaggcgtt | 2520 |
| tccccctgga agctccctcg tgcgctctcc tgttccgacc ctgccgctta ccggatacct | 2580 |
| gtccgccttt ctcccttcgg gaagcgtggc gctttctcat agctcacgct gtaggtatct | 2640 |
| cagttcggtg taggtcgttc gctccaagct gggctgtgtg cacgaacccc ccgttcagcc | 2700 |
| cgaccgctgc gccttatccg gtaactatcg tcttgagtcc aacccggtaa gacacgactt | 2760 |
| atcgccactg gcagcagcca ctggtaacag gattagcaga gcgaggtatg taggcggtgc | 2820 |
| tacagagttc ttgaagtggt ggcctaacta cggctacact agaagaacag tatttggtat | 2880 |
| ctgcgctctg ctgaagccag ttaccttcgg aaaaagagtt ggtagctctt gatccggcaa | 2940 |
| acaaaccacc gctggtagcg gtggtttttt tgtttgcaag cagcagatta cgcgcagaaa | 3000 |
| aaaaggatct caagaagatc ctttgatctt ttctacgggg tctgacgctc agtggaacga | 3060 |

```
aaactcacgt taagggattt tggtcatgag attatcaaaa aggatcttca cctagatcct    3120
tttaaattaa aaatgaagtt ttaaatcaat ctaaagtata tatgagtaaa cttggtctga    3180
cagttaccaa tgcttaatca gtgaggcacc tatctcagcg atctgtctat ttcgttcatc    3240
catagttgcc tgactcgggg gggggggcg ctgaggtctg cctcgtgaag aaggtgttgc    3300
tgactcatac caggcctagg tgatacgcct atttttatag gttaatgtca tgataataat    3360
ggtttcttag acgtcaggtg gcacttttcg gggaaatgtg cgcggaaccc catttaaatt    3420
gtctgcttac ataaacagta atacaagggg tgttatgagc acaaaaaaga aaccattaac    3480
acaagagcag cttgaggacg cacgtcgcct taaagcaatt tatgaaaaaa agaaaaatga    3540
acttggctta tcccaggaat ctgtcgcaga caagatgggg atggggcagt caggcgttgg    3600
tgctttattt aatggcatca atgcattaaa tgcttataac gccgcattgc ttacaaaaat    3660
tctcaaagtt agcgttgaag aatttagccc ttcaatcgcc agagaaatct acgagatgta    3720
tgaagcggtt agtatgcagc cgtcacttag aagtgagtat gagtaccctg ttttttctca    3780
tgttcaggca gggatgttct cacctaagct tagaaccttt accaaaggtg atgcggagag    3840
atgggtaagc acaaccaaaa aagccagtga ttctgcattc tggcttgagg ttgaaggtaa    3900
ttccatgacc gcaccaacag gctccaagcc aagctttcct gacggaatgt taattctcgt    3960
tgaccctgag caggctgttg agccaggtga tttctgcata gccagacttg ggggtgatga    4020
gtttaccttc aagaaactga tcagggatag cggtcaggtg ttttttacaac cactaaaccc    4080 acagtaccca atgatcccat gcaatgagag ttgttccgtt gtggggaaag ttatcgctag    4140
tcagtggcct gaagagacgt ttggctgagg cgcgccgaat tccggtccgt tacgccccgc    4200
cctgccactc atcgcagtac tgttgtaatt cattaagcat tctgccgaca tggaagccat    4260
cacaaacggc atgatgaacc tgaatcgcca gcggcatcag caccttgtcg ccttgcgtat    4320
aatatttgcc catggtgaaa acggggggcga agaagttgtc catattggcc acgtttaaat    4380
caaaactggt gaaactcacc cagggattgg ctgagacgaa aaacatattc tcaataaacc    4440
ctttagggaa ataggccagg ttttcaccgt aacacgccac atcttgcgaa tatatgtgta    4500
gaaactgccg gaaatcgtcg tggtattcac tccagagcga tgaaaacgtt tcagtttgct    4560
catggaaaac ggtgtaacaa gggtgaacac tatcccatat caccagctca ccgtctttca    4620
ttgccatacg aaattccgga tgagcattca tcaggcgggc aagaatgtga ataaaggccg    4680
gataaaactt gtgcttattt ttctttacgg tctttaaaaa ggccgtaata tccagctgaa    4740
cggtctggtt ataggtacat tgagcaactg actgaaatgc ctcaaaatgt tctttacgat    4800
gccattggga tatatcaacg gtggtatatc cagtgatttt tttctccatt ttagcttcct    4860
tagctcctga aaatctcgat aactcaaaaa atacgcccgg tagtgatctt atttcattat    4920
ggtgaaagtt ggaacctctt acgtgccgat caacgtctca ttttcgcccg                4970
```

<210> SEQ ID NO 80
<211> LENGTH: 63
<212> TYPE: DNA
<213> ORGANISM: artificial sequence
<220> FEATURE:
<223> OTHER INFORMATION: PB1320 primer

<400> SEQUENCE: 80

```
gccgatcaac gtctcatttt cgccgttaac agatctttat ttgttaactg ttaattgtcc    60
ttg                                                                   63
```

```
<210> SEQ ID NO 81
<211> LENGTH: 24
<212> TYPE: DNA
<213> ORGANISM: artificial sequence
<220> FEATURE:
<223> OTHER INFORMATION: PB1321 primer

<400> SEQUENCE: 81
agatctgtta acggcgaaaa tgag                                          24

<210> SEQ ID NO 82
<211> LENGTH: 52
<212> TYPE: DNA
<213> ORGANISM: artificial sequence
<220> FEATURE:
<223> OTHER INFORMATION: PB1322 primer

<400> SEQUENCE: 82
aaaacgctac aaaaatgccc gatcctttac gccccgccct gccactcatc gc          52

<210> SEQ ID NO 83
<211> LENGTH: 35
<212> TYPE: DNA
<213> ORGANISM: artificial sequence
<220> FEATURE:
<223> OTHER INFORMATION: P1 promoter (2)

<400> SEQUENCE: 83
atcatgacat taacctataa aataggcgt atcac                               35
```